United States Patent
Zhang

(10) Patent No.: US 8,501,779 B2
(45) Date of Patent: Aug. 6, 2013

(54) POLYMORPHS OF DONEPEZIL SALTS, PREPARATION METHODS AND USES THEREOF

(75) Inventor: Hesheng Zhang, Tianjin (CN)

(73) Assignee: Tianjin Hemay Bio-Tech Co., Ltd., Tianjin (CN)

( * ) Notice: Subject to any disclaimer, the term of this patent is extended or adjusted under 35 U.S.C. 154(b) by 426 days.

(21) Appl. No.: 12/748,248

(22) Filed: Mar. 26, 2010

(65) Prior Publication Data

US 2010/0311793 A1  Dec. 9, 2010

Related U.S. Application Data

(63) Continuation of application No. PCT/CN2008/001646, filed on Sep. 24, 2008.

(30) Foreign Application Priority Data

Sep. 28, 2007 (CN) .......................... 2007 1 0061212
Jan. 15, 2008 (CN) .......................... 2008 1 0052067
Sep. 24, 2008 (CN) .......................... 2008 1 0211731

(51) Int. Cl.
  *A61K 31/445* (2006.01)
  *C07D 211/32* (2006.01)

(52) U.S. Cl.
  USPC ........................... 514/319; 546/205; 546/206

(58) Field of Classification Search
  USPC .................................. 514/319; 546/205, 206
  See application file for complete search history.

(56) References Cited

U.S. PATENT DOCUMENTS

| 4,895,841 A | 1/1990 | Sugimoto et al. |
| 7,592,459 B2 * | 9/2009 | Arad et al. ..................... 546/206 |
| 2008/0194628 A1 | 8/2008 | Mezei et al. ................... 514/319 |

FOREIGN PATENT DOCUMENTS

| CN | 101039910 A | | 9/2007 |
| IN | 1162/CHE/2008 | * | 11/2009 |
| WO | 2006/032432 A2 | | 3/2006 |
| WO | WO2006/030249 | * | 3/2006 |

OTHER PUBLICATIONS

Braga et al. "Making crystals . . . " J Roy. Soc. Chem. Chem. Commun. p. 3635-3645 (2005).*
Davies "Changing the salt changing the drug" Phar, J. v. 266 p. 322-323 (2001).*
Kirk_othemer "Crystallization" Encyclopedia of Chem. Tech. vo. 8, p. 96-147 (2002).*
Nagarajan "Porcess for the prep . . . " CA152:287146 (2009).*
Polymorph definition Chemistry Dictionary p. 1 (2012).*
Polymophism ACPS meeting p. 1-5 (2002).*
Seddon "Pseudopolymorph . . . " Crys. Growth & design v.4(6) 1087 (2004).*
Vippagunta et al. "Crystalline solids" Adv. Drug, Del. Rev. 48 p. 3-26 (2001).*

* cited by examiner

*Primary Examiner* — Celia Chang
(74) *Attorney, Agent, or Firm* — Seed IP Law Group PLLC

(57) ABSTRACT

Preparation methods of mesylate, para-toluenesulfonate, succinate, tartrate, sulphate, nitrate, phosphate, salicylate, fumarate, maleate, gallate, acetylsalicylate, benzenesulphonate, citrate, aspartate, glutaminate, lactate, gluconate, ascorbate, malonate, malate, sorbate, acetate or formate of 1-benzyl-4-[(5,6-dimethoxy-1-indanon)-2-yl]methylpiperidine (i.e., Donepezil). Novel polymorphs formed from these salts and their preparation methods. Co-crystals formed from Donepezil hydrochloride and maleic acid, fumaric acid, citric acid, salicylic acid, tartaric acid or succinic acid.

7 Claims, 65 Drawing Sheets

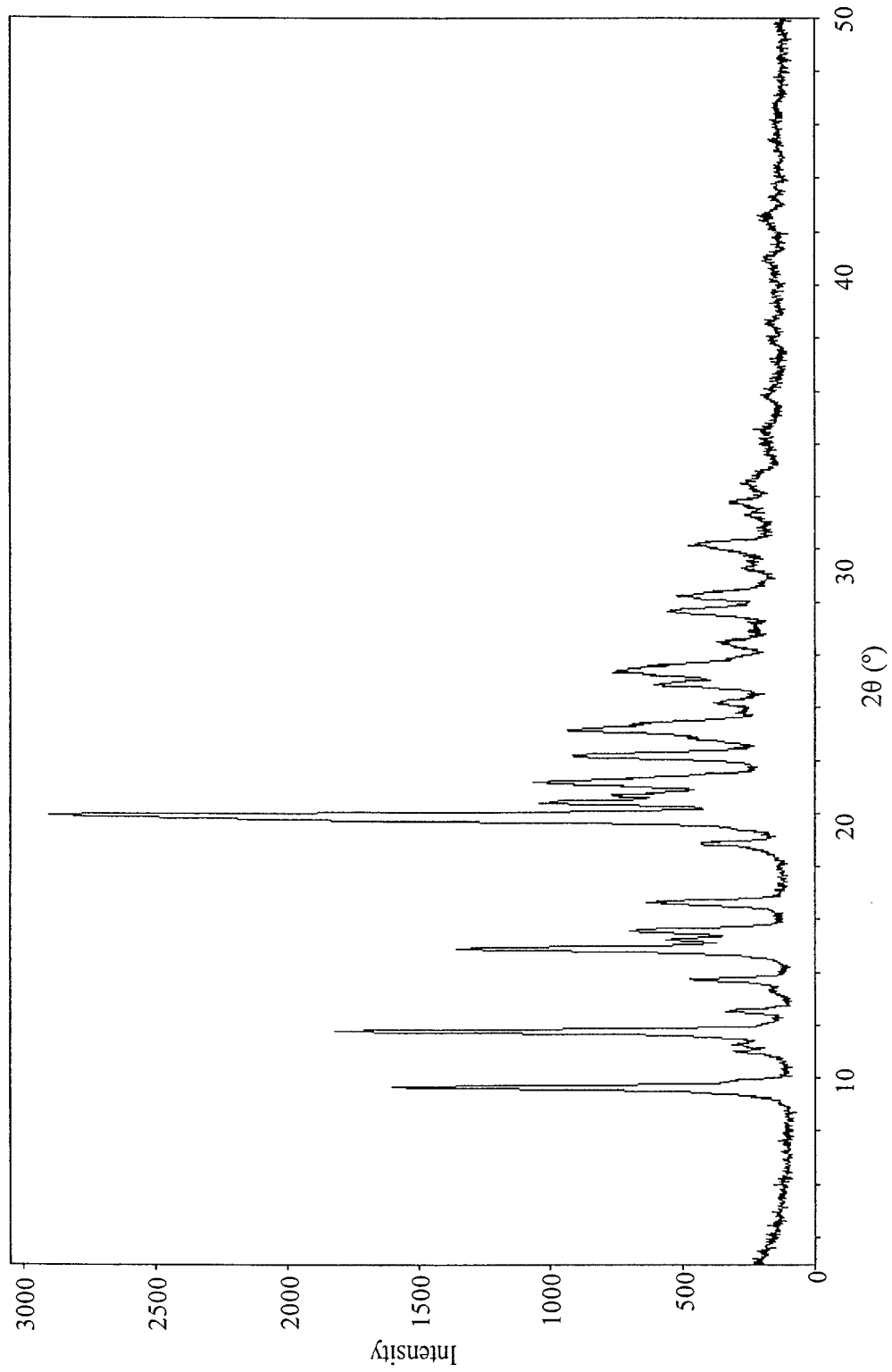
FIG. 1-A-1

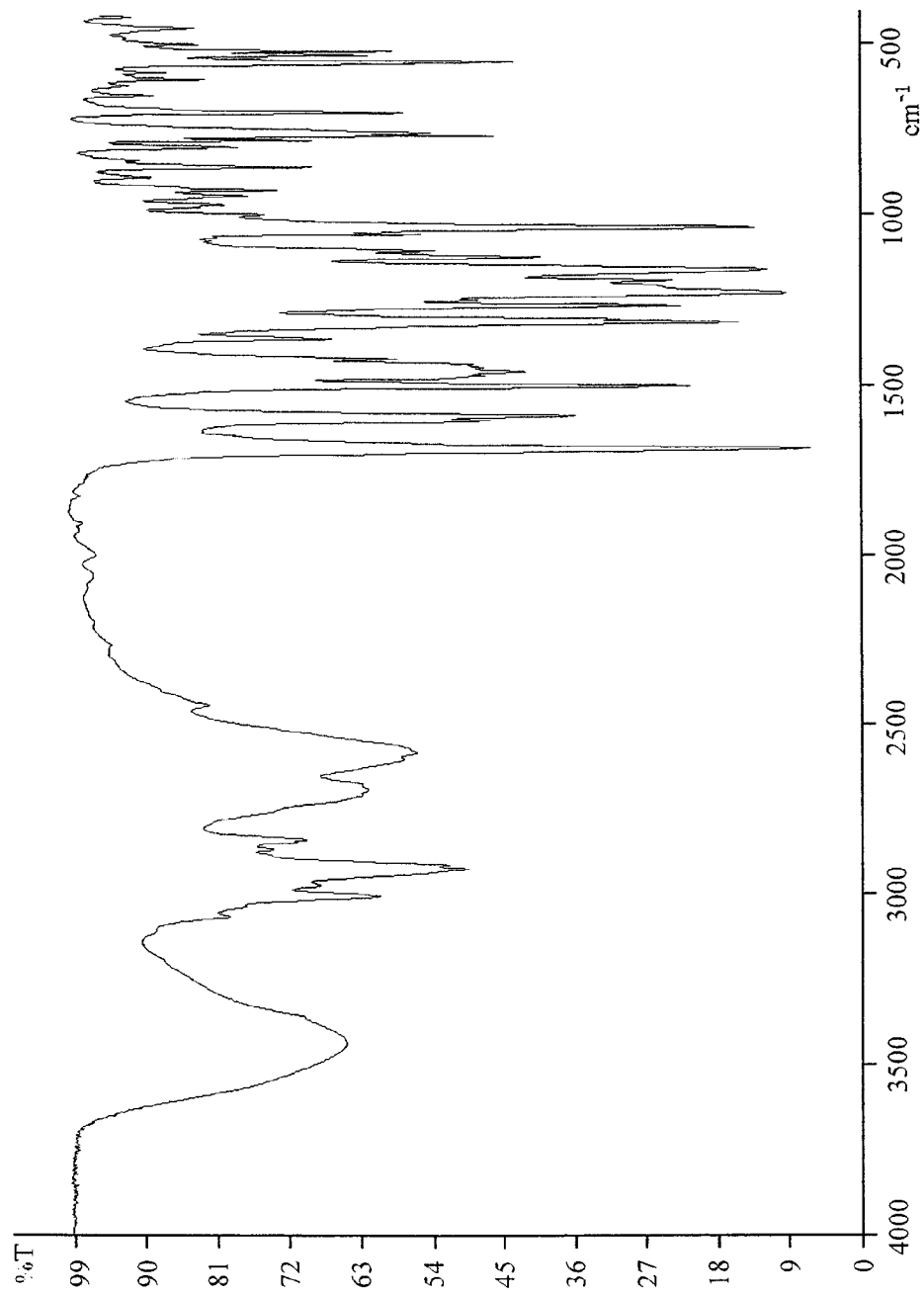
FIG. 1-A-2

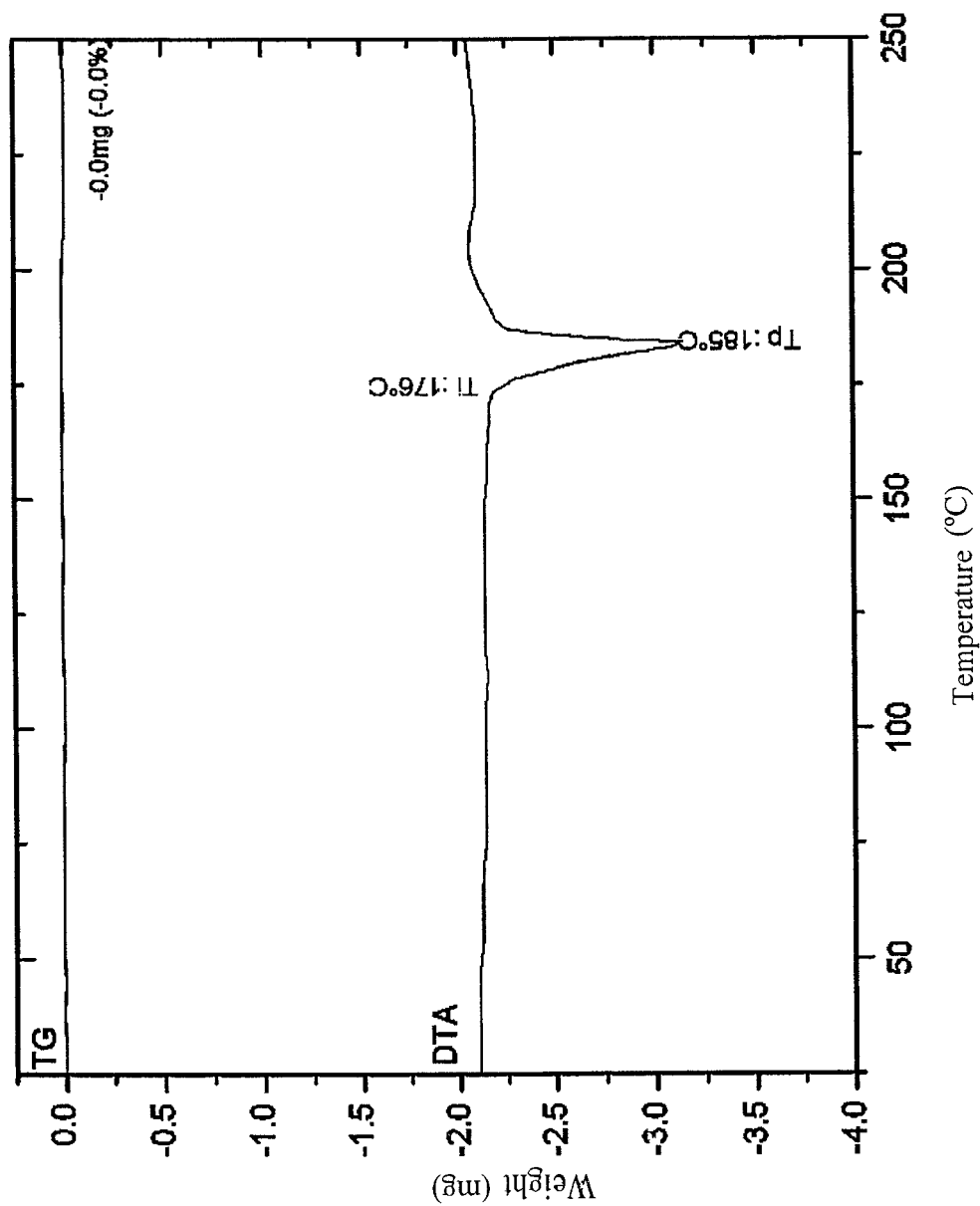
FIG. 1-A-3

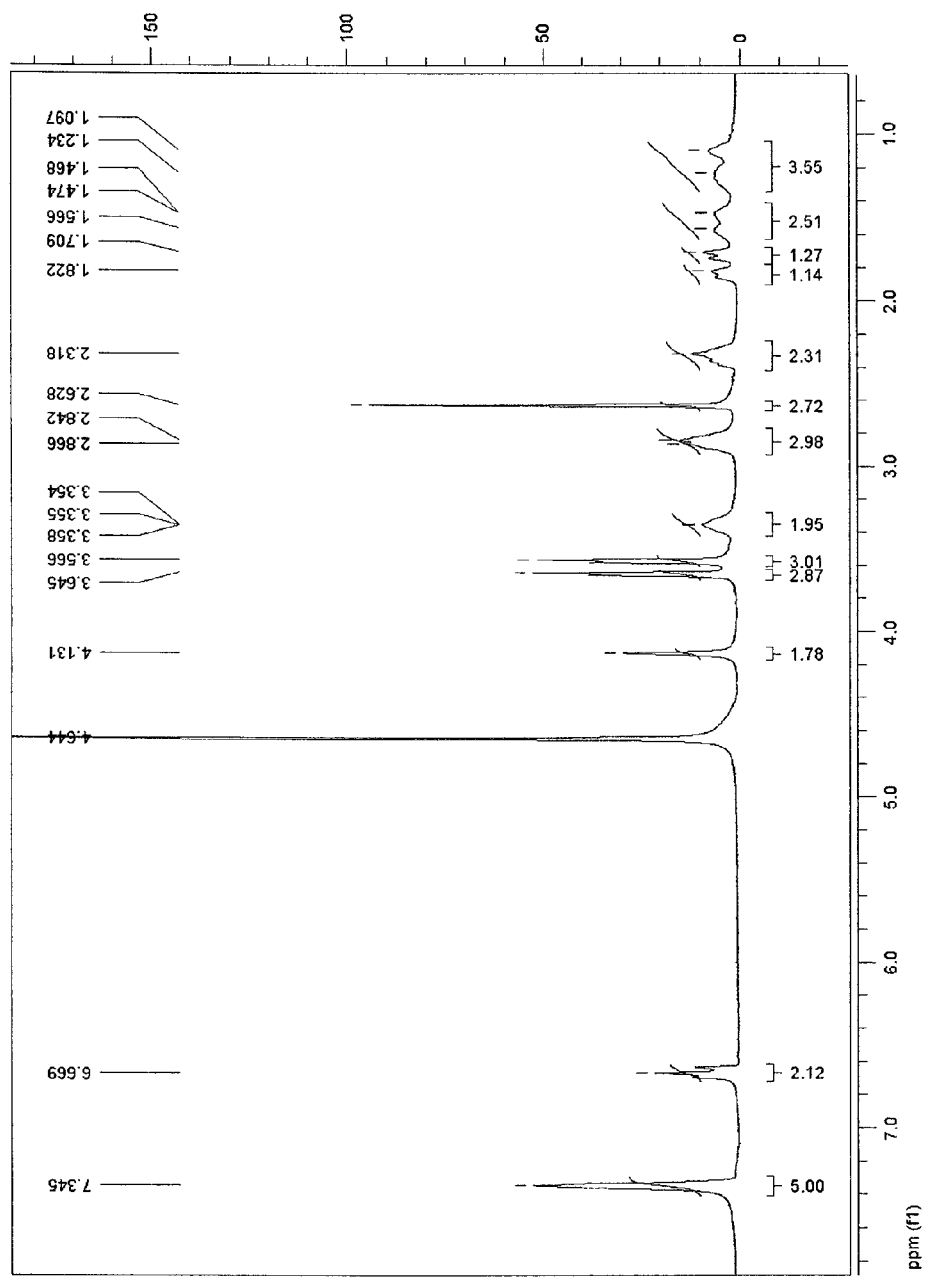
FIG. 1-A-4

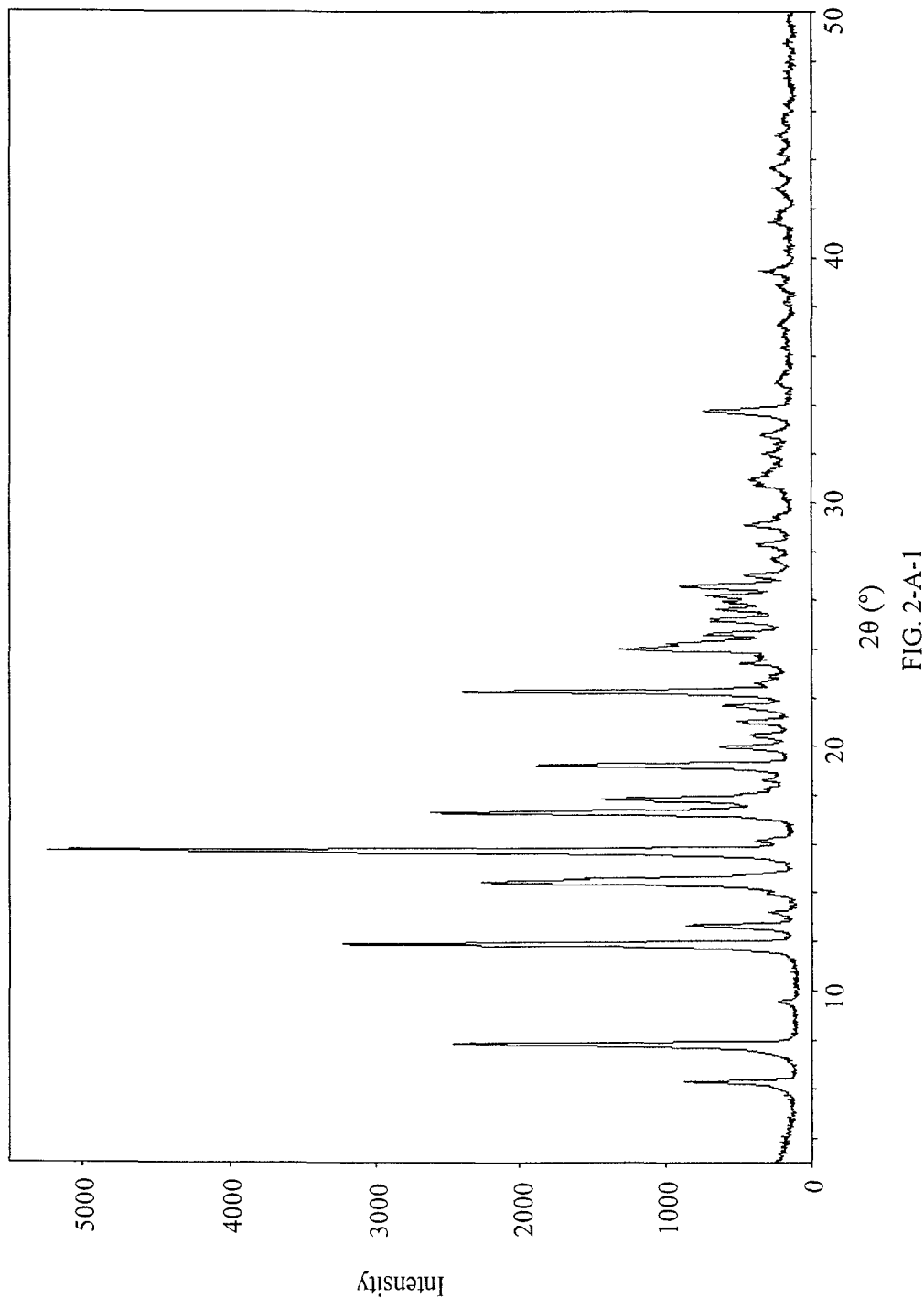
FIG. 2-A-1

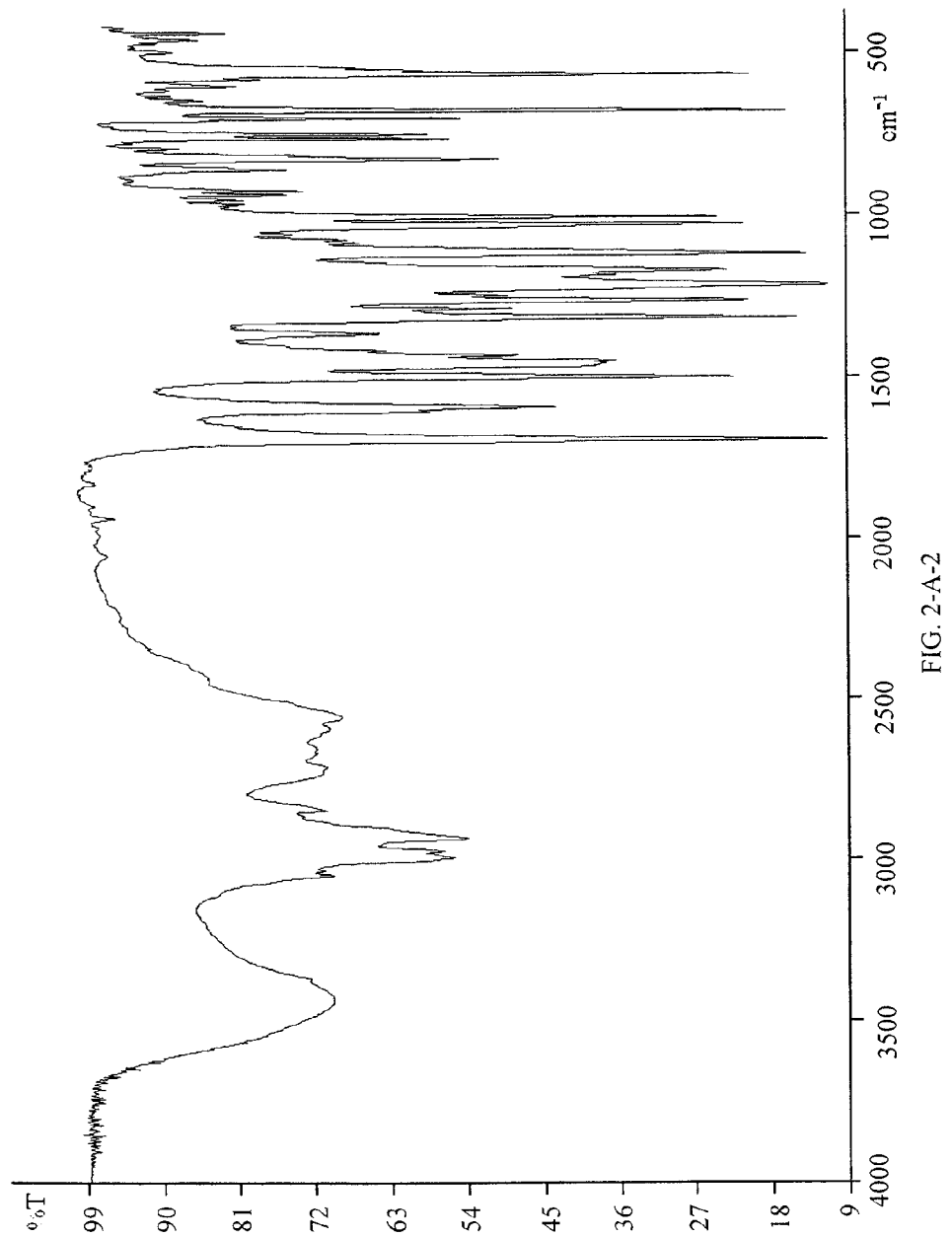
FIG. 2-A-2

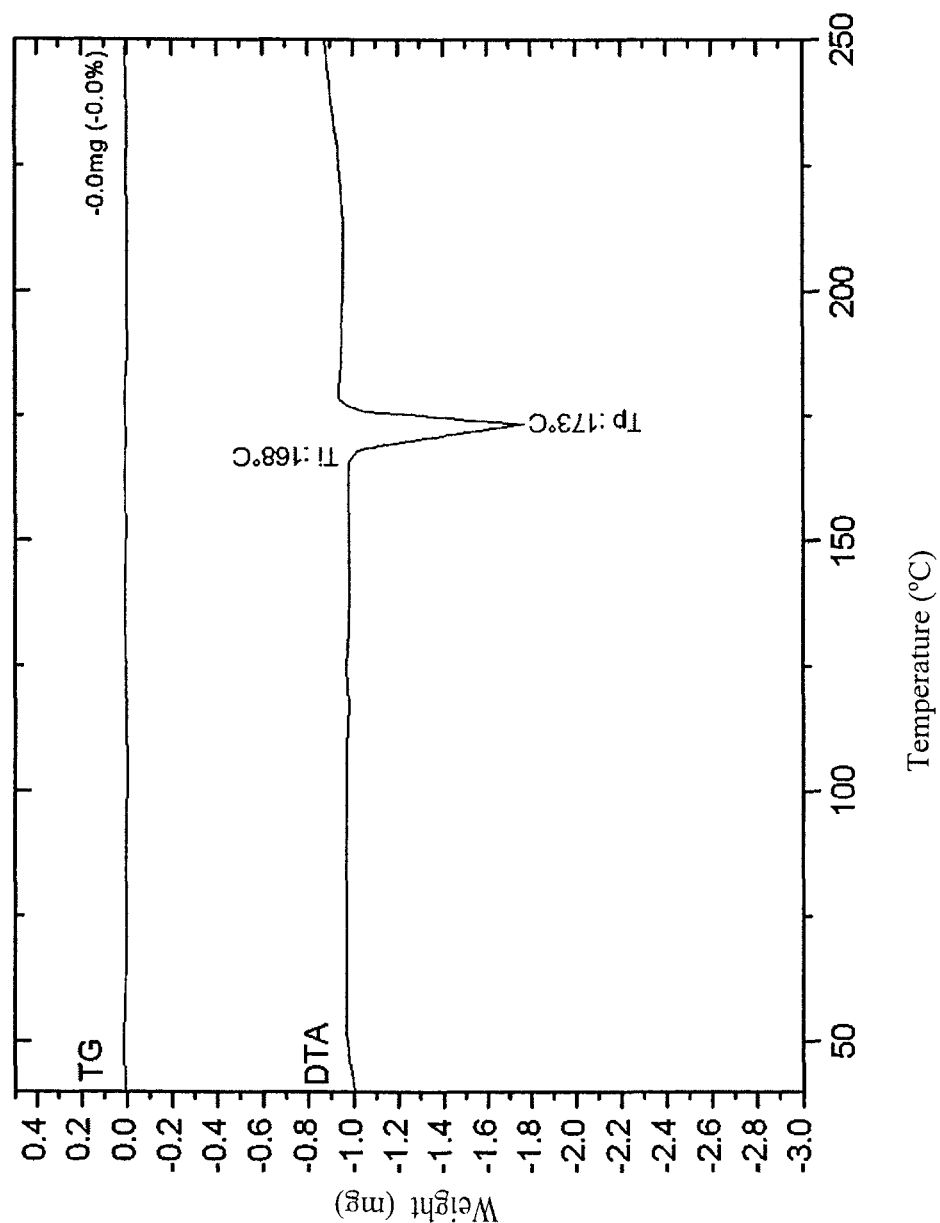
FIG. 2-A-3

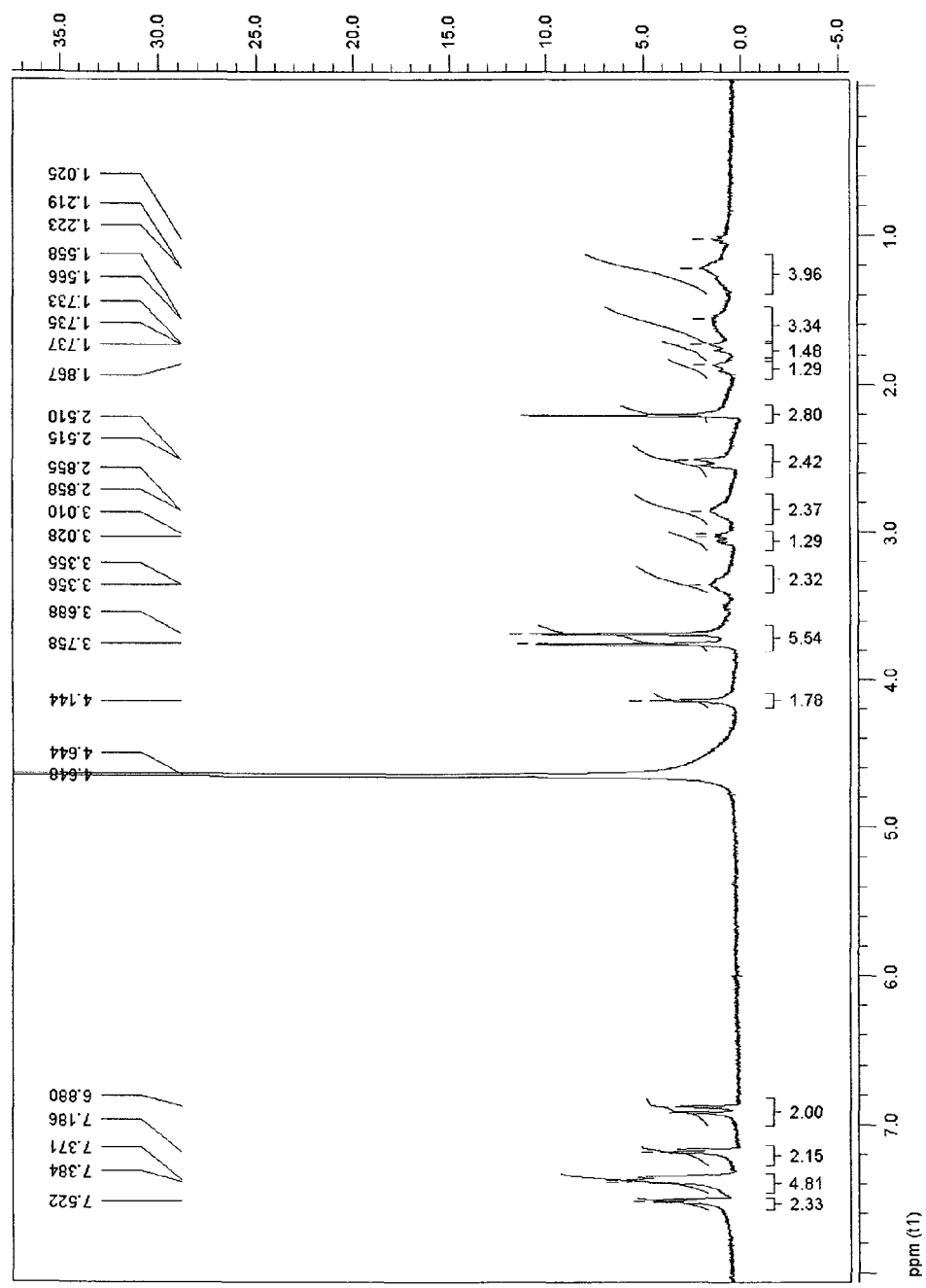
FIG. 2-A-4

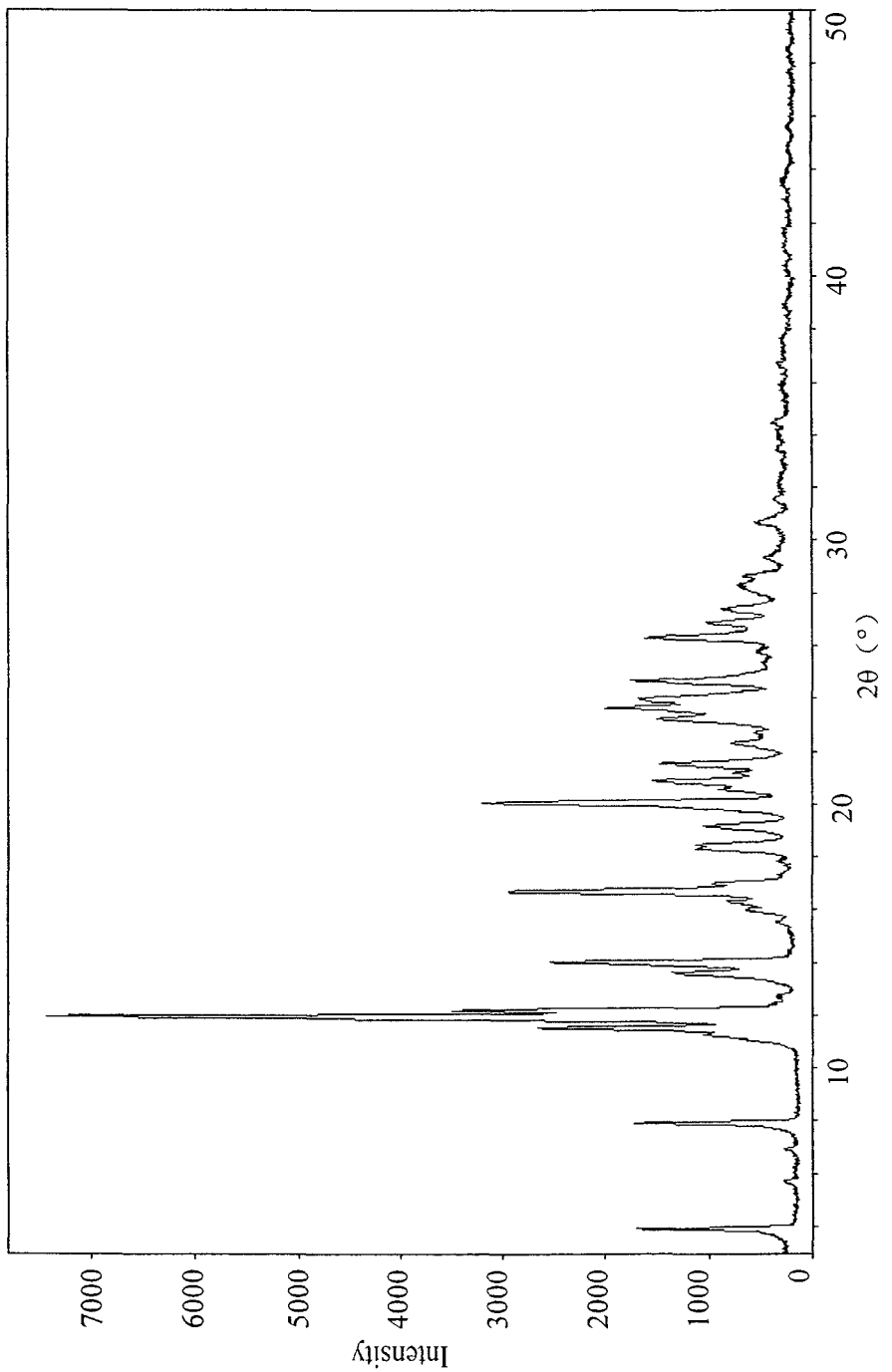
FIG. 3-A-1

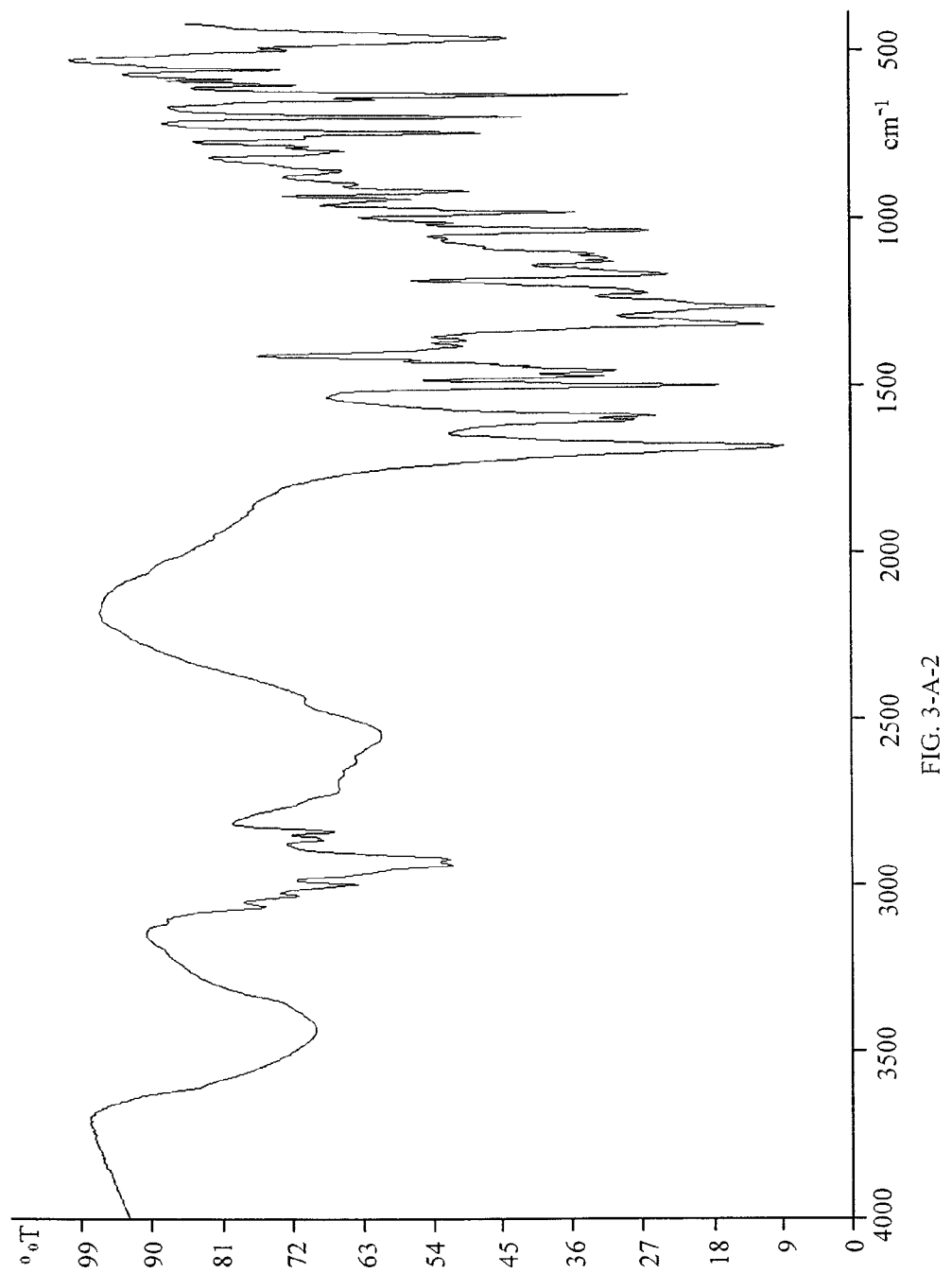
FIG. 3-A-2

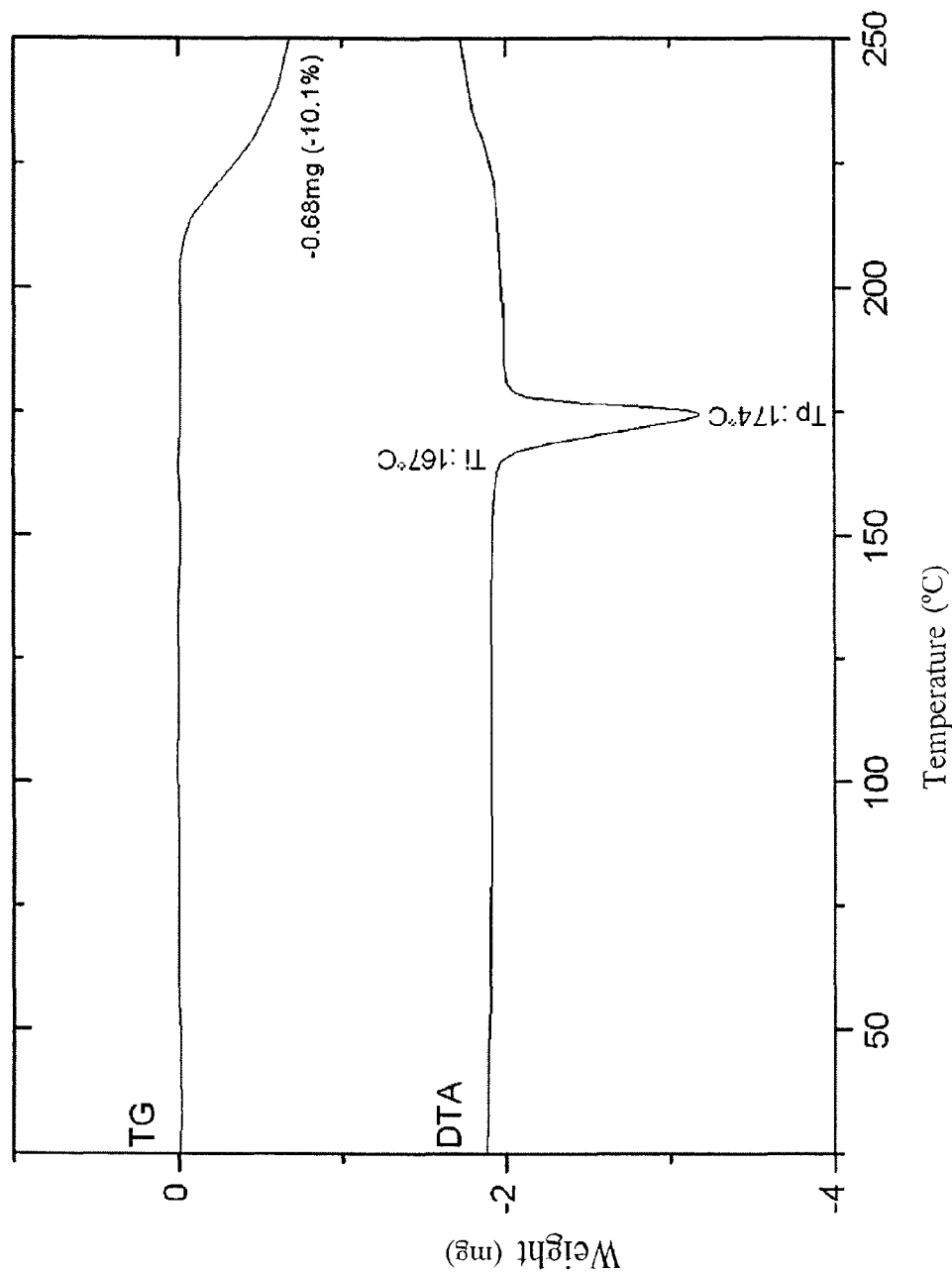
FIG. 3-A-3

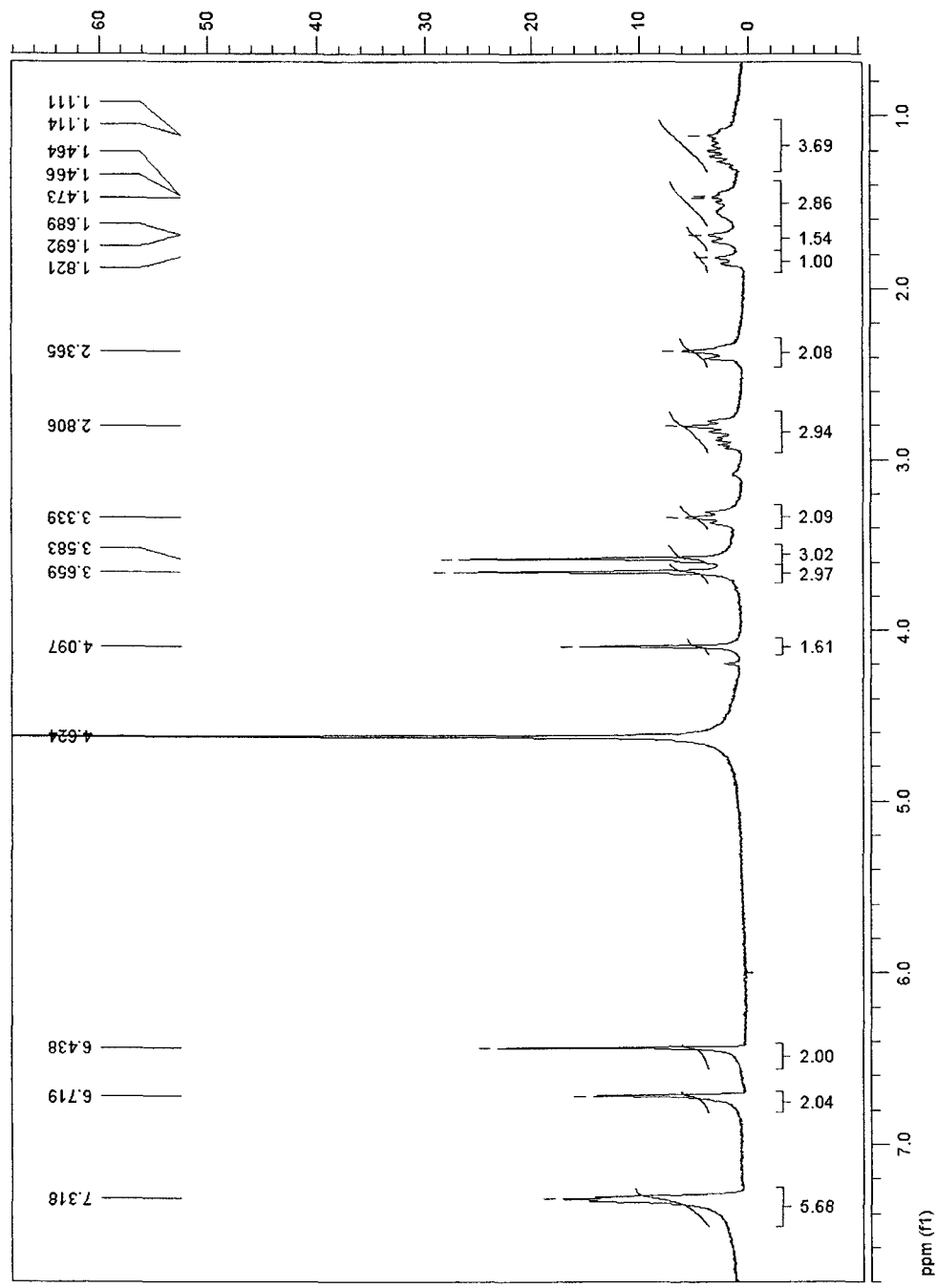
FIG. 3-A-4

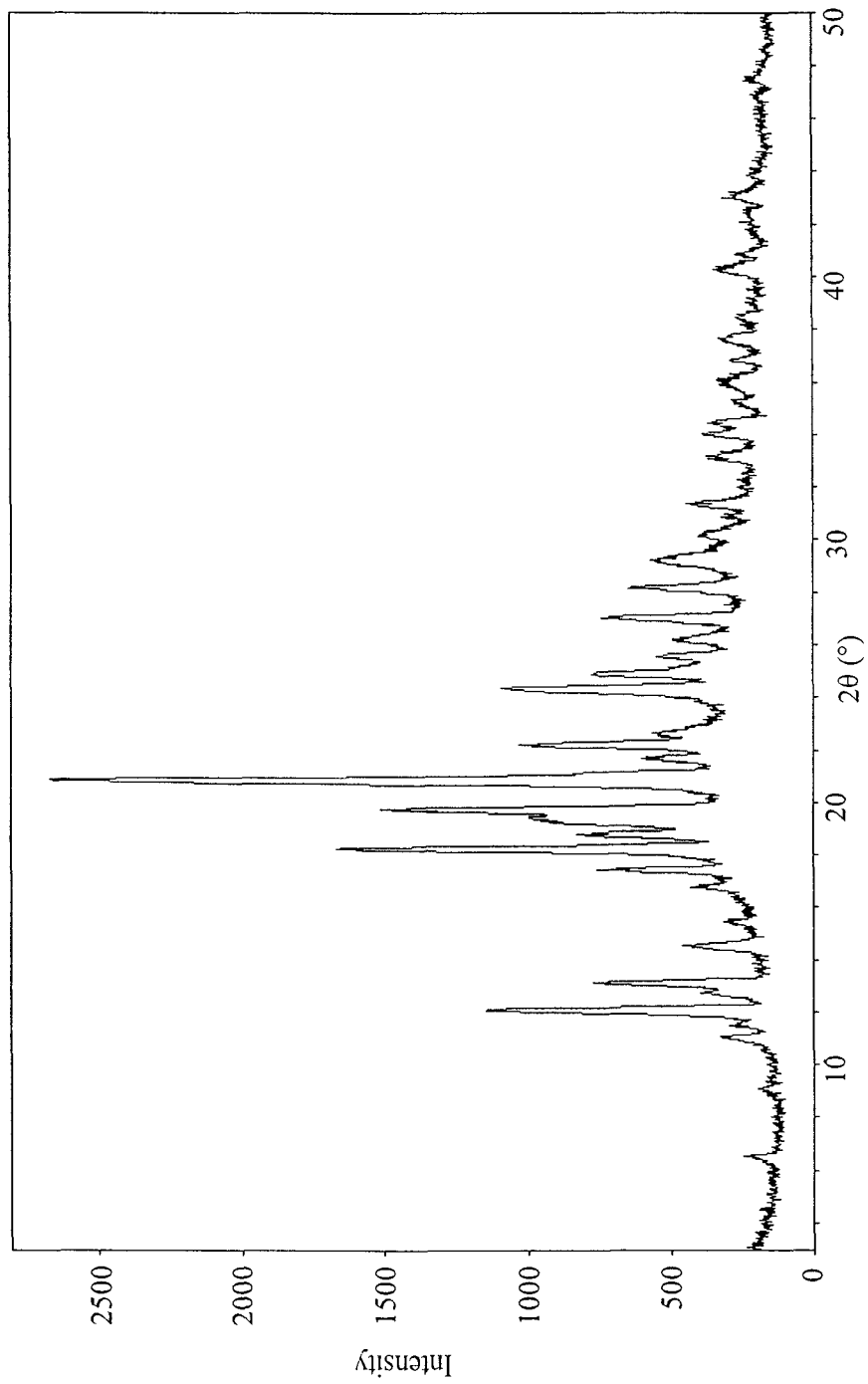
FIG. 4-A-1

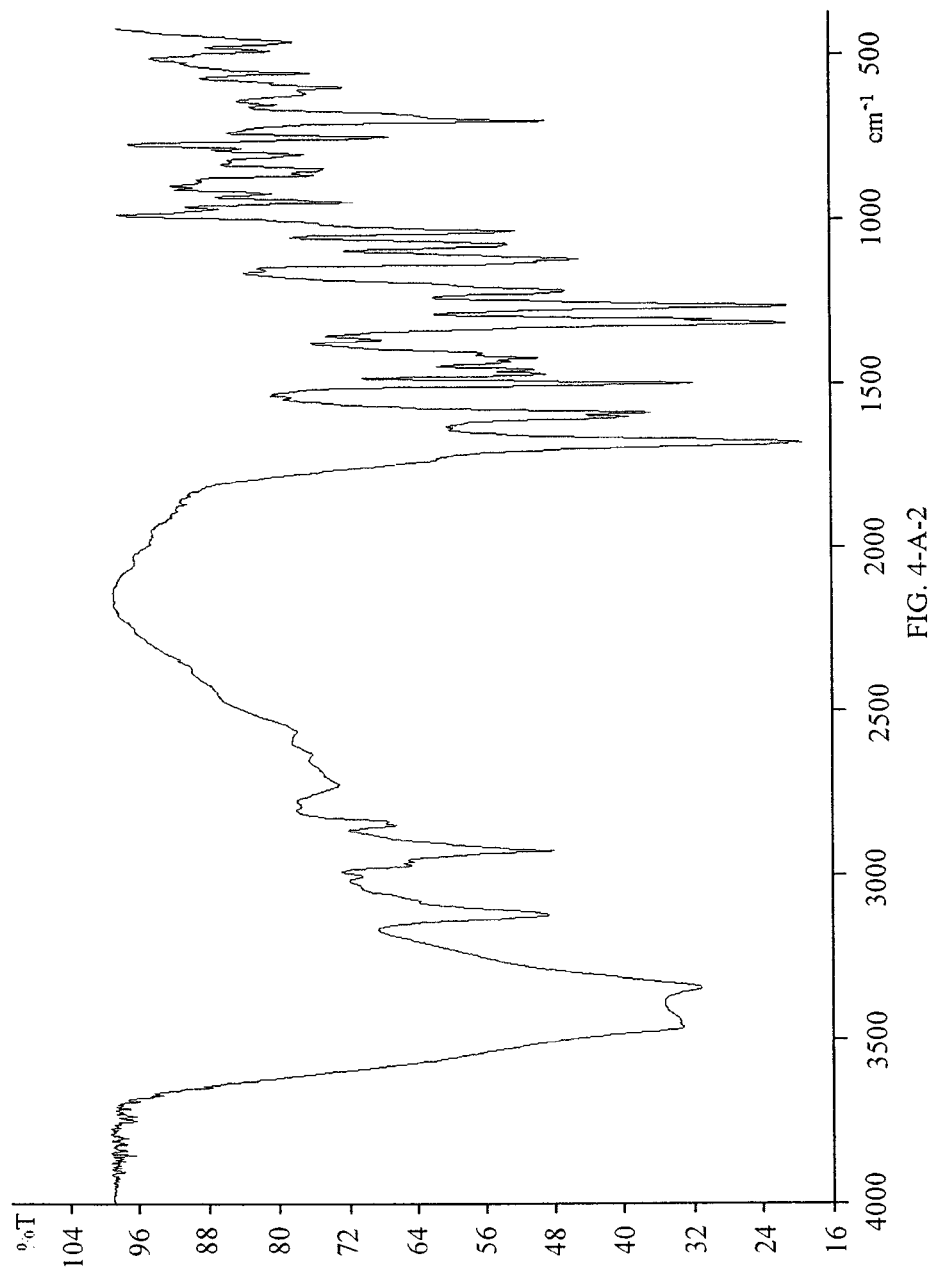
FIG. 4-A-2

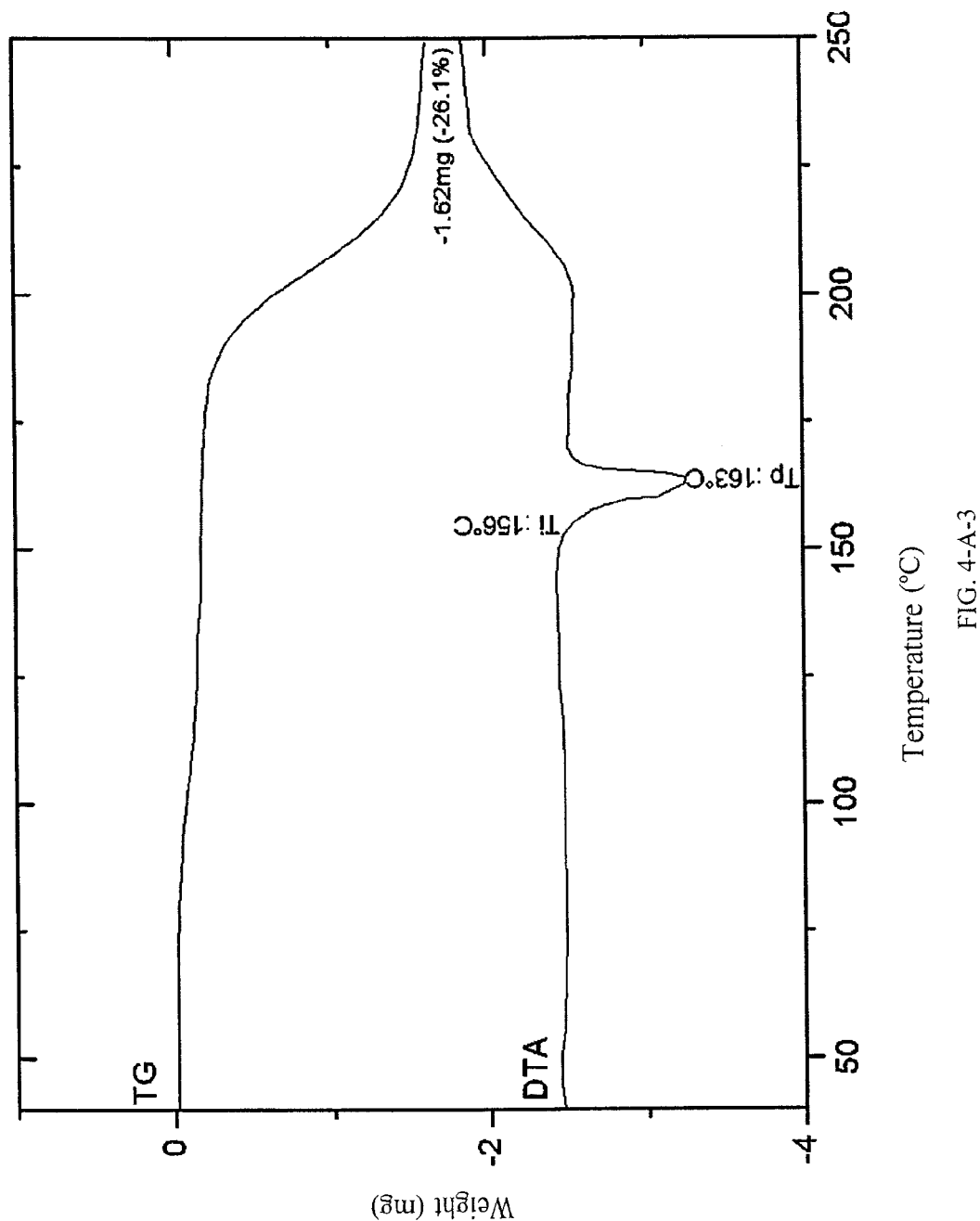
FIG. 4-A-3

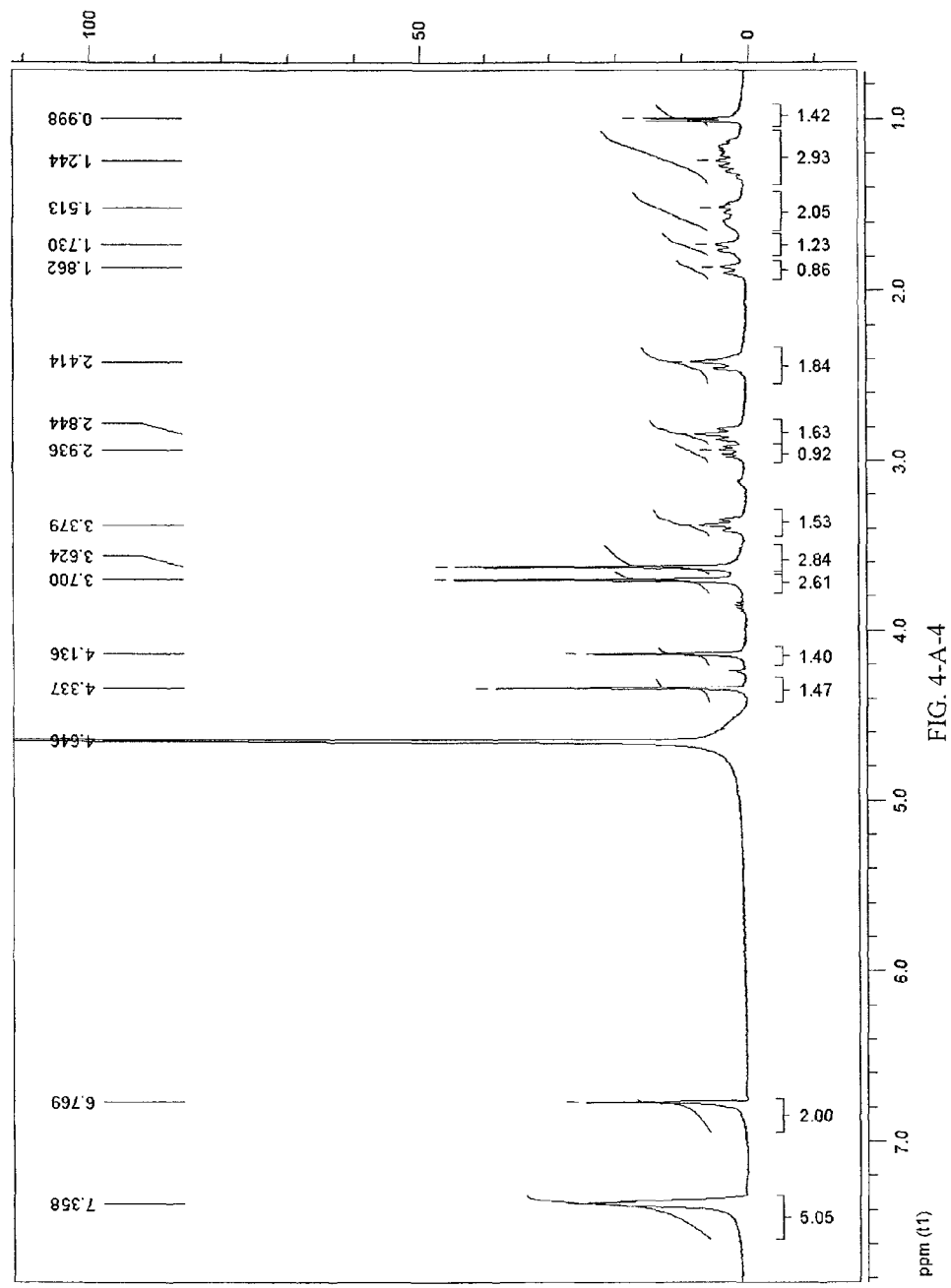
FIG. 4-A-4

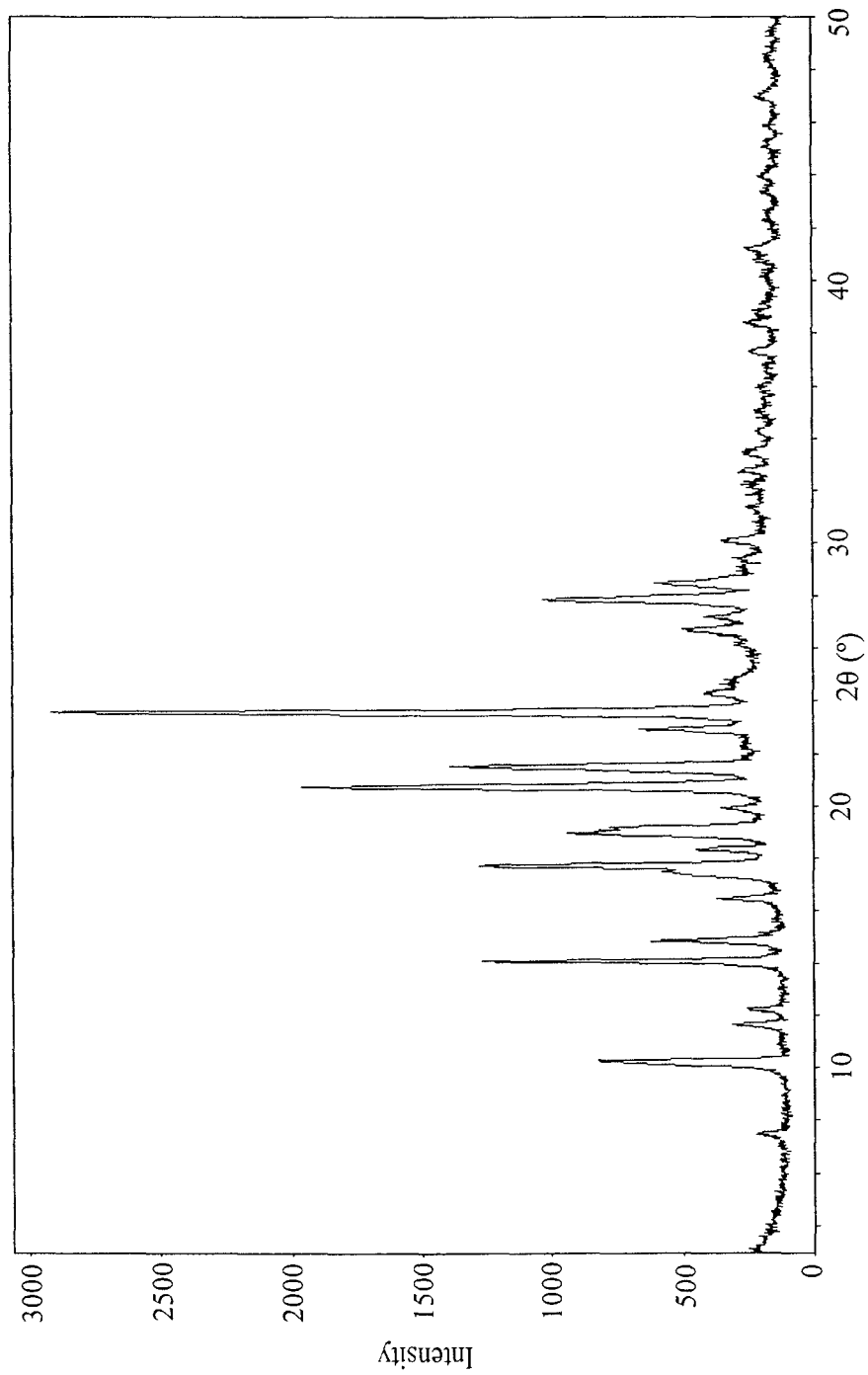
FIG. 5-A-1

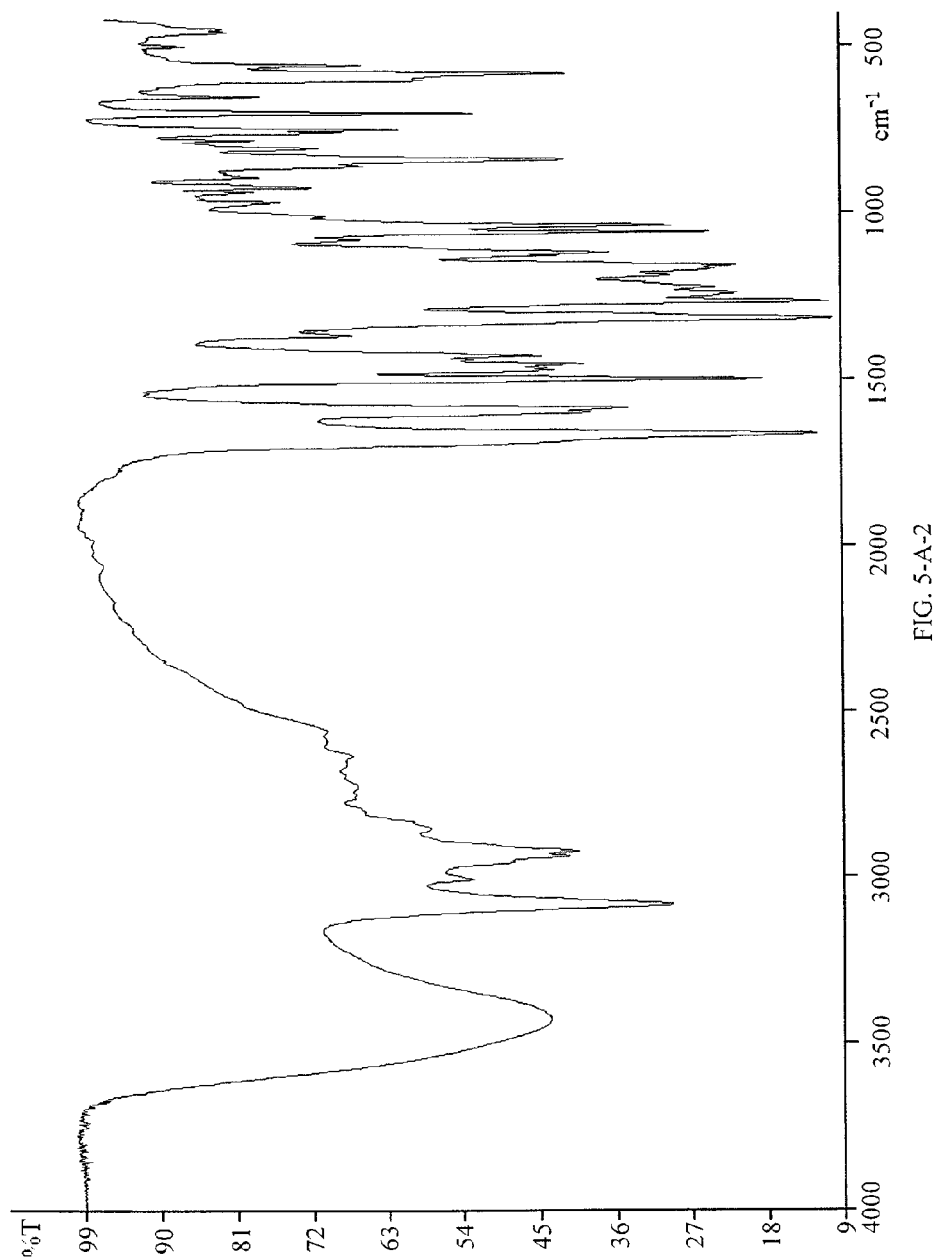
FIG. 5-A-2

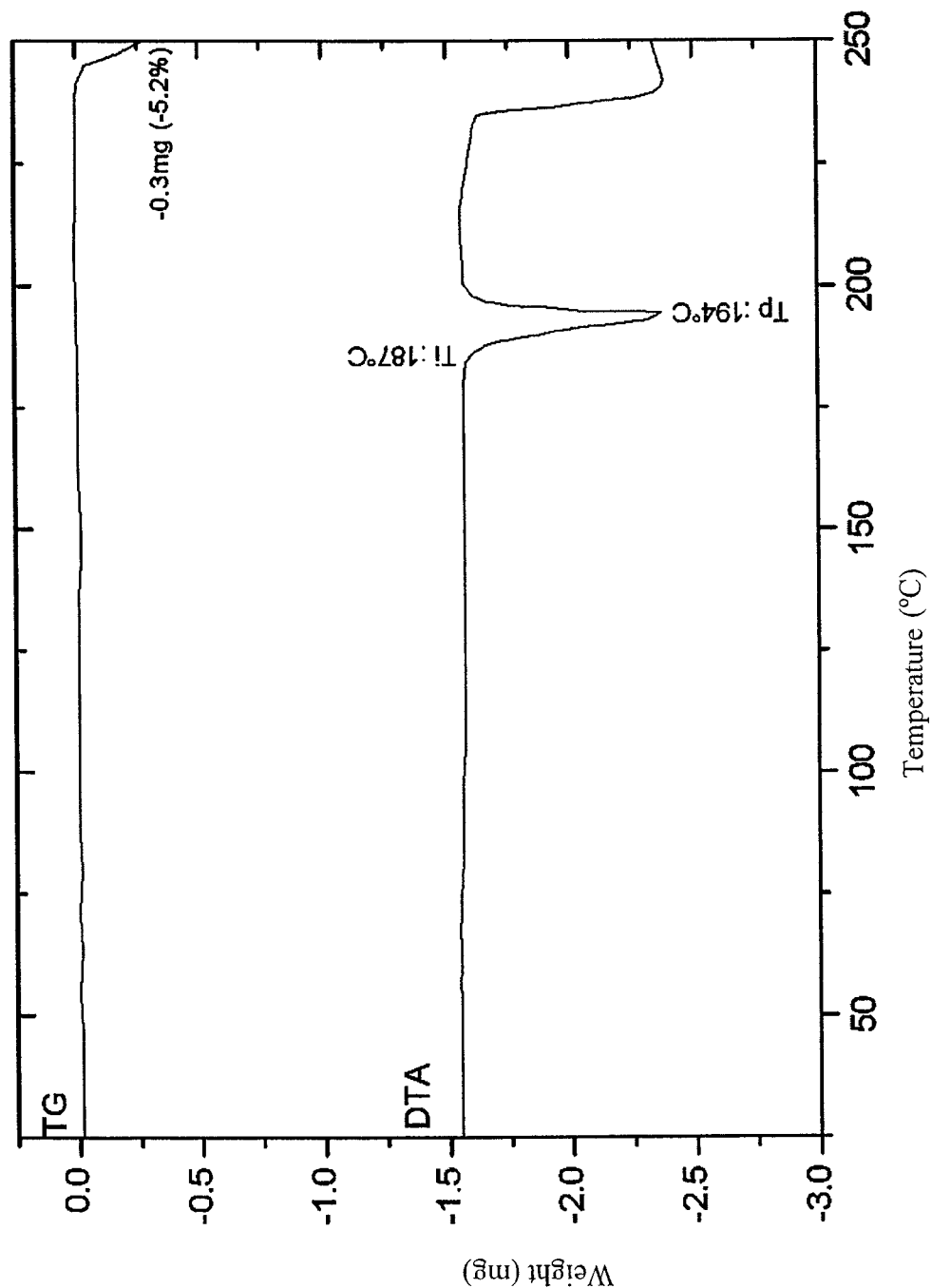
FIG. 5-A-3

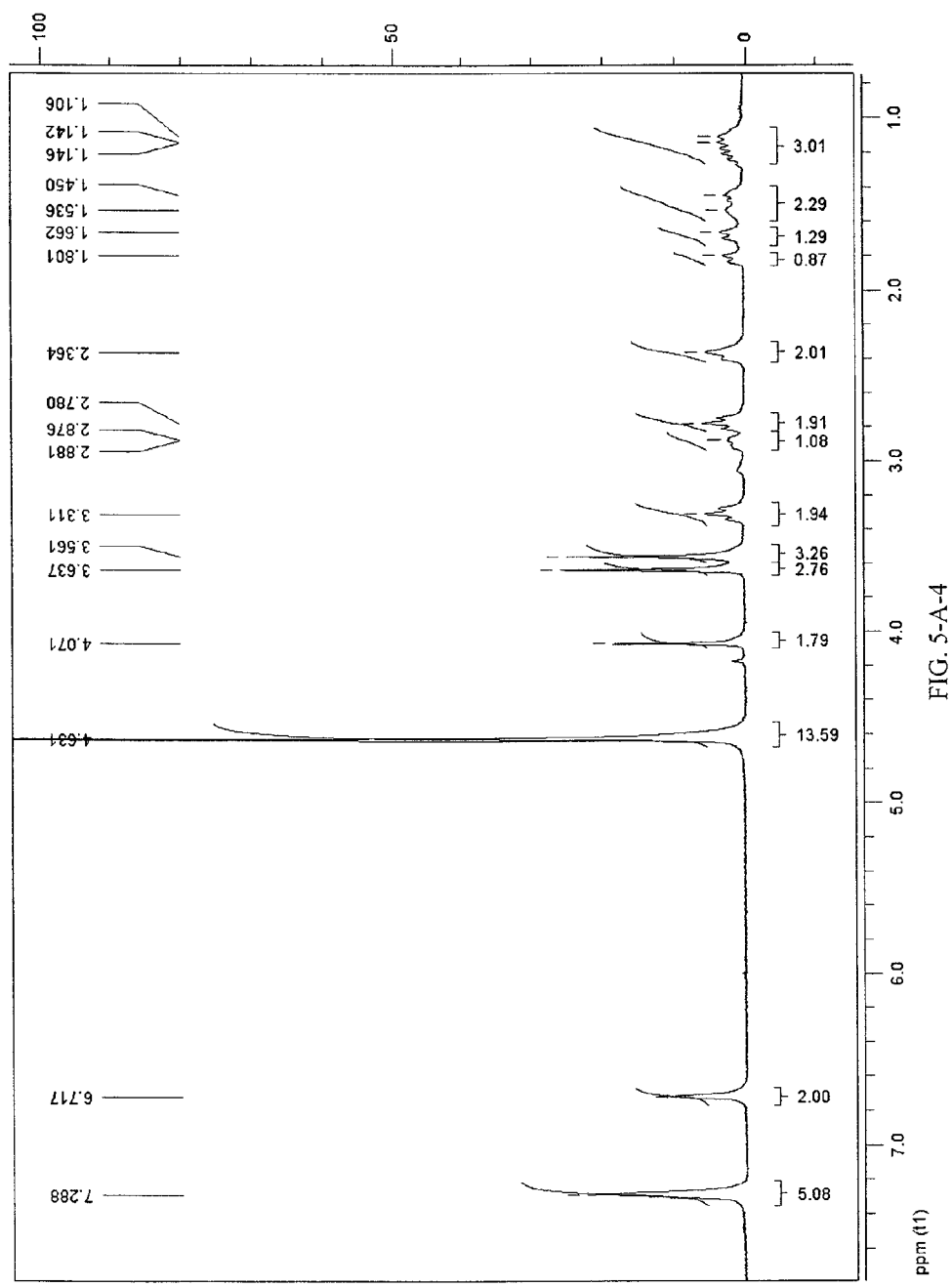
FIG. 5-A-4

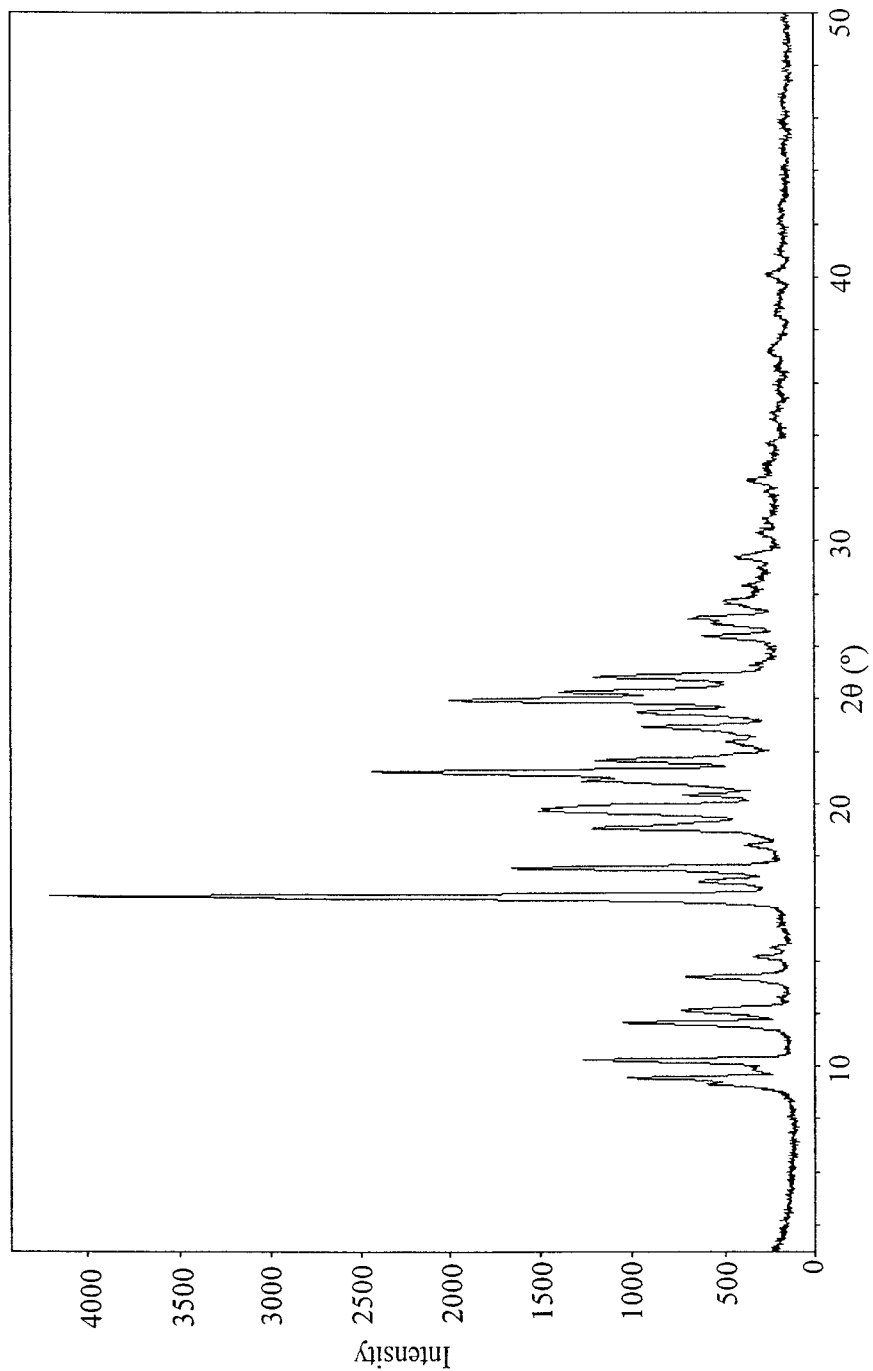
FIG. 5-B-1

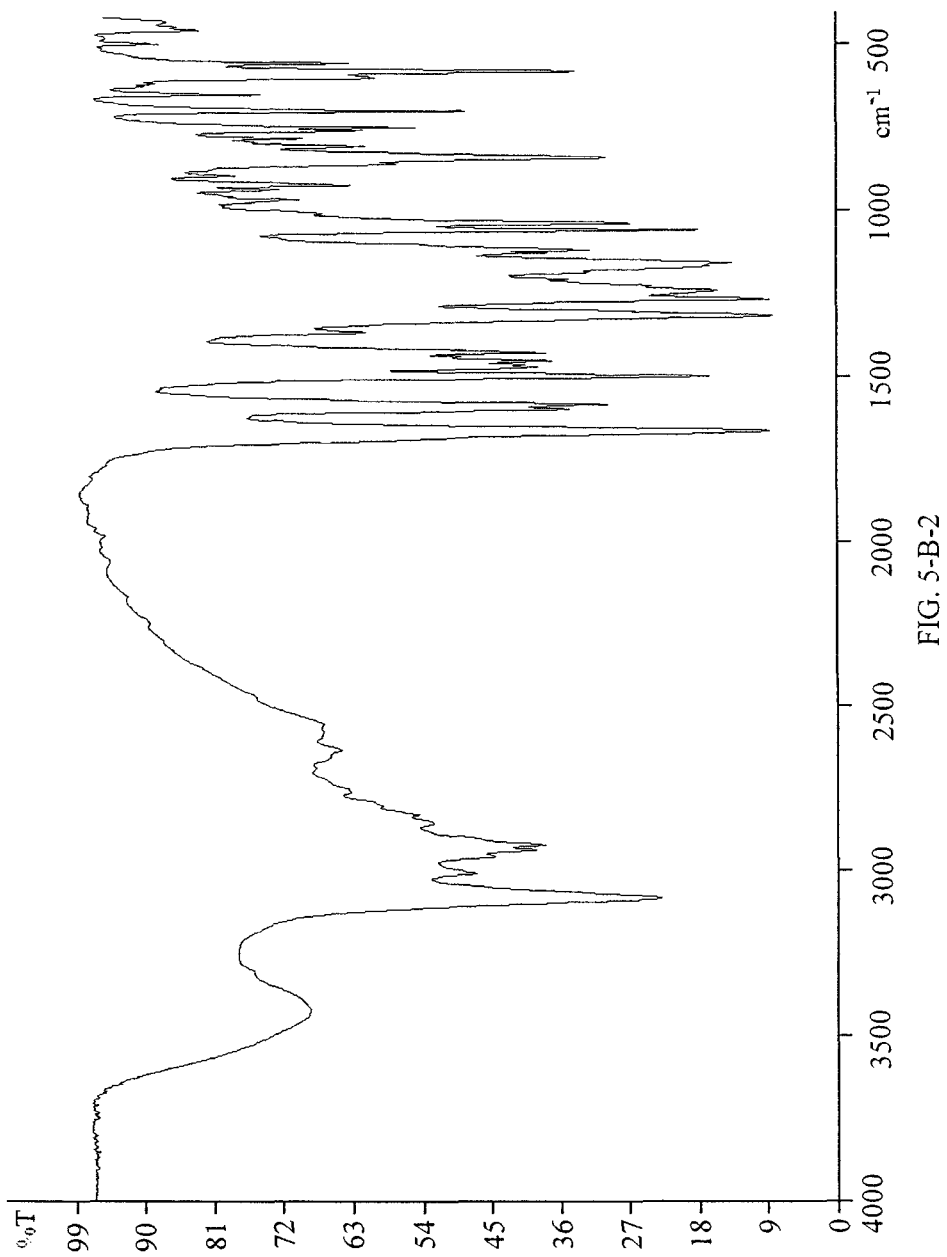
FIG. 5-B-2

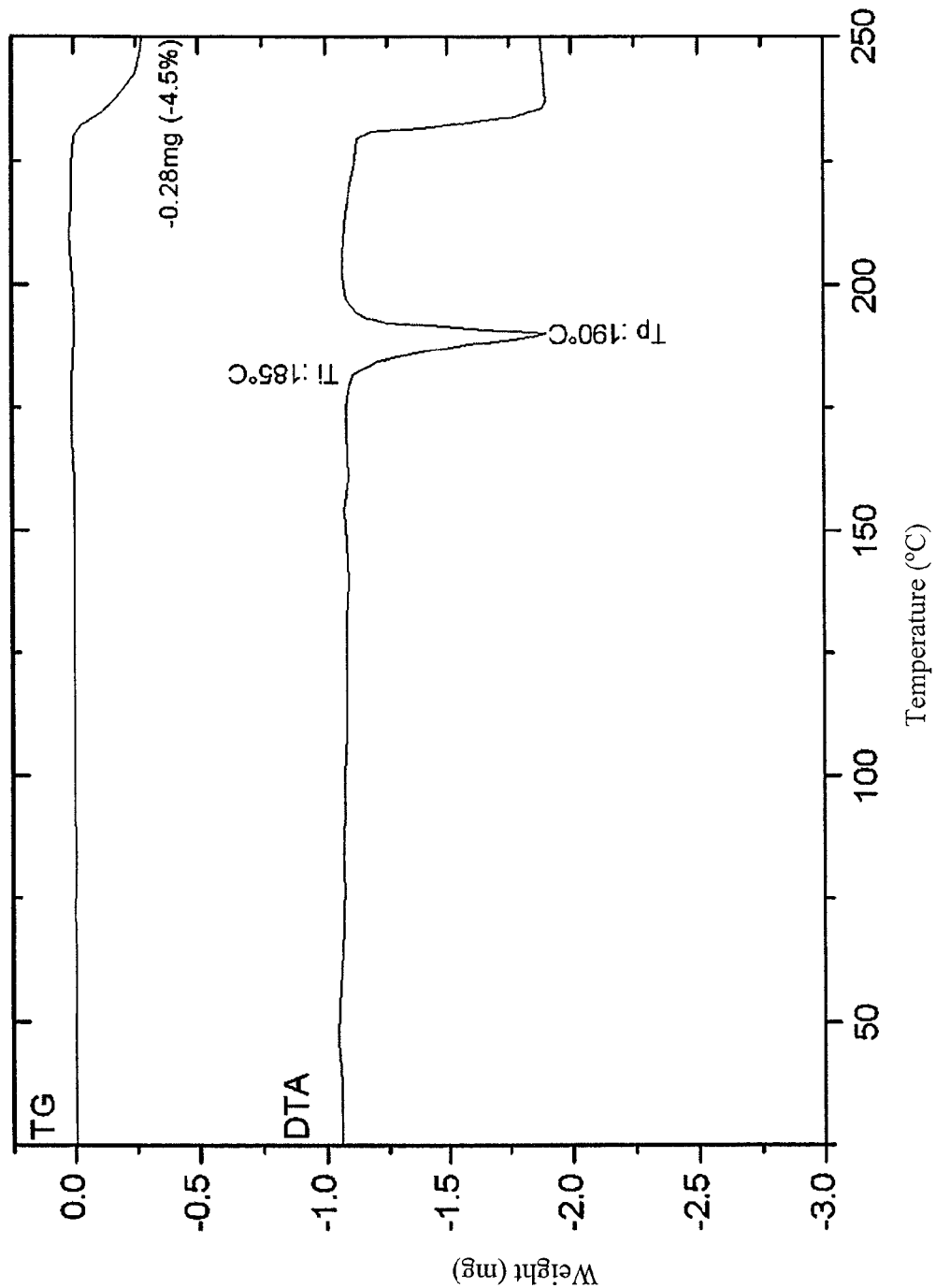
FIG. 5-B-3

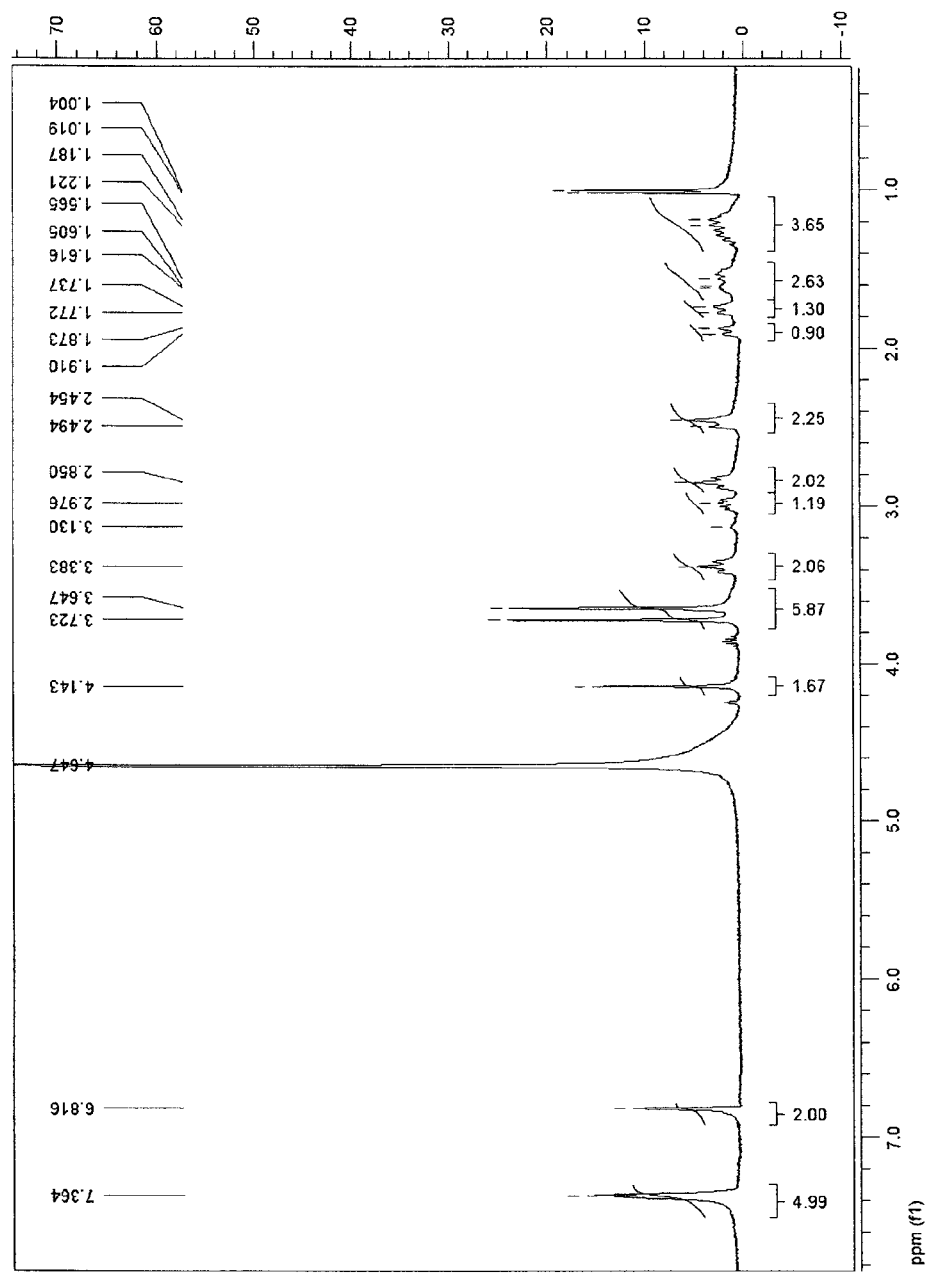
FIG. 5-B-4

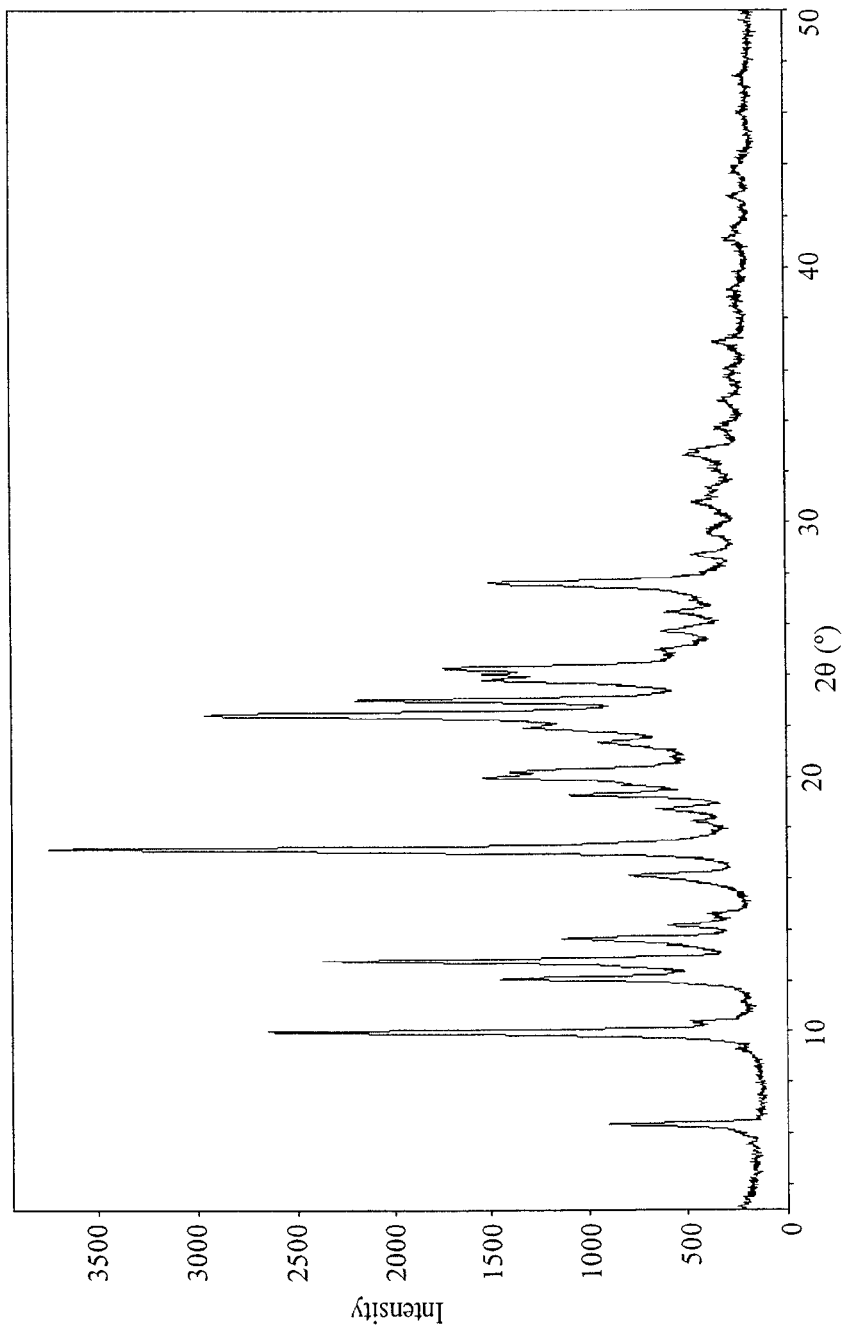
FIG. 6-A-1

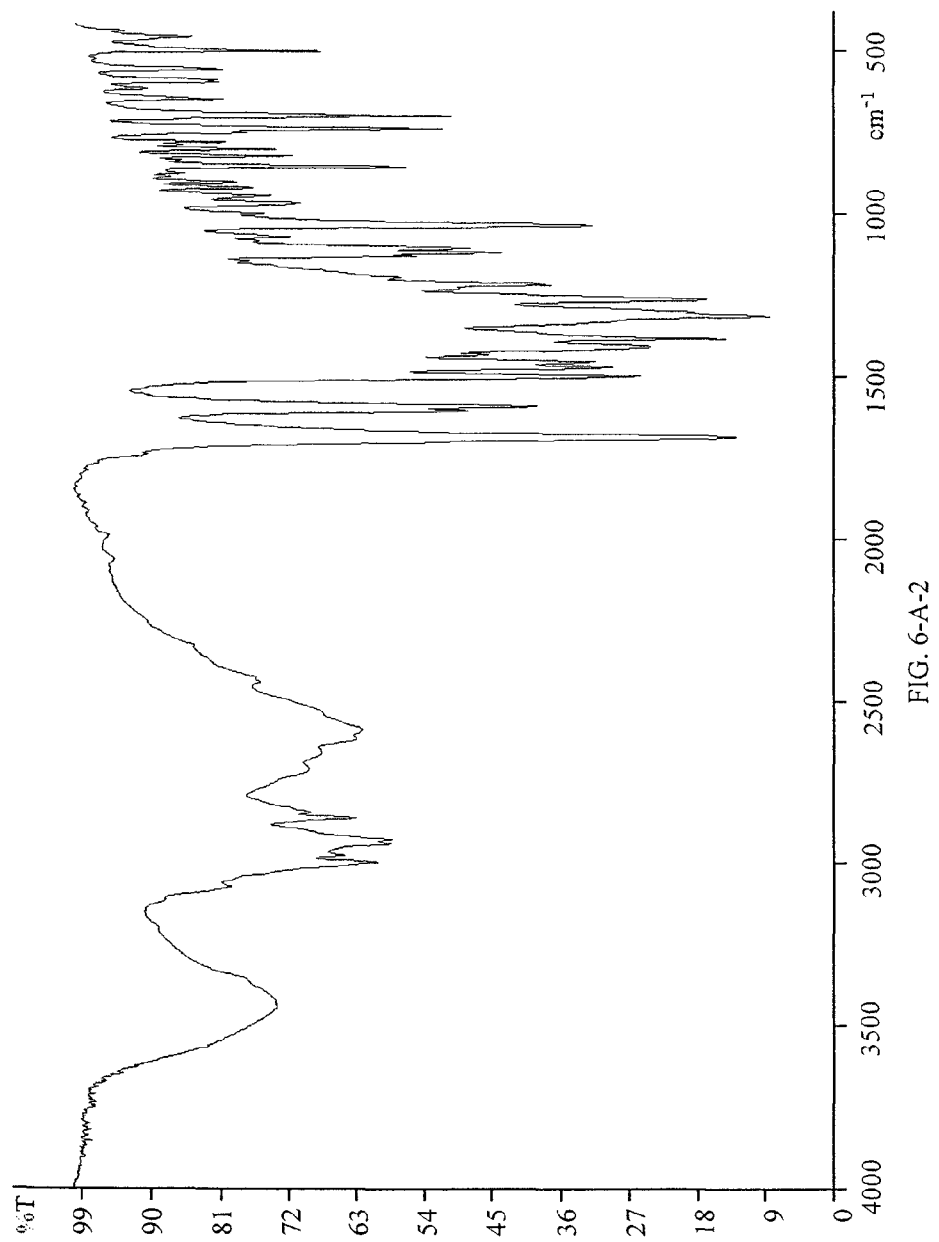
FIG. 6-A-2

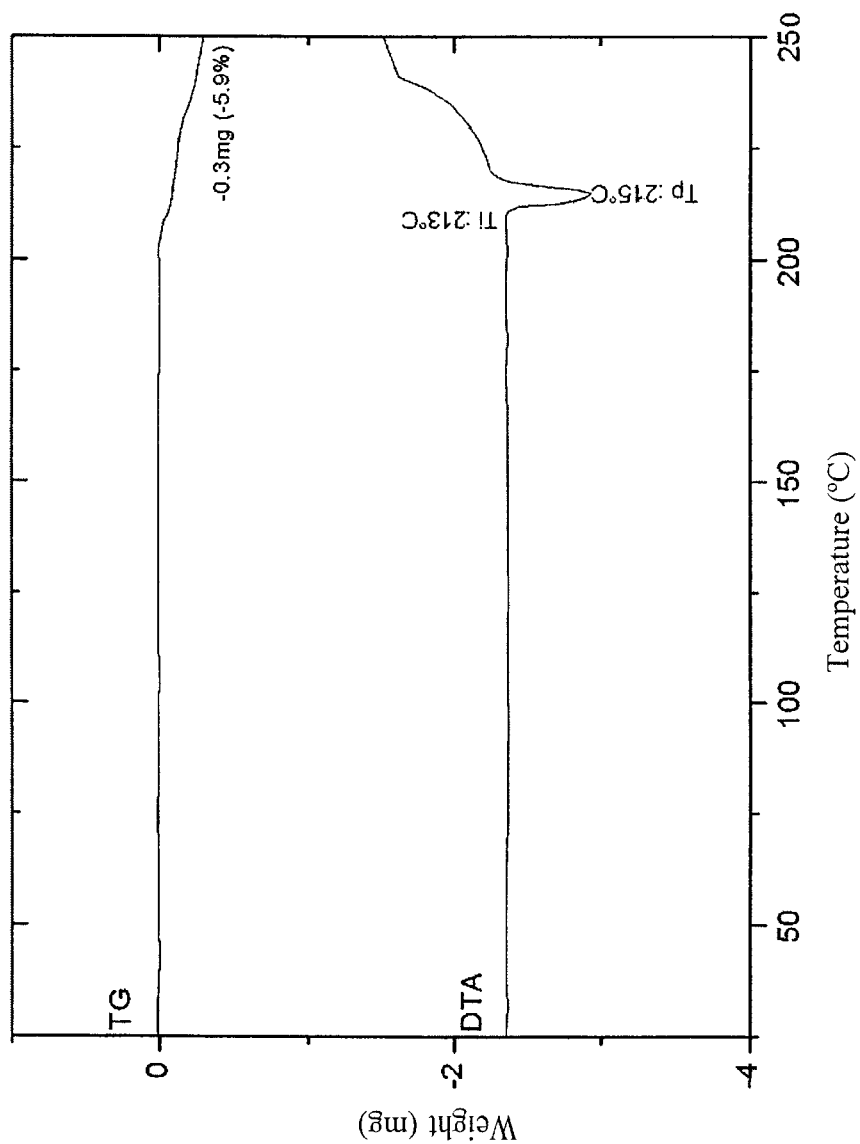
FIG. 6-A-3

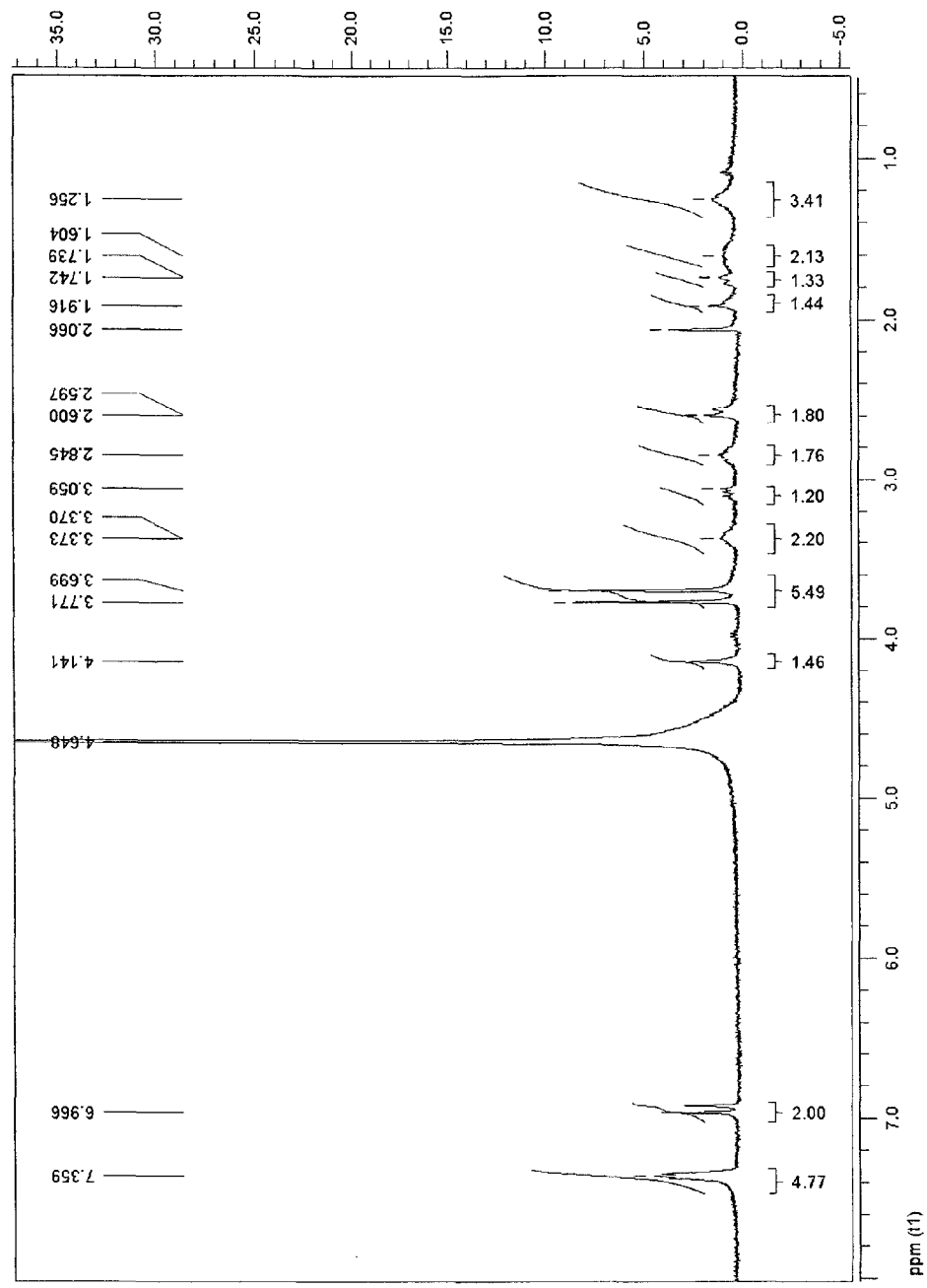
FIG. 6-A-4

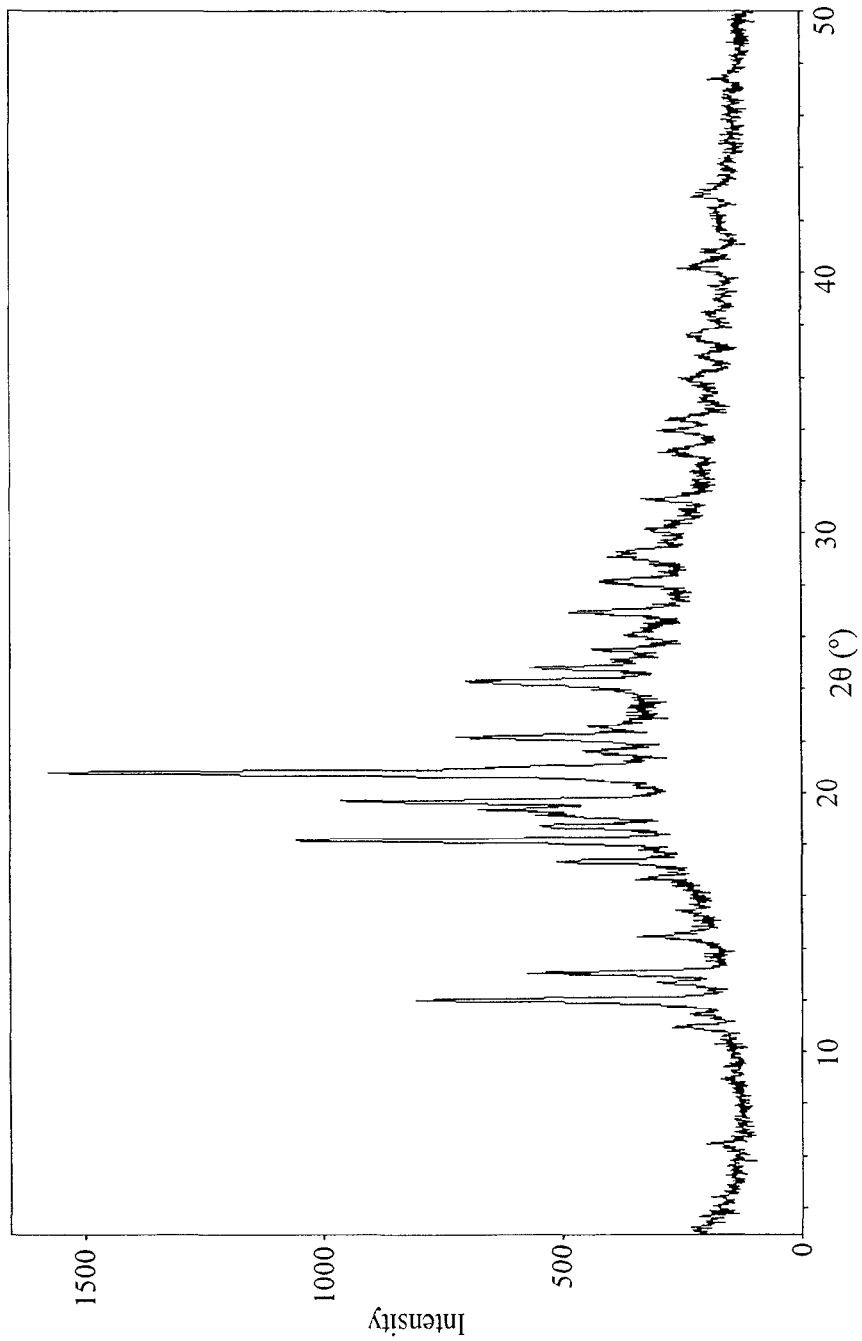
FIG. 7-A-1

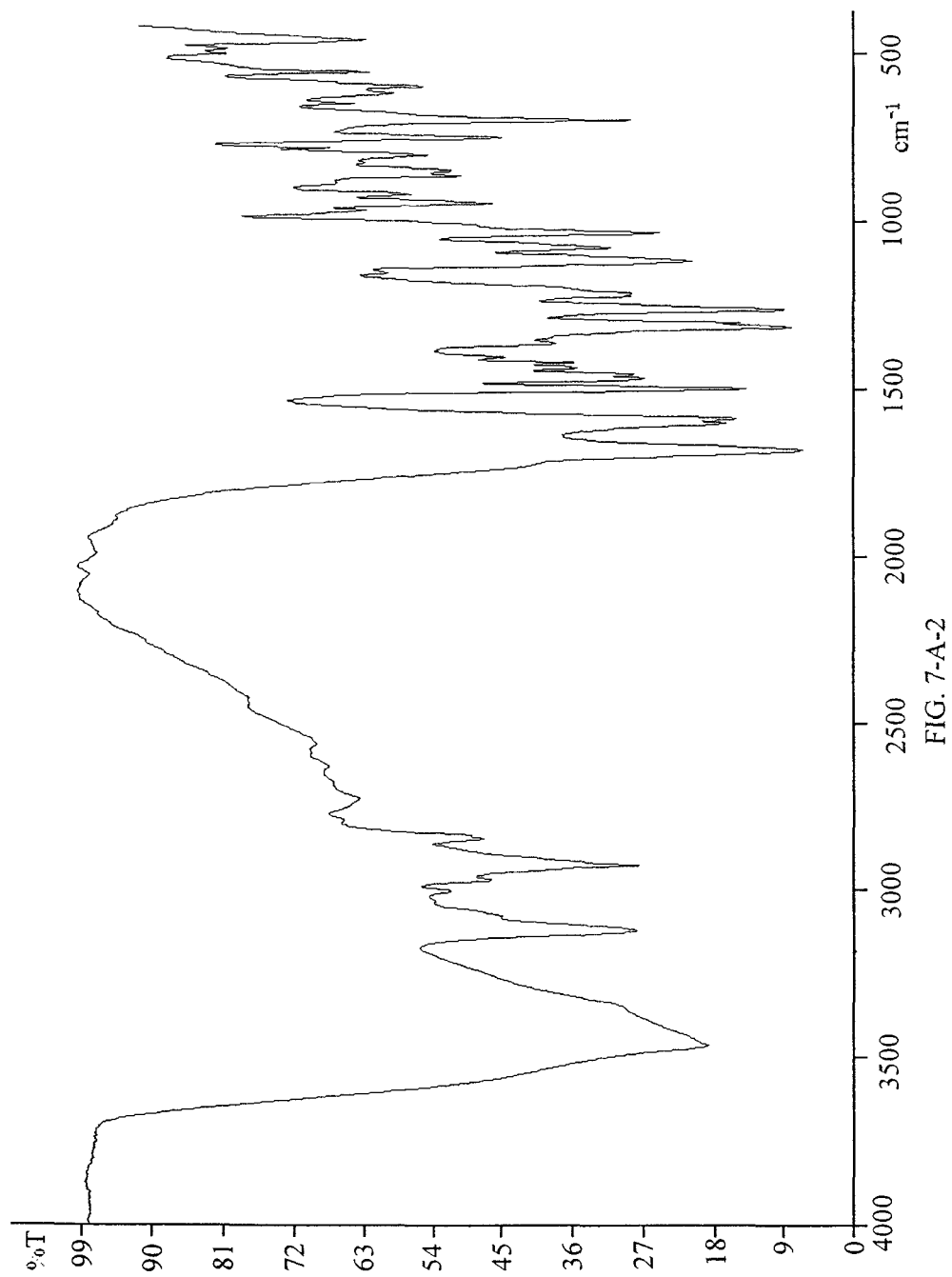
FIG. 7-A-2

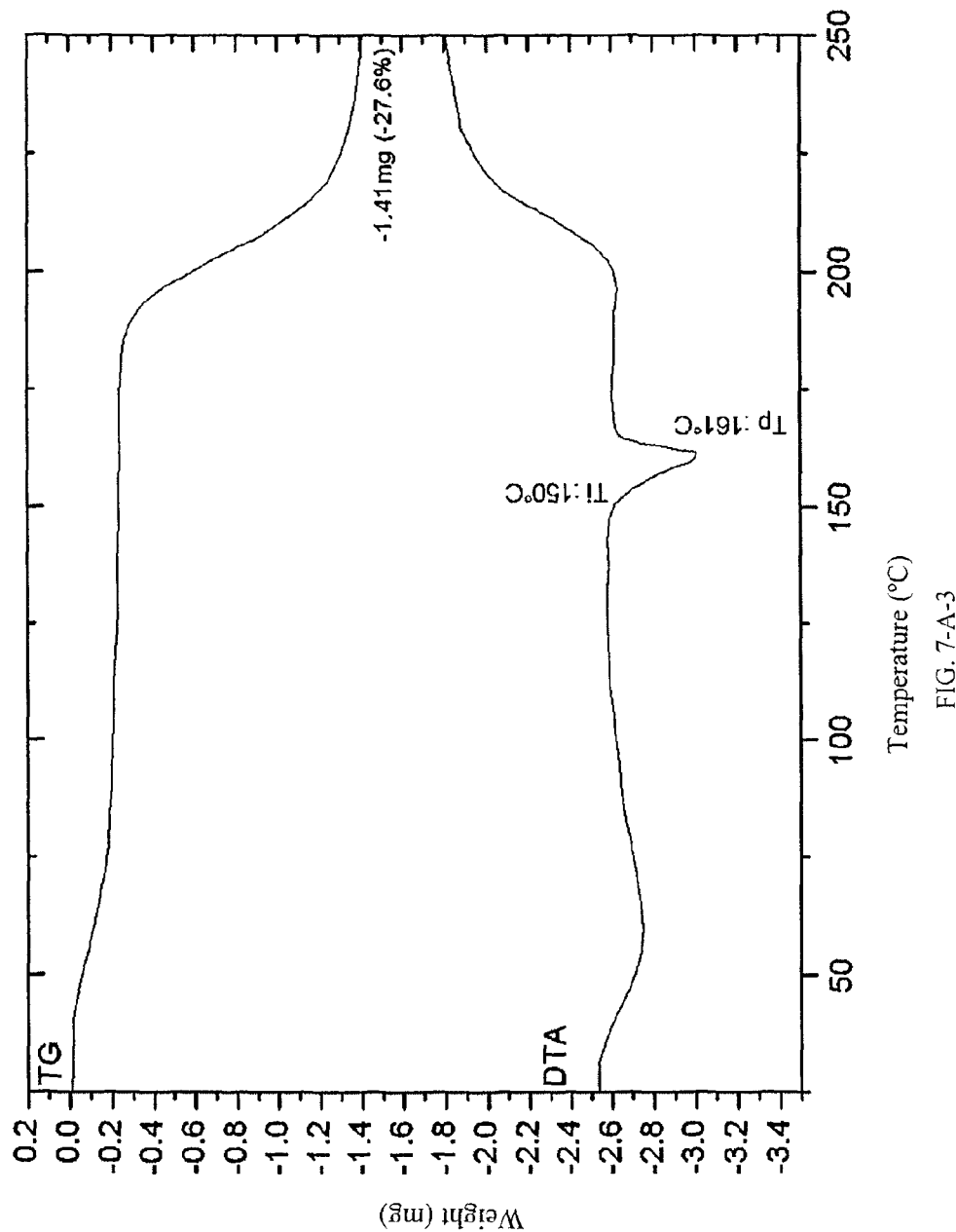
FIG. 7-A-3

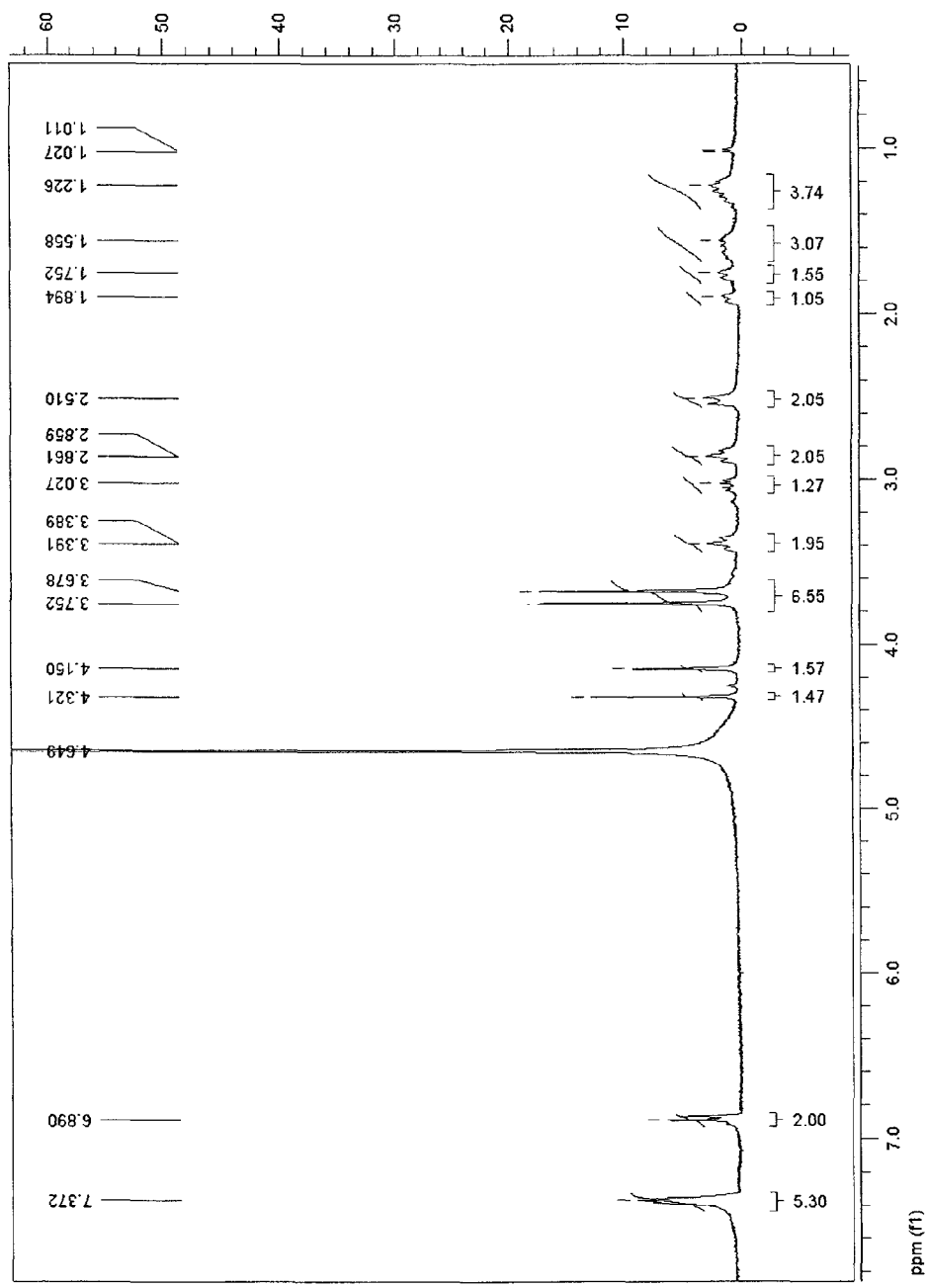
FIG. 7-A-4

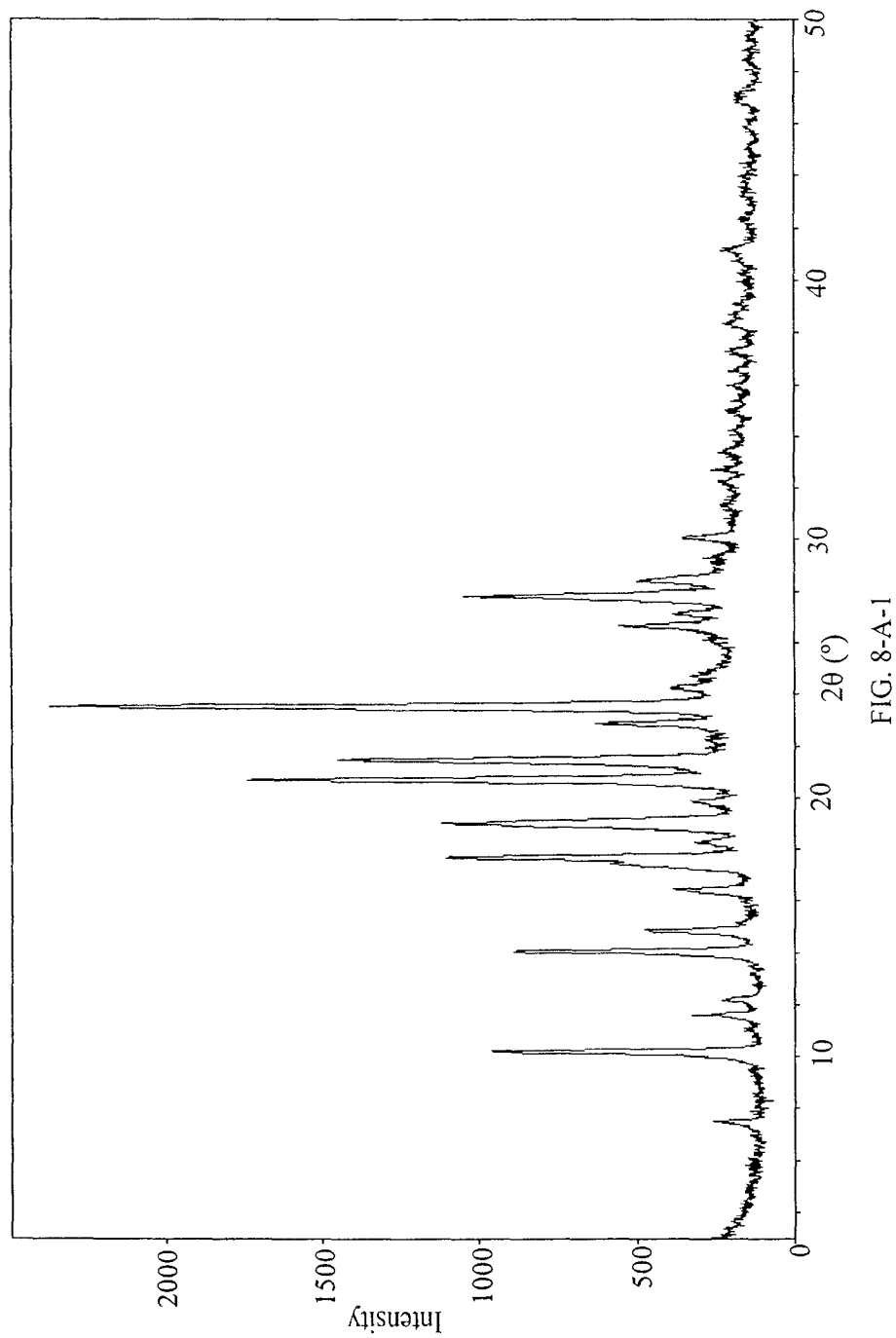
FIG. 8-A-1

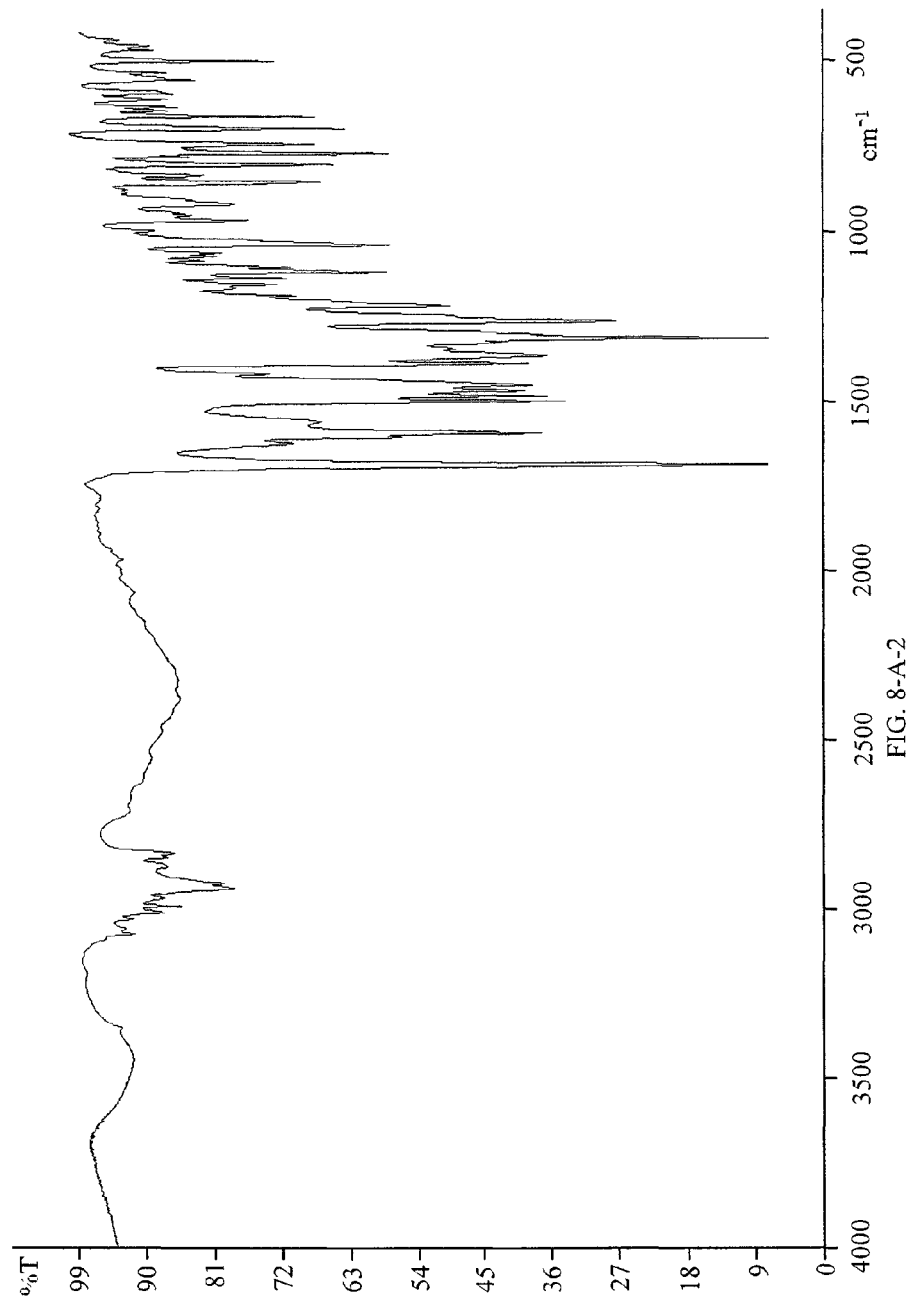
FIG. 8-A-2

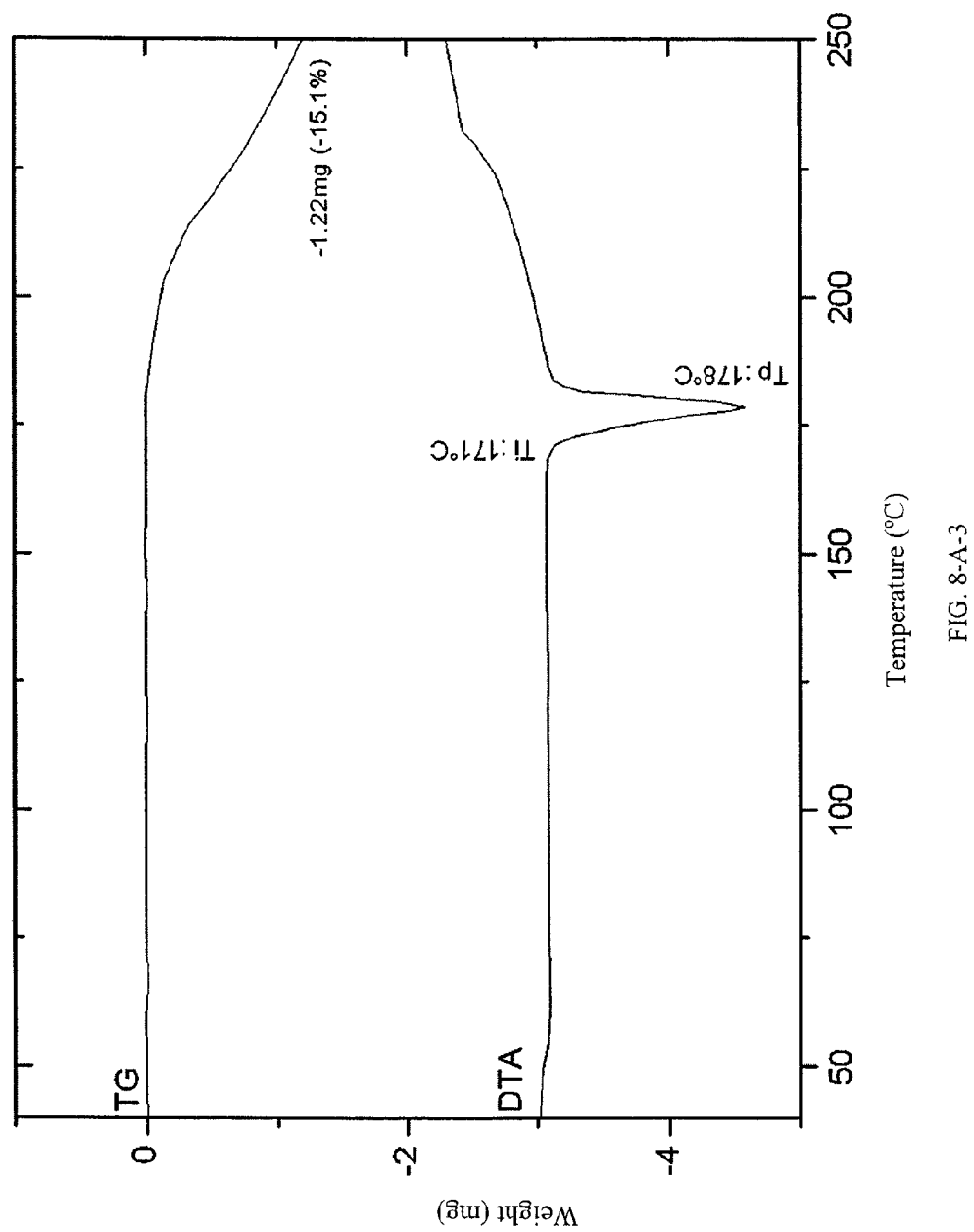
FIG. 8-A-3

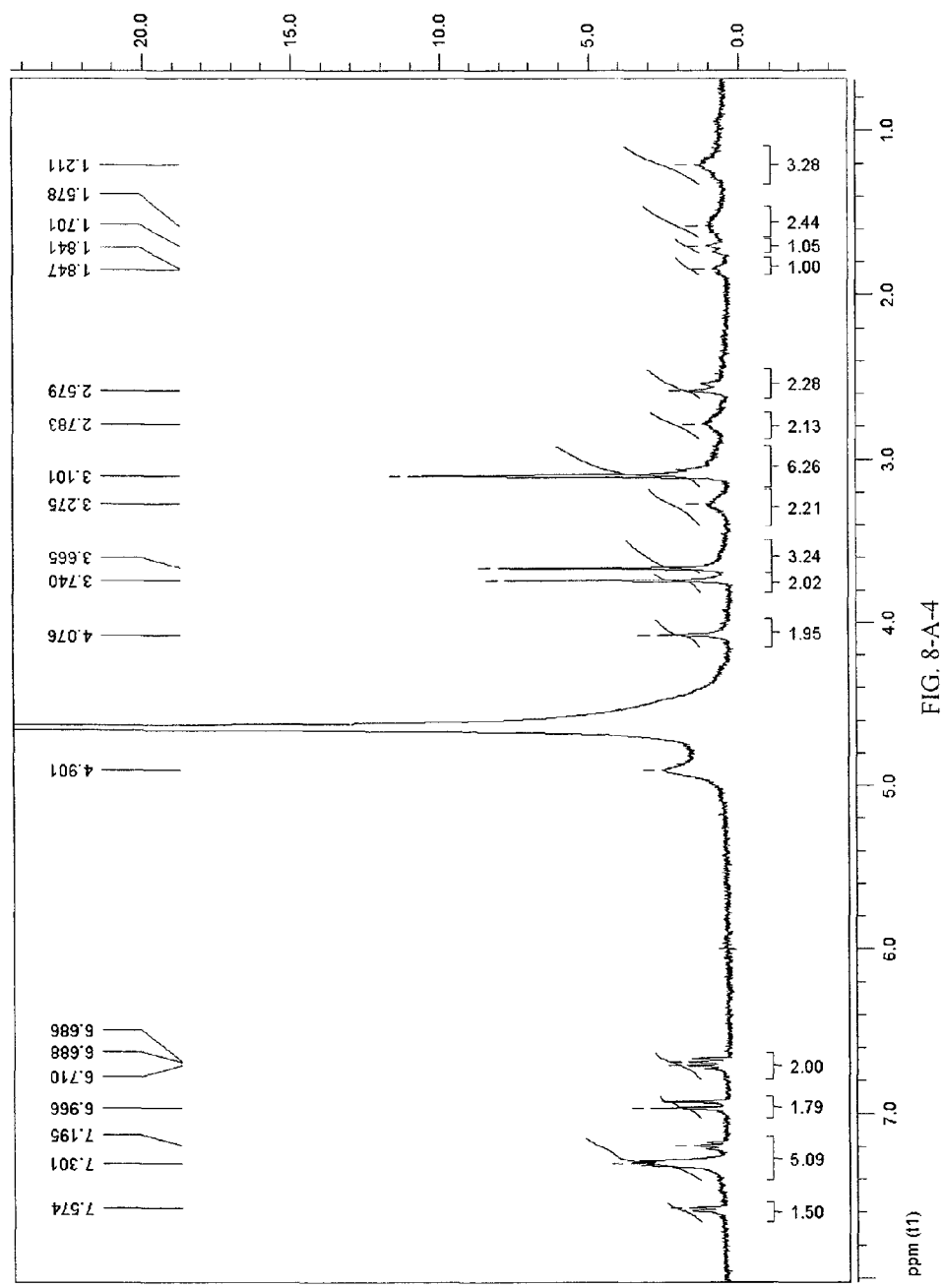
FIG. 8-A-4

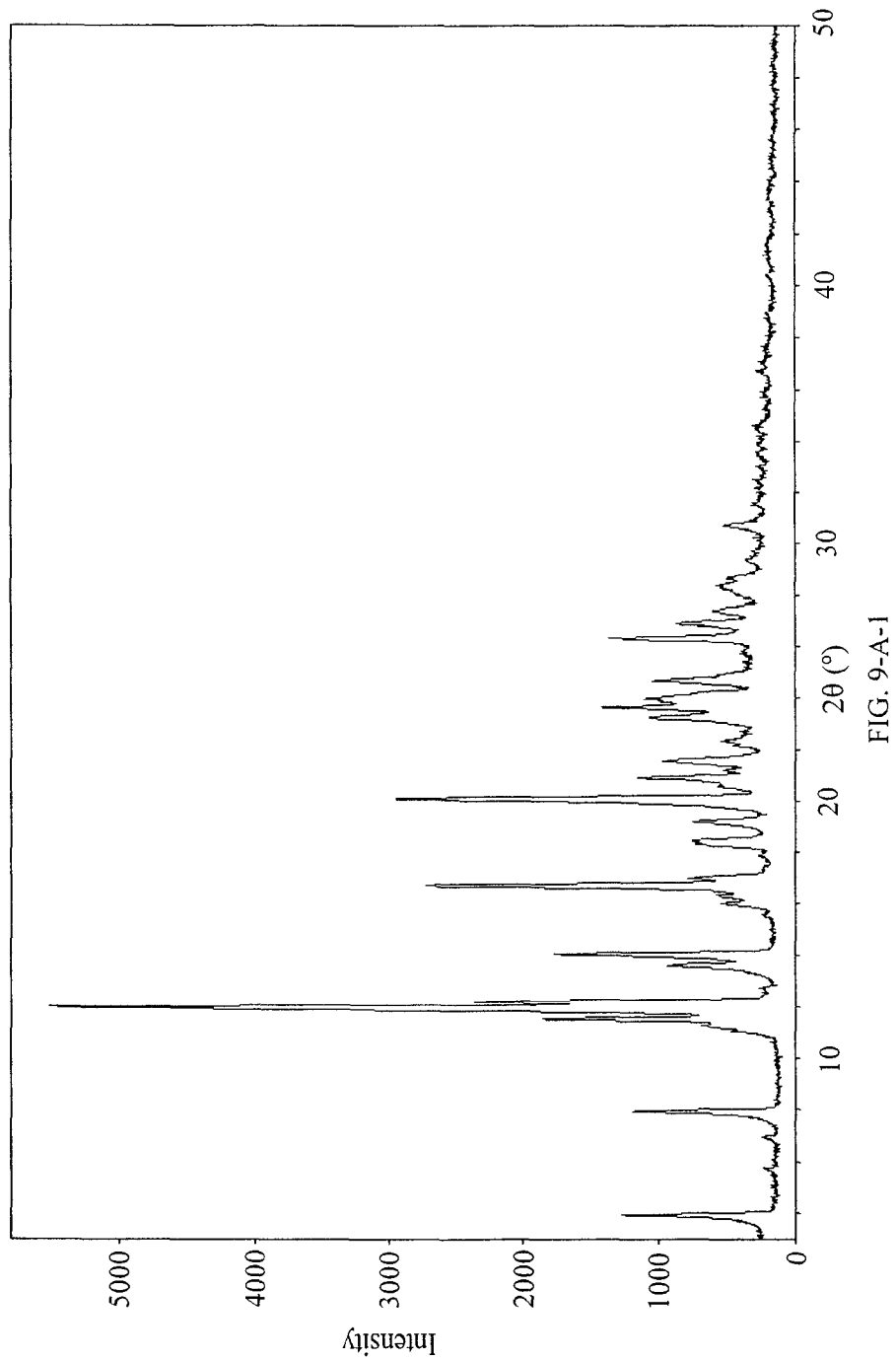
FIG. 9-A-1

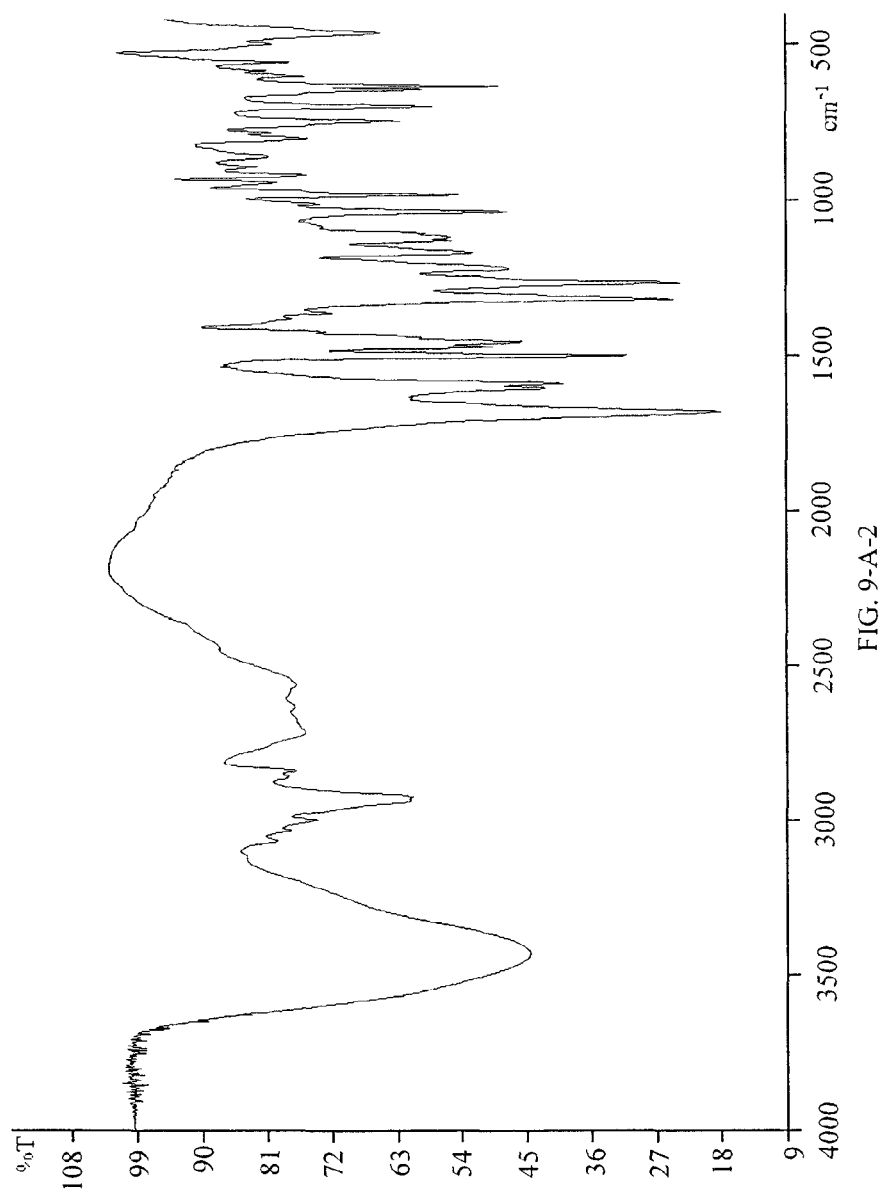
FIG. 9-A-2

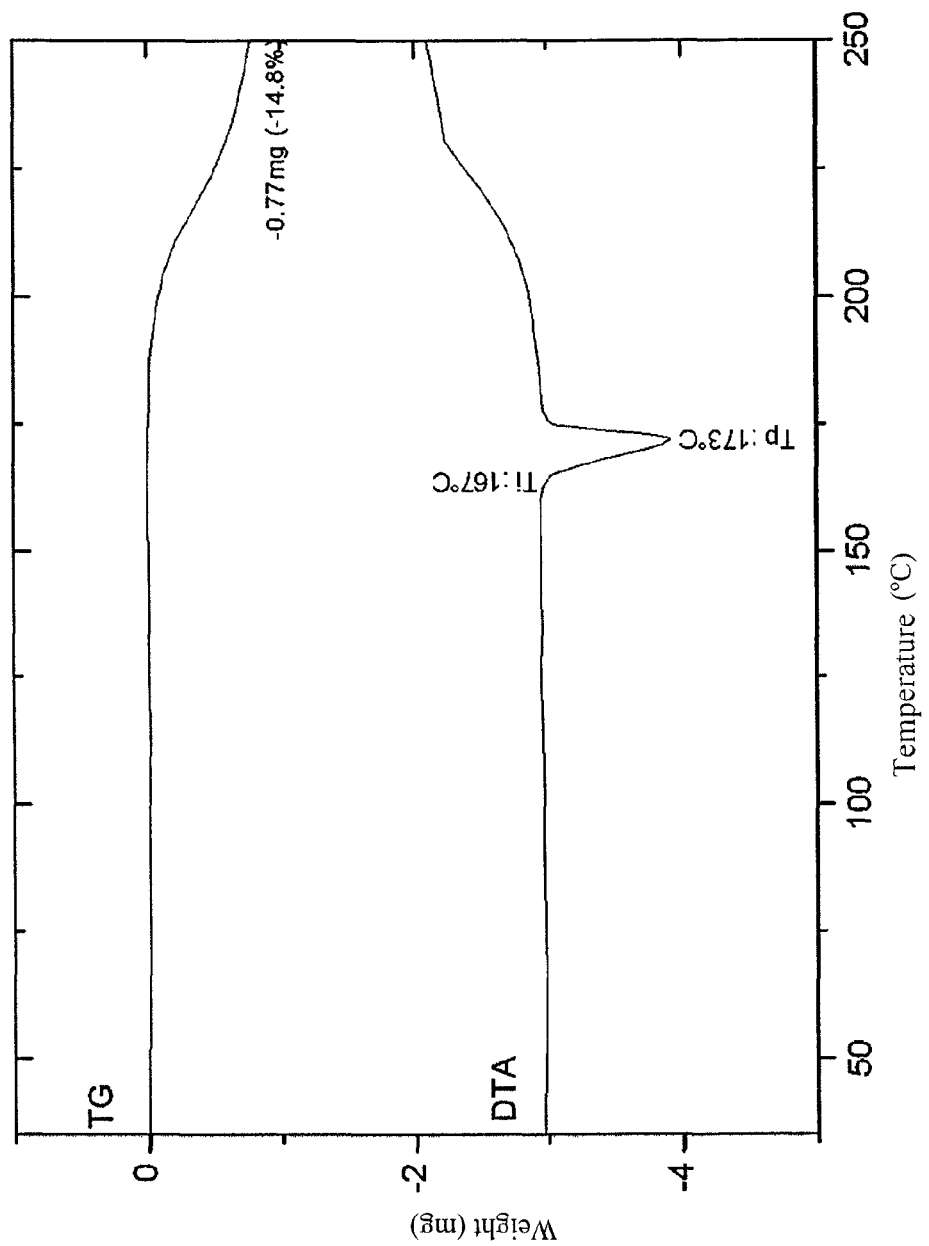
FIG. 9-A-3

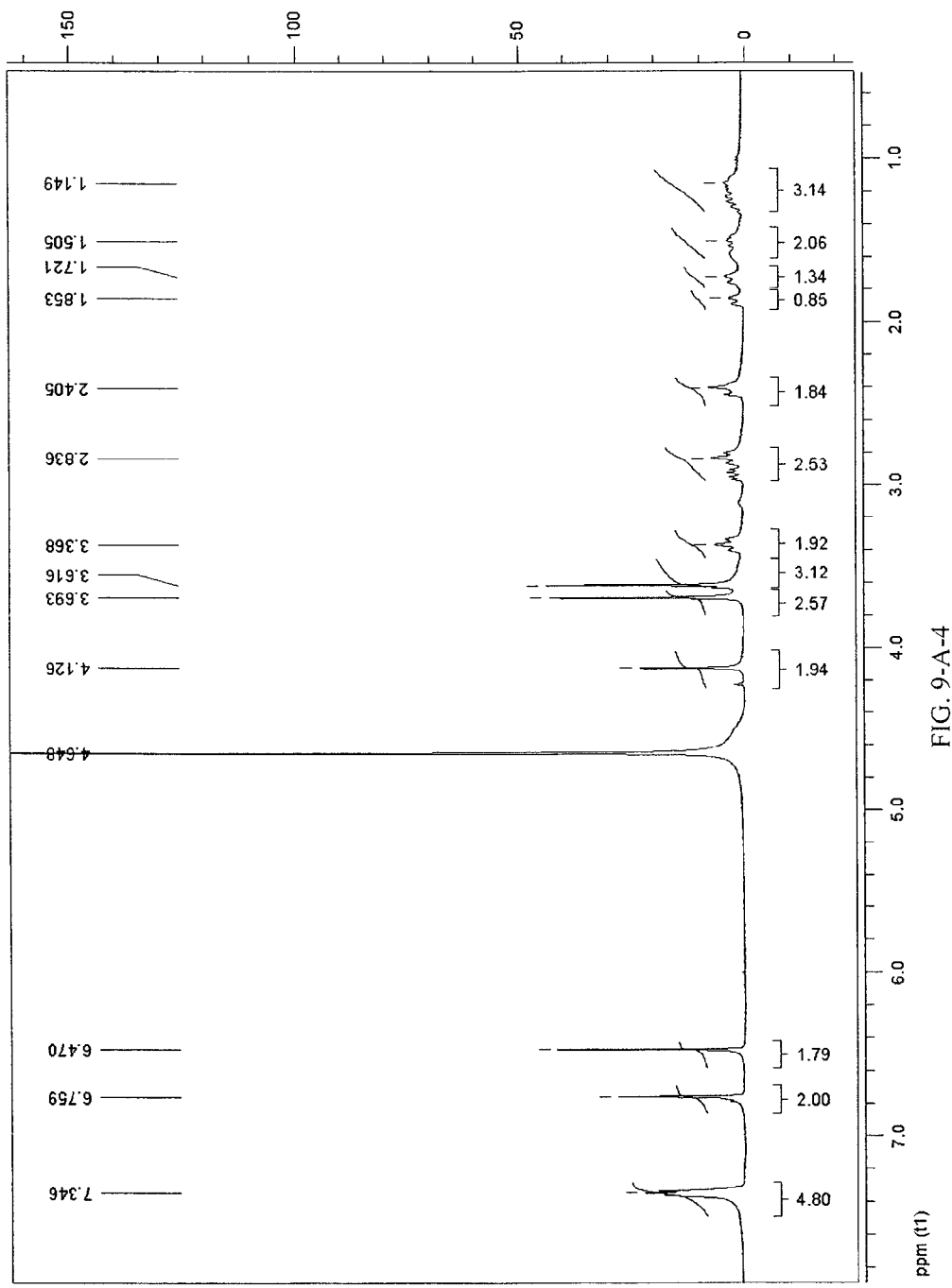
FIG. 9-A-4

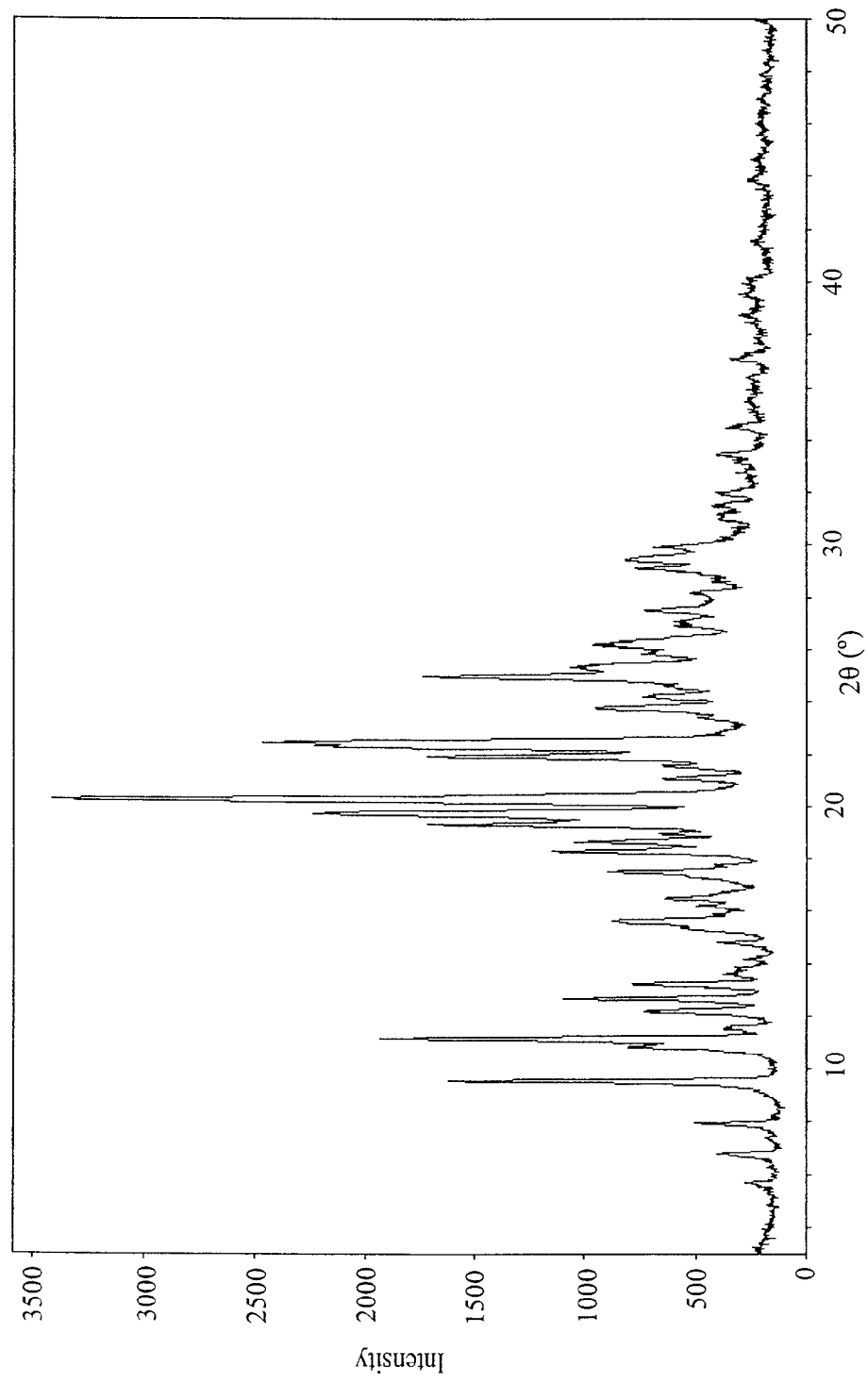
FIG. 10-A-1

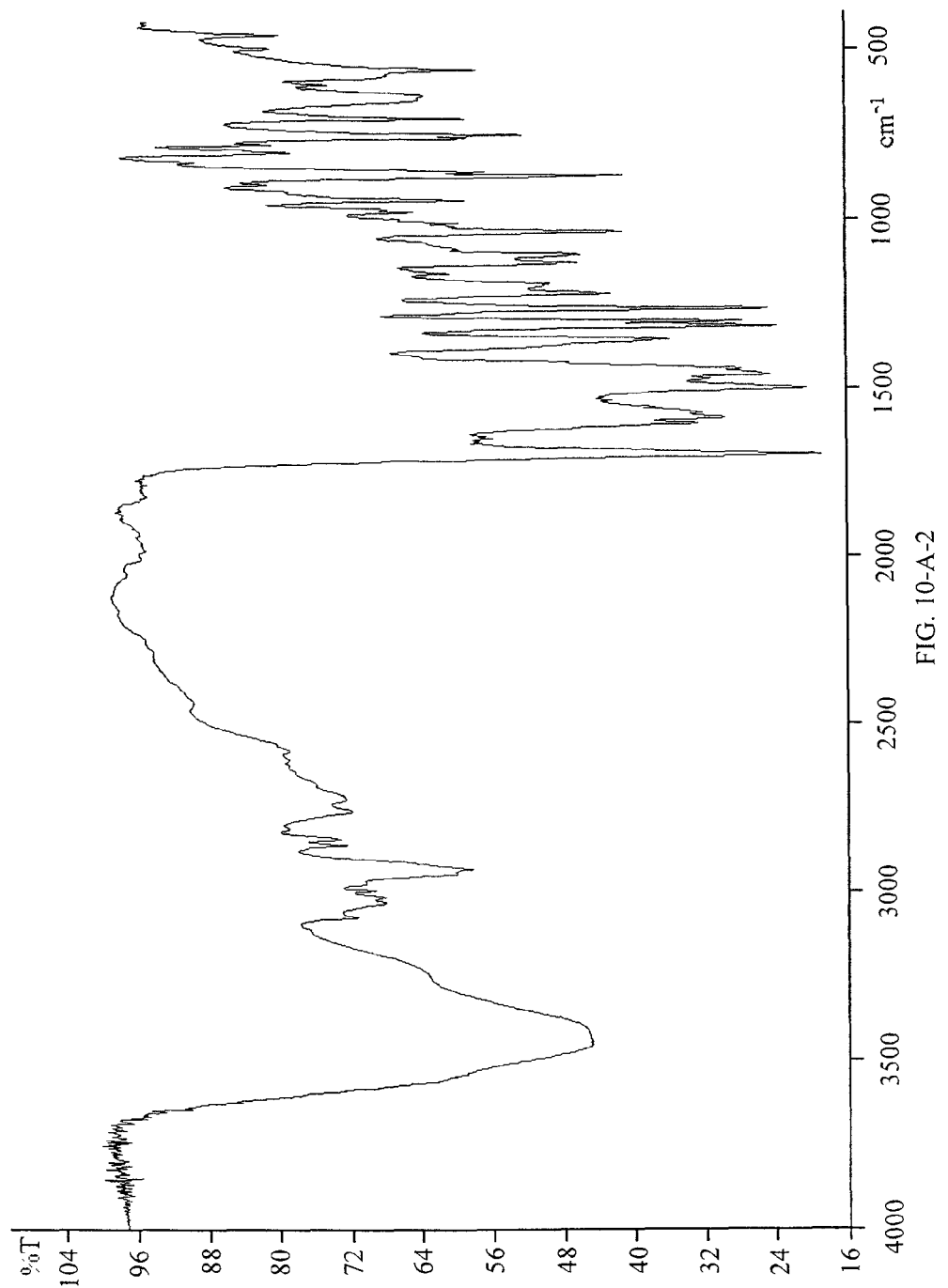
FIG. 10-A-2

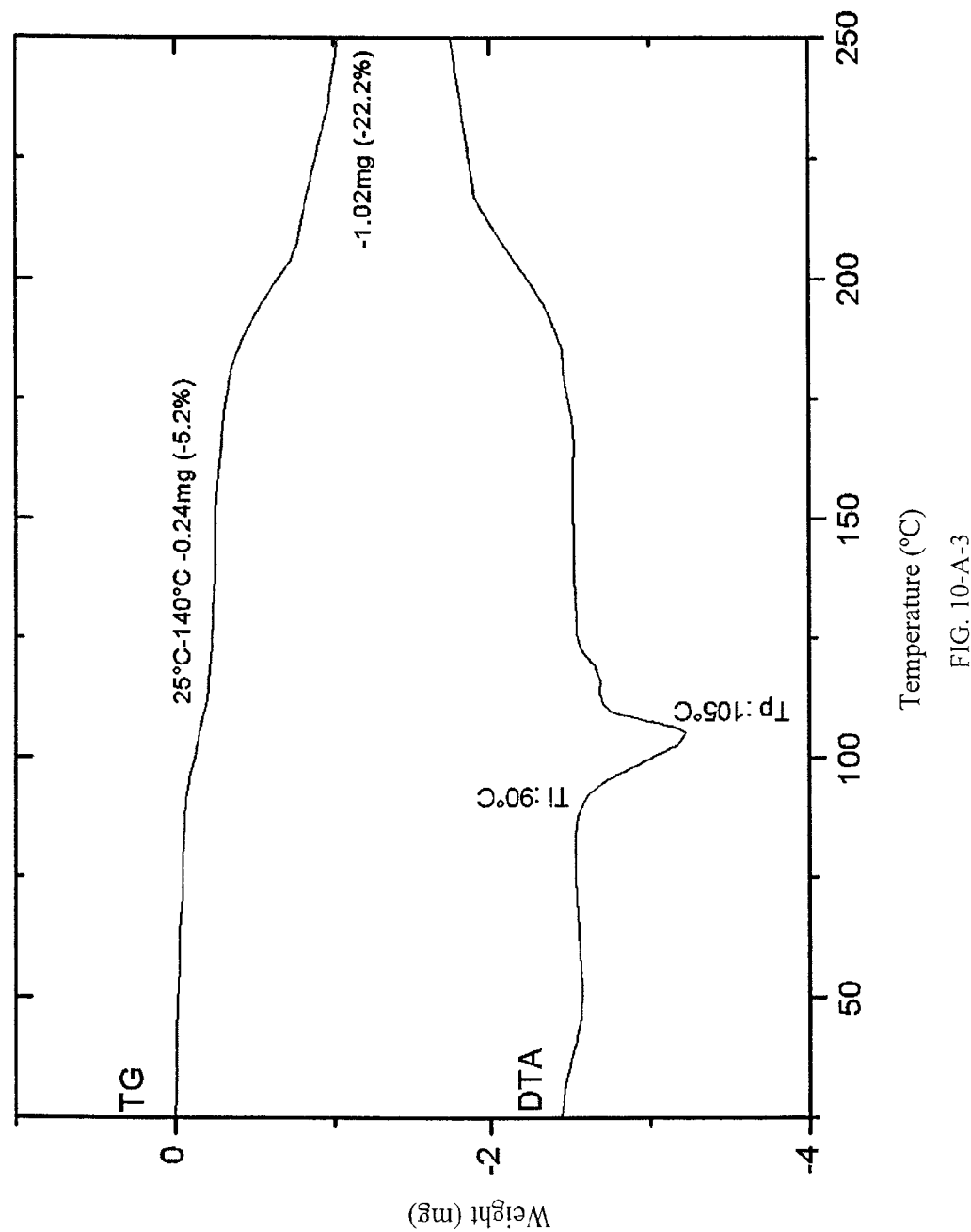
FIG. 10-A-3

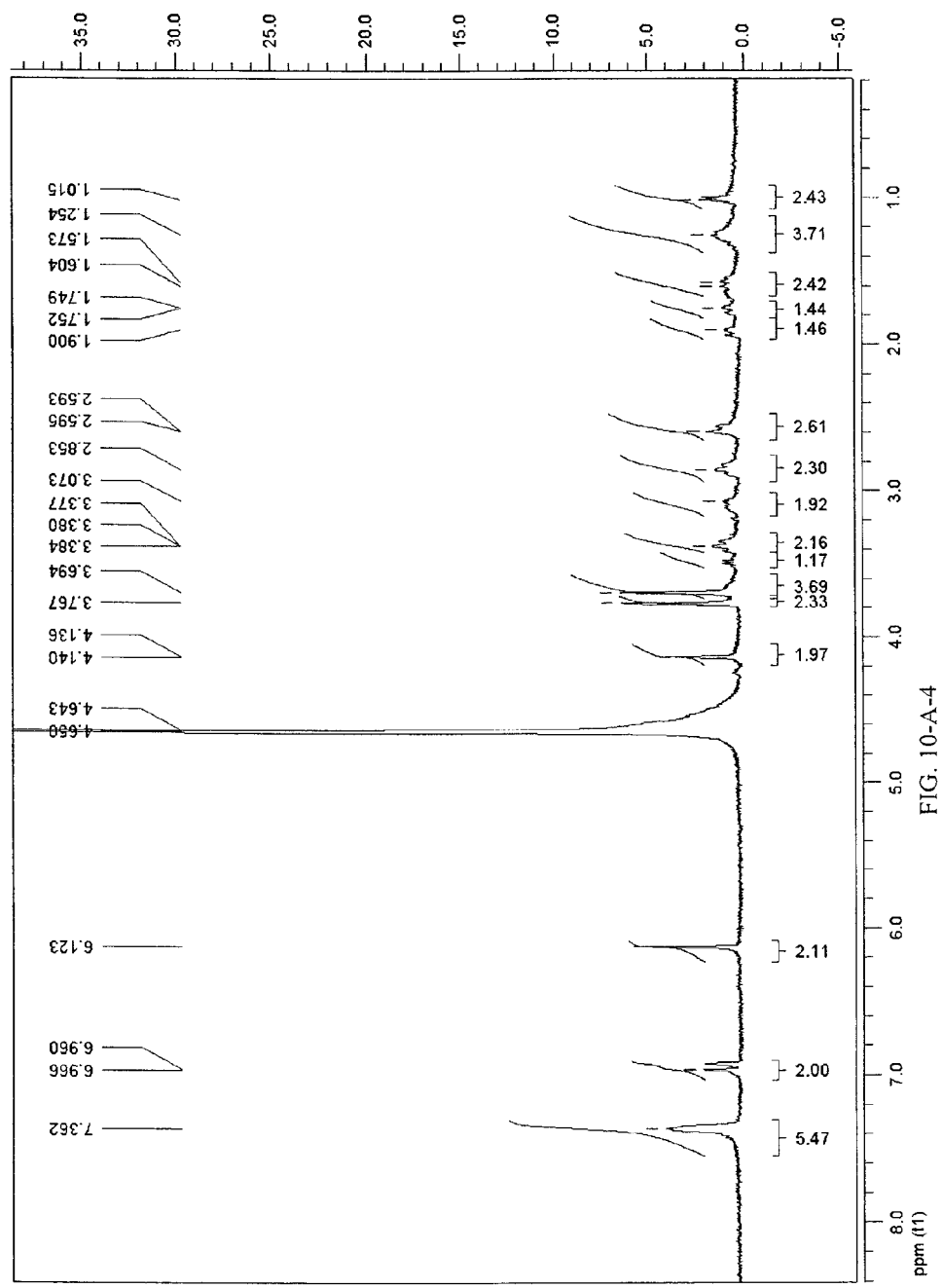
FIG. 10-A-4

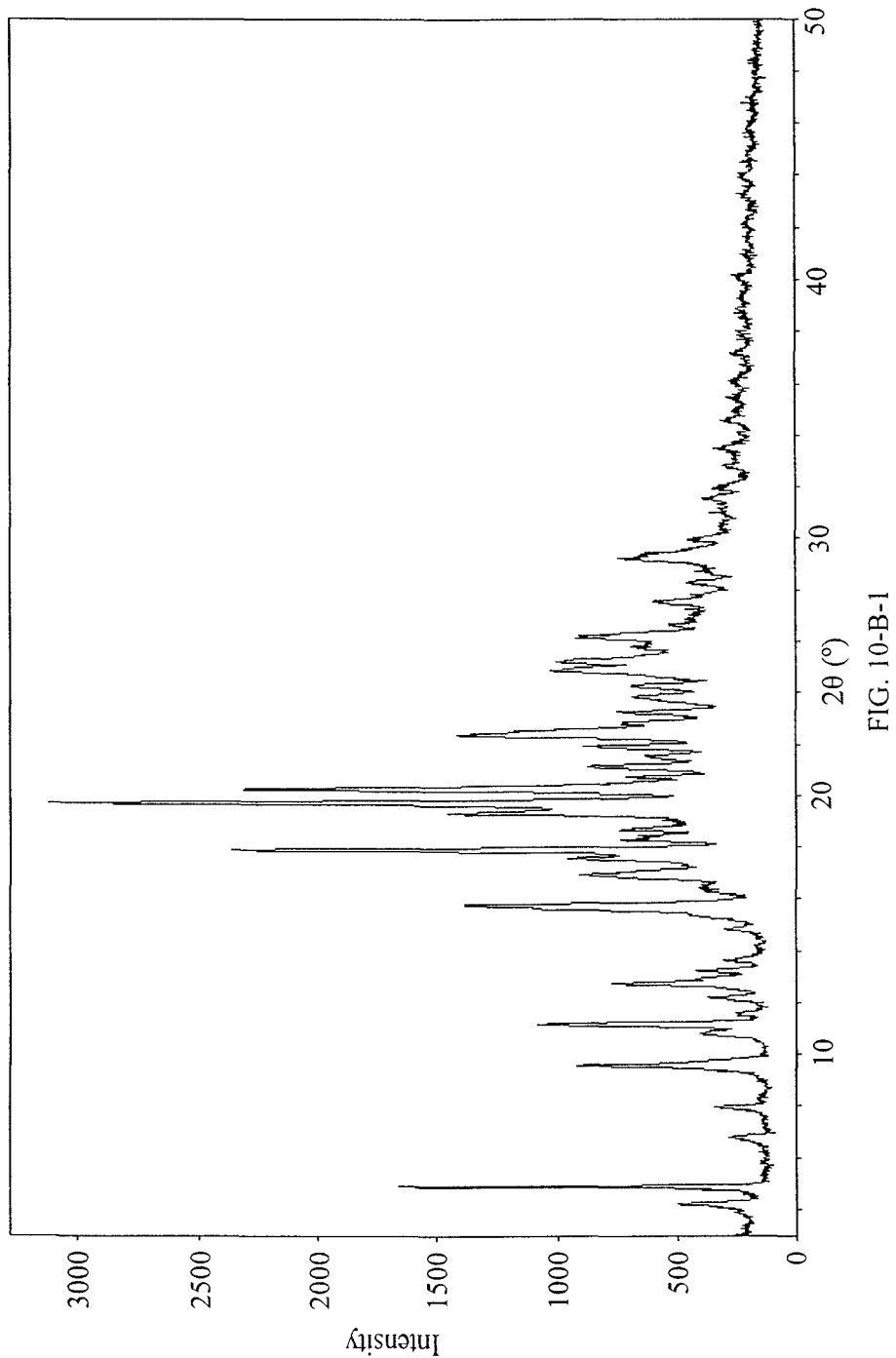
FIG. 10-B-1

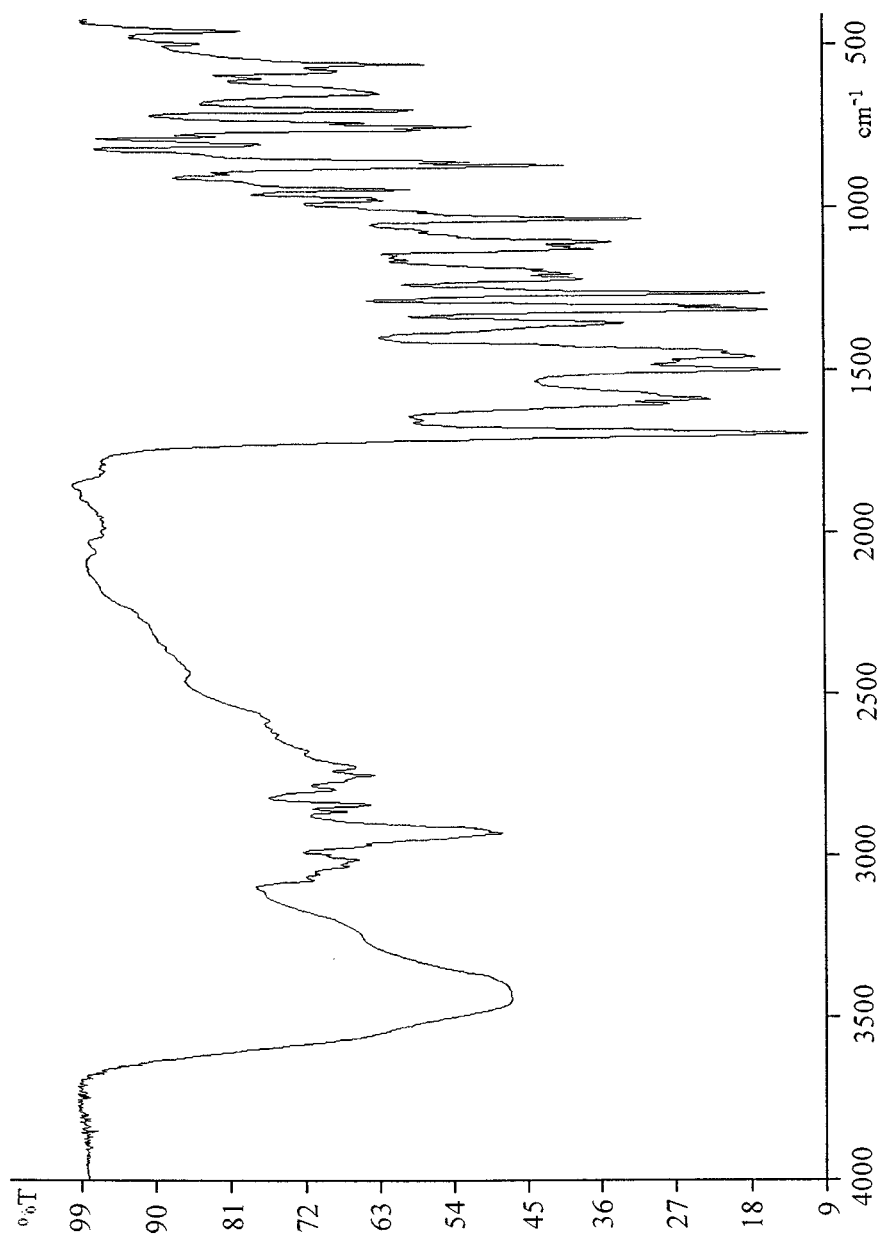
FIG. 10-B-2

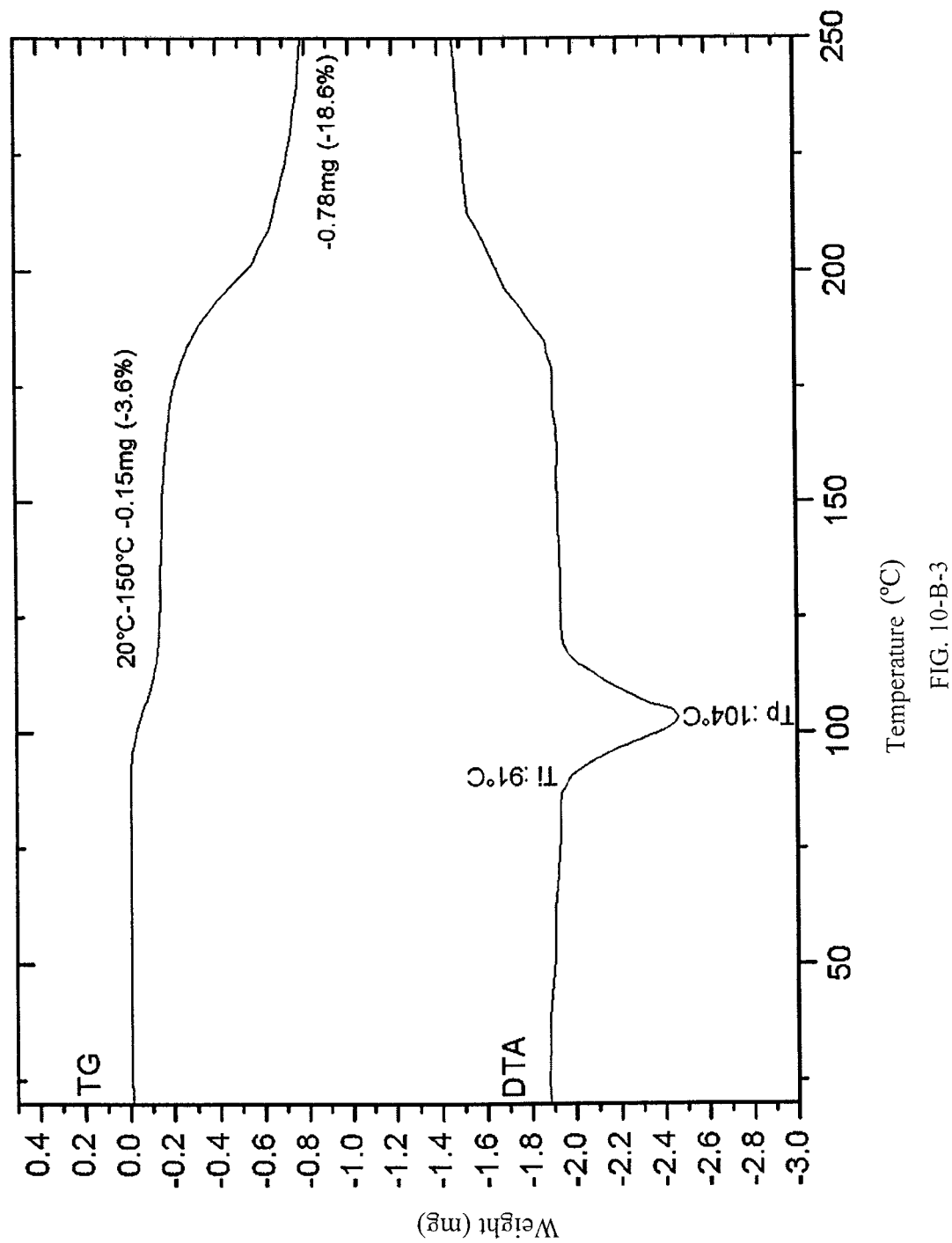
FIG. 10-B-3

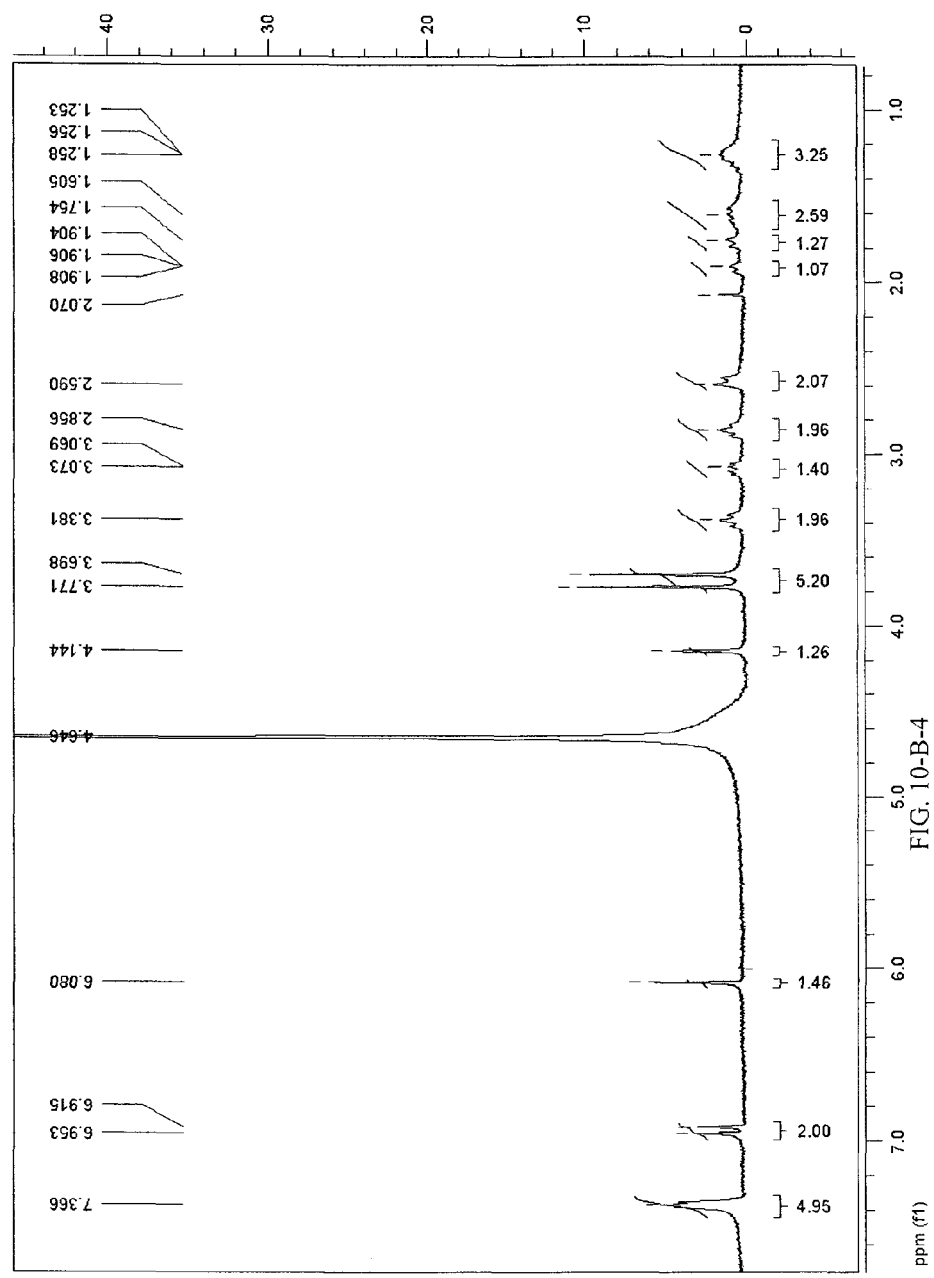
FIG. 10-B-4

POLYMORPHS OF DONEPEZIL SALTS, PREPARATION METHODS AND USES THEREOF

TECHNICAL FIELD

The present invention relates to methods for preparing a mesylate, para-toluenesulfonate, succinate, tartrate, sulphate, nitrate, phosphate, salicylate, fumarate, maleate, gallate, acetylsalicylate, benzenesulphonate, citrate, aspartate, glutaminate, lactate, gluconate, ascorbate, malonate, malate, sorbate, acetate or formate of 1-benzyl-4-[(5,6-dimethoxy-1-indanon)-2-yl]methylpiperidine (i.e., Donepezil), novel polymorphs of the salts and methods for preparing the same, and co-crystals formed from Donepezil hydrochloride and maleic acid, fumaric acid, citric acid, salicylic acid, tartaric acid or succinic acid.

TECHNICAL BACKGROUND

Donepezil hydrochloride, with a chemical name of 1-benzyl-4-[(5,6-dimethoxy-1-indanon)-2-yl]methylpiperidine hydrochloride and chemical structure:

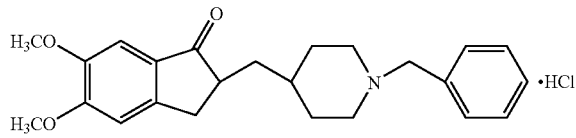

is one of the second generation of cholinesterase (ChE) inhibitors, having a long effect for treating Alzheimer's diseases (AD).

AD is an acquired decline of intelligence accompanied by other cognitive impairments and having hypomnesia as its main symptom. Research in the past thirty years has shown that the progressive degeneration of cholinergic neurons is responsible for hypomnesia, disorientation and change of behavior and personality. This cholinergic theory has been confirmed by a histological study.

Therapeutically, Donepezil can reversibly inhibit hydrolysis of acetylcholine by acetylcholinesterase (AchE) so as to increase acetylcholine at receptors, while Donepezil has a weak effect on acetylcholinesterase in peripheral tissues such as myocardial cells and blood erythrocytes. Donepezil may have other mechanisms, including treatment of peptides, direct effects on neurotransmitter receptors or $Ca^{2+}$ channels. Donepezil has a good selectivity, high bioavailability, and long half-life, and therefore can be conveniently administrated. Donepezil has an excellent tolerance in patients without hepatotoxicity. Since Donepezil has a significant efficacy on Alzheimer's diseases (AD), the market volume thereof is increasing.

Chinese patent ZL200310106920.3 describes a method for preparing Donepezil.

Japanese patent application with publication number A-64-79151 (corresponding to U.S. Pat. No. 4,895,841, EP296560) discloses some salts of Donepezil, especially Donepezil hydrochloride which has a good efficacy in the prophylaxis and treatment of senile dementia and Alzheimer's disease, and methods for the preparation thereof in industry. Chinese patent with publication number CN1874998A discloses the preparation of Donepezil oxalate and polymorphs thereof.

Senile dementia is one of the common diseases generally occurred in the elder, and is a disease involving central nervous system degeneration with progressive cognitive impairment and memory impairment, of which the main symptoms are memory disorders, decline of calculating ability, visual spatial disorientation, language disorders, decline of understanding and judging ability, mood and behavior disorders. AD patients require long-term treatment, while the Donepezil preparation currently available on the domestic market is a conventional oral preparation, which is very inconvenient for elder patients having difficulty in swallowing.

In comparison with the ordinary tablet, oral liquid, granule, buccal tablet, effervescent tablet, orally disintegrating tablet, lyophilized rapid dissolving tablet and chewable tablet are more convenient and safer for elder patients with dysphagi. Particularly, an orally disintegrating tablet has advantages including that: the tablet could rapidly disintegrate in saliva and rapidly take effect when placed on the tongue without water and chewing; the tablet can be conveniently stored; the preparation process is mature; the production cost is comparable to that of the ordinary tablet; the tablet is very convenient for the elder patients having difficulty in swallowing. In the developed countries, orally disintegrating tablets of Donepezil hydrochloride have become a major preparation.

Some references have reported methods of the preparation of Donepezil hydrochloride, hydrobromide, benzenesulfonate, oxalate, succinate, maleate and fumarate of Donepezil and novel crystal forms thereof. However, neither taste tests of the above-mentioned salts nor non-bitter salts or preparations of Donepezil have been reported to date. Donepezil hydrochloride tastes highly bitter, which cannot be masked by taste-masking agents, which results in that many patients are reluctant to take orally disintegrating tablets of Donepezil hydrochloride.

Therefore, it is highly desirable to develop non-bitter salts of Donepezil, oral liquids, granules, buccal tablets, effervescent tablets, orally disintegrating tablets, lyophilized rapid dissolving tablets and chewable tablets comprising the same.

DESCRIPTION OF THE INVENTION

The present invention discloses a compound of formula (I), solvates thereof, polymorphs thereof, polymorphs of the solvates and a method for preparing the same,

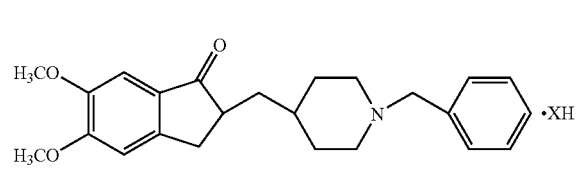

wherein XH represents methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid.

The present invention further discloses some non-bitter or slightly bitter salts of Donepezil, i.e., a compound of formula (II), and orally disintegrating tablets, oral liquids, buccal tablets, effervescent tablets, chewable tablets, granules, and lyophilized rapid dissolving tablets comprising at least one of the compound of formula (II), polymorphs and solvates thereof,

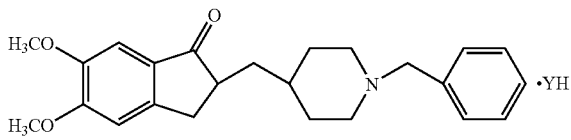 [SMILES: COc1cc2c(cc1OC)C(=O)C(CC1CCN(Cc3ccccc3)CC1)C2 ; Cl]

wherein YH represents nitric acid, salicylic acid, acetylsalicylic acid, gallic acid, or maleic acid.

A compound of formula (II) is non-bitter where YH represents nitric acid, salicylic acid, acetylsalicylic acid, or gallic acid. A compound of formula (II) is slightly bitter where YH represents maleic acid, of which the slightly bitter taste can be masked by a taste-masking agent when a pharmaceutical formulation is prepared.

The present invention further discloses complexes formed from Donepezil hydrochloride and maleic acid, fumaric acid, citric acid, salicylic acid, tartaric acid or succinic acid, i.e., the compound of formula (III), and co-crystals thereof, solvates thereof, and co-crystals of the solvates, and a method for preparing the same, and orally disintegrating tablets, oral liquids, buccal tablets, effervescent tablets, chewable tablets, granules, lyophilized rapid dissolving tablets, ordinary oral tablets, and capsules comprising at least one of the co-crystals of the compound of formula (III),

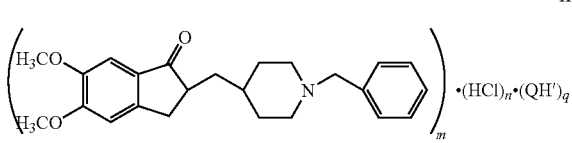

wherein QH represents maleic acid, fumaric acid, citric acid, salicylic acid, tartaric acid or succinic acid; and m:n:q=(I-10):(0.1-10):(0.1-10).

When in use, the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be in a non-solvated form or a solvated form, in particular in a hydrated form or an alcoholated form.

When in use, the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be in a form of an individual salt or a mixture of more than one kind of salt.

When in use, the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be in an amorphous form or in various crystal forms thereof, or in a form of a mixture of these forms.

When in use, the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be an enentiomer S, enentiomer R or as a mixture of enentiomer S and enentiomer R.

The present invention further discloses that unit dosage of the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid is in the range of from 0.1 mg to 50 mg; preferably in the range of from 1 mg to 30 mg; and most preferably in the range of from 2 mg to 20 mg.

The present invention further discloses that the most convenient unit dosage of the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid is equivalent to 2.5 mg, 5 mg, 10 mg, or 20 mg of Donepezil hydrochloride in mole. The most commonly used unit dosage is equivalent to 5 mg or 10 mg of Donepezil hydrochloride.

The salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be used in combination with other suitable therapeutic agents.

The salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be used in combination with suitable extracts of Chinese herbal medicines.

The salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid according to the present invention may be used in the preparation of medicaments for the treatment of diseases or physiological disorders which may be ameliorated by increasing central acetylcholine content, including but not limited to Alzheimer's disease (AD), hypomnesis, hyperkinetic syndrome of childhood, progressive cerebral atrophy and parkinson's disease.

The present invention further discloses formulations of oral liquids, granules, buccal tablets, effervescent tablets, orally disintegrating tablets, lyophilized rapid dissolving tablets, chewable tablets, ordinary oral tablets, and capsules of the salts formed from Donepezil and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid, and a method for preparing the same.

The present invention relates to a method for preparing the salts formed from Donepezil, i.e., a compound of formula (XX),

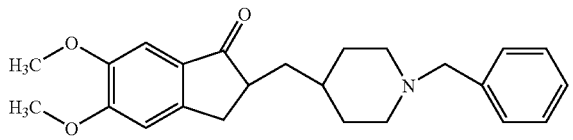

XX and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid, i.e., a compound of formula (I), or solvates of a compound of formula (I), comprising:

a) dissolving Donepezil in a suitable first solvent to form solution A;

b) dissolving a corresponding acid XH in a suitable second solvent to form solution B; and c) adding the solution A to the solution B or vice versa to form a mixed solution; and separating the salt of Donepezil (i.e., a compound of formula (I)) from the mixed solution.

The first and second solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane and mixtures thereof. The ratio of Donepezil to the acid is 1:0.2-5 (molar ratio).

The present invention further relates to polymorphs prepared from the salts formed from Donepezil, i.e., a compound of formula (XX), and methanesulfonic acid, para-toluenesulfonic acid, succinic acid, tartaric acid, salicylic acid, fumaric acid, maleic acid, gallic acid, acetylsalicylic acid, citric acid, aspartic acid, glutamic acid, lactic acid, gluconic acid, ascorbic acid, malonic acid, malic acid, sorbic acid, acetic acid, formic acid, sulfuric acid, nitric acid, phosphoric acid, or benzenesulphonic acid, or from the solvates of the above salts, and to a method for preparing the same.

The method for preparing a polymorph of the compound of formula (I) or a polymorph of a solvate of the compound of formula (I) comprises the following steps:

a) dissolving Donepezil in a suitable third solvent to form solution C;

b) dissolving a corresponding acid XH in a suitable fourth solvent to form solution D;

c) adding the solution C to the solution D or vice versa to form a mixed solution E; and e) optionally adding Ж solvent to the mixed solution E.

The third, fourth and Ж solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane and mixtures thereof. The ratio of Donepezil to the acid is 1:0.2-5 (molar ratio).

The Polymorph of the compound of formula (I) or the polymorph of the solvate of the compound of formula (I) according to the present invention may also be prepared by dissolving a salt of Donepezil in n solvent, followed by adding Ж solvent thereto to precipitate a crystal to give the polymorph of the corresponding salt of Donepezil or the polymorph of the solvate of the corresponding salt of Donepezil.

The Ω and Ж solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane and mixtures thereof.

As an extension of the present invention, substituted benzenesulphonic acids analogous to para-toluenesulfonic acid, including but not limited to methyl benzenesulphonic acid, chlorobenzenesulphonic acid, fluorobenzenesulphonic acid, nitrobenzenesulphonic acid, can also be used in the method according to the present invention to prepare corresponding salts of Donepezil, solvates of the salts of Donepezil, polymorphs of the salts of Donepezil, and polymorphs of the solvates of the salts of Donepezil.

Fourteen novel polymorphs formed are from these salts of Donepezil, which include:

one polymorph (I-A) of Donepezil mesylate (I),
one polymorph (II-A) of Donepezil paratoluenesulfonate (II),
one polymorph (III-A) of Donepezil succinate (III),
one polymorph (IV-A) of Donepezil tartrate (IV),
two polymorphs (V-A and V-B) of Donepezil sulphate (V),
one polymorph (VI-A) of Donepezil nitrate (VI),
one polymorph (VII-A) of Donepezil phosphate (VII),
one polymorph (VIII-A) of Donepezil salicylate (VIII),
one polymorph (IX-A) of Donepezil fumarate (IX),
two polymorphs (X-A and X-B) of Donepezil maleate (X),
one polymorph (XI-A) of Donepezil malate (XI), and
one polymorph (XII-A) of Donepezil benzenesulphonate (XII).

Powder X-ray Diffraction is performed under the following conditions.

| Sample Weight: | about 100 mg |
| --- | --- |
| Target: | Cu |
| Filter Disk: | monochromatic filter |
| Voltage/Current: | 40 kV/100 mA |
| Slit: | SS/DS 1°, RS 0.3 mm |
| Scan Rate: | 8°/min |

Infrared absorption is performed under the following conditions.

| Resolution: | 4 cm$^{-1}$ |
| --- | --- |
| Scanning Times: | 20 |
| Spectrum Range: | 4000-400 cm$^{-1}$ |

Thermolgravimetric analysis and differential thermal analysis (TG-DTA) are performed under the following conditions.

| Sample Weight: | about 6 mg |
| --- | --- |
| Reference: | Al$_2$O$_3$ |
| Temperature Rise Rate: | 10° C./min |
| Injection: | 0.7 second |
| Upper Limit: | 250° C. |
| Lower Limit: | Room temperature |

The melting points of the fourteen novel polymorphs according to the present invention are listed below.

The polymorph (I-A) of Donepezil mesylate (I): 179.1-182.6° C.;

The polymorph (II-A) of Donepezil paratoluenesulfonate (II): 170.3-171.0° C.;

The polymorph (III-A) of Donepezil succinate (III): 168.9-170.2° C.;

The polymorph (IV-A) of Donepezil tartrate (IV): 160.3-164.5° C.;

The polymorph (V-A) of Donepezil sulphate (V): 175.1° C.;

The polymorph (V-B) of Donepezil sulphate (V): 130.0° C.;

The polymorph (VI-A) of Donepezil nitrate (VI): 213.5-216.3° C.;

The polymorph (VII-A) of Donepezil phosphate (VII): 156.5° C.;

The polymorph (VIII-A) of Donepezil salicylate (VIIII): 174.8-175.5° C.;

The polymorph (IX-A) of Donepezil fumarate (IX): 170.0-171.8° C.;

The polymorph (X-A) of Donepezil maleate (X): 130.1-132.4° C.;

The polymorph (X-B) of Donepezil maleate (X): 131.1° C.;

The polymorph (XI-A) of Donepezil malate (XI): 142.4-144.7° C.; and

The polymorph (XII-A) of Donepezil benzenesulphonate (XII): 175.8° C.

The powder X-ray diffraction pattern and IR spectrum data of the fourteen novel polymorphs according to the present invention are as follows.

(1) The Polymorph (I-A) of Donepezil Mesylate (I)
Peaks in Powder X-ray Diffraction Pattern of I-A

| Diffranction Angel (2θ, °) | Intensity (I/I$_0$) | Diffraction Angel (2θ, °) | Intensity (I/I$_0$) |
| --- | --- | --- | --- |
| 9.68 | 55 | 20.74 | 19 |
| 11.80 | 62 | 21.20 | 30 |
| 13.76 | 13 | 22.20 | 24 |
| 14.92 | 45 | 23.16 | 25 |
| 15.28 | 16 | 23.44 | 15 |
| 15.62 | 19 | 24.90 | 13 |
| 16.70 | 18 | 25.36 | 20 |
| 19.96 | 100 | 27.68 | 13 |
| 20.42 | 23 | 28.28 | 12 |

Infrared absorption spectrum wavenumber of I-A in KBr (cm$^{-1}$): 437.8, 478.3, 543.8, 576.6, 640.3, 665.3, 721.3, 792.6, 823.5, 877.5, 904.5, 962.3, 987.4, 1074.2, 1135.9, 1184.1, 1290.2, 1351.9, 1396.2, 1486.9, 1548.6, 1633.4, 1814.7, 1874.5, 1947.8, 2028.8, 2123.3, 2215.8, 2294.9, 2462.7, 2653.6, 2807.9, 2861.9, 2989.2, 3141.5, 3708.5, 3743.2, 3814.6, 3851.2, 3897.5, 3928.3, 3988.1.

(2) The Polymorph (II-A) of Donepezil Para-Toluene-sulfonate (II)
Peaks in Powder X-Ray Diffraction Pattern of II-A

| Diffraction Angel (2θ, °) | Intensity (I/I$_0$) |
| --- | --- |
| 6.30 | 15 |
| 7.82 | 46 |
| 11.90 | 61 |
| 12.66 | 14 |
| 14.44 | 42 |
| 15.74 | 100 |
| 17.30 | 47 |
| 17.84 | 24 |
| 19.22 | 33 |
| 22.28 | 43 |
| 24.00 | 21 |
| 24.24 | 15 |
| 26.58 | 14 |
| 33.78 | 12 |

Infrared absorption spectrum wavenumber of II-A in KBr (cm$^{-1}$): 491.8, 595.9, 628.7, 725.1, 790.7, 848.5, 885.2, 946.9, 1020.2, 1068.4, 1139.7, 1193.7, 1242.0, 1282.5, 1344.2, 1390.4, 1481.1, 1548.6, 1633.4, 1770.4, 1816.6, 1866.8, 1959.4, 2024.9, 2102.1, 2260.2, 2580.3, 2636.3, 2694.1, 2798.2, 2858.0, 2958.3, 3155.0, 3708.5, 3741.3, 3799.1, 3851.2, 3878.2, 3939.9, 3988.1.

(3) The Polymorph (III-A) of Donepezil Succinate (III)
Infrared absorption spectrum wavenumber of III-A in KBr (cm$^{-1}$): 532.3, 572.8, 669.2, 717.4, 773.3, 819.6, 877.5, 935.3, 960.4, 997.0, 1053.0, 1141.7, 1186.0, 1232.3, 1294.0, 1353.8, 1411.7, 1483.0, 1535.1, 1641.2, 2183.1, 2615.0, 2688.3, 2815.6, 2850.3, 2877.3, 2985.3, 3052.8, 3147.3, 3698.9.

Peaks in Powder X-Ray Diffraction Pattern of III-A

| Diffraction Angel (2θ, °) | Intensity (I/I$_0$) |
| --- | --- |
| 3.96 | 21 |
| 7.96 | 22 |
| 11.24 | 11 |

-continued

| Diffraction Angel (2θ, °) | Intensity (I/I₀) |
|---|---|
| 11.56 | 34 |
| 11.98 | 100 |
| 12.22 | 46 |
| 13.64 | 16 |
| 14.04 | 32 |
| 16.74 | 37 |
| 17.02 | 10 |
| 18.48 | 12 |
| 19.20 | 11 |
| 20.08 | 39 |
| 20.92 | 16 |
| 21.54 | 13 |
| 23.26 | 14 |
| 23.66 | 21 |
| 24.04 | 16 |
| 24.70 | 18 |
| 26.32 | 16 |

(4) The polymorph (IV-A) of Donepezil tartrate (IV)
Peaks in Powder X-Ray Diffraction Pattern of IV-A

| Diffraction Angel (2θ, °) | Intensity (I/I₀) |
|---|---|
| 12.10 | 41 |
| 13.18 | 26 |
| 14.58 | 11 |
| 17.46 | 19 |
| 18.26 | 55 |
| 18.80 | 14 |
| 19.32 | 25 |
| 19.78 | 47 |
| 20.92 | 100 |
| 22.22 | 29 |
| 24.36 | 30 |
| 24.92 | 16 |
| 27.04 | 19 |
| 28.18 | 16 |
| 29.20 | 11 |

Infrared absorption spectrum wavenumber of IV-A in KBr (cm$^{-1}$): 513.0, 572.8, 642.2. 738.6, 773.3, 833.1, 896.8, 987.4, 1053.0, 1095.4, 1162.9, 1238.1, 1286.3, 1353.8, 1376.9, 1446.4, 1483.0, 1537.0, 1631.5, 1951.6, 2036.5, 2140.6, 2179.2, 2597.7, 2649.8, 2777.0, 2804.0, 2863.8, 2989.2, 3018.1, 3166.6, 3388.4, 3716.2, 3793.4, 3847.4, 3878.2, 3939.9, 3988.1.

| Diffraction Angel (2θ, °) | Intensity (I/I₀) |
|---|---|
| 10.30 | 27 |
| 14.10 | 43 |
| 14.88 | 19 |
| 17.50 | 14 |
| 17.76 | 42 |
| 18.98 | 28 |
| 20.76 | 64 |
| 21.52 | 43 |
| 22.94 | 16 |
| 23.60 | 100 |
| 27.88 | 29 |
| 28.52 | 12 |

Infrared absorption spectrum wavenumber of the polymorph (V-A) of Donepezil sulphate (V) in KBr (cm$^{-1}$): 493.7, 636.4, 667.3, 723.2, 775.3, 875.5, 908.3, 933.4, 989.3, 1091.5, 1137.8, 1199.5, 1288.2, 1392.4, 1483.0, 1548.6, 1621.9, 1874.5, 1940.1, 2001.8, 2028.8, 2094.3, 2572.6, 2605.4, 2647.8, 2678.7, 2742.3, 2775.1, 2869.6, 2985.3, 3025.8, 3164.7, 3729.7, 3776.0, 3812.6, 3851.2, 3878.2.

Peaks in Powder X-Ray Diffraction Pattern of the Polymorph (V-B) of Donepezil Sulphate (V)

| Diffraction Angel (2θ, °) | Intensity (I/I₀) |
|---|---|
| 9.34 | 12 |
| 9.56 | 23 |
| 10.26 | 29 |
| 11.66 | 23 |
| 12.14 | 15 |
| 13.42 | 14 |
| 16.48 | 100 |
| 17.04 | 11 |
| 17.56 | 36 |
| 19.08 | 26 |
| 19.82 | 28 |
| 20.88 | 21 |
| 21.24 | 53 |
| 21.66 | 23 |
| 22.94 | 16 |
| 23.52 | 13 |
| 23.98 | 39 |
| 24.28 | 27 |
| 24.84 | 25 |
| 27.06 | 11 |

Infrared absorption spectrum wavenumber of the polymorph (V-B) of Donepezil sulphate (V) in KBr (cm$^{-1}$): 474.4, 511.1, 638.3, 667.3, 719.3, 773.3, 904.5, 946.9, 983.5, 1076.1, 1135.9, 1197.6, 1288.2, 1394.3, 1436.7, 1483.0, 1546.7, 1625.7, 1805.1, 1862.9, 1938.1, 2001.8, 2028.8, 2094.3, 2607.3, 2703.8, 2771.3, 2869.6, 2975.7, 3027.7, 3263.0, 3704.6, 3772.1, 3845.4, 3876.3, 3911.0, 3953.4, 3992.0.

(6) The Polymorph (VI-A) of Donepezil Nitrate (VI)
Infrared absorption spectrum wavenumber of VI-A in KBr (cm$^{-1}$): 478.3, 522.6, 574.7, 630.6, 665.3, 721.3, 771.4, 815.8, 896.8, 933.4, 987.4, 1054.9, 1141.7, 1238.1, 1280.5, 1351.9, 1394.3, 1442.5, 1486.9, 1546.7, 1629.6, 1805.1, 1851.4, 2028.8, 2082.8, 2456.9, 2642.0, 2690.3, 2792.5, 2883.1, 2987.2, 3151.2, 3716.2, 3791.4, 3845.4, 3876.3, 3997.8.

Peaks in Powder X-Ray Diffraction Pattern of VI-A

| Diffraction Angel (2θ, °) | Intensity (I/I₀) |
|---|---|
| 6.34 | 14 |
| 10.00 | 63 |
| 12.08 | 35 |
| 12.78 | 45 |
| 13.64 | 16 |
| 16.12 | 15 |
| 17.14 | 100 |
| 18.74 | 10 |
| 19.28 | 16 |
| 19.98 | 24 |
| 20.24 | 33 |
| 21.32 | 12 |
| 21.88 | 16 |
| 22.46 | 63 |
| 22.98 | 42 |
| 23.76 | 26 |
| 24.26 | 36 |
| 27.62 | 36 |

(7) The Polymorph (VII-a) of Donepezil Phosphate (VII)
Infrared absorption spectrum wavenumber of VII-A in KBr (cm$^{-1}$): 480.2, 518.8, 570.8, 661.5, 736.7, 775.3, 833.1, 900.6, 987.4, 1053.0, 1093.5, 1162.9, 1238.1, 1288.2, 1388.5, 1446.4, 1483.0, 1535.1, 1637.3, 1947.8, 2032.6, 2105.9, 2580.3, 2649.8, 2773.2, 2863.8, 2989.2, 3022.0, 3176.2, 3847.4, 3876.3, 3988.1.

| Diffraction Angel (2θ, °) | Intensity (I/I₀) |
|---|---|
| 12.00 | 50 |
| 13.06 | 32 |
| 14.48 | 13 |
| 17.38 | 19 |
| 18.18 | 60 |
| 18.77 | 17 |
| 19.16 | 20 |
| 19.40 | 30 |
| 19.72 | 52 |
| 20.82 | 100 |
| 22.16 | 31 |
| 24.34 | 30 |
| 24.84 | 20 |
| 25.55 | 10 |
| 26.96 | 17 |
| 28.12 | 13 |

(8) The Polymorph (VIII-A) of Donepezil Salicylate (VIII)
Peaks in Powder X-Ray Diffraction Pattern of VIII-A

| Diffraction Angel (2θ, °) | Intensity (I/I₀) |
|---|---|
| 10.24 | 40 |
| 11.62 | 10 |
| 14.06 | 36 |
| 14.90 | 16 |
| 16.48 | 11 |
| 17.44 | 19 |
| 17.72 | 43 |
| 19.06 | 43 |
| 20.72 | 72 |
| 21.50 | 55 |
| 22.92 | 17 |
| 23.56 | 100 |
| 26.68 | 16 |
| 27.84 | 38 |
| 28.42 | 12 |

Infrared absorption spectrum wavenumber in of VII-A KBr (cm$^{-1}$): 424.3, 489.8, 520.7, 576.6, 630.6, 682.7, 719.3, 790.7, 821.5, 873.6, 939.2, 985.5, 1054.9, 1093.5, 1145.5, 1178.3, 1230.4, 1280.5, 1336.4, 1405.9, 1531.2, 1652.7, 1747.2, 1808.9, 1841.7, 1984.4, 2024.9, 2098.2, 2352.8, 2464.6, 2537.9, 2661.3, 2699.9, 2779.0, 2860.0, 2892.7, 3043.2, 3156.9, 3224.4, 3687.3.

(9) The Polymorph (IX-A) of Donepezil Fumarate (IX)
Peaks in Powder X-Ray Diffraction Pattern of IX-A

| Diffraction Angel (2θ, °) | Intensity (I/I₀) |
|---|---|
| 3.96 | 20 |
| 7.96 | 20 |
| 11.28 | 11 |
| 11.56 | 32 |
| 12.00 | 100 |
| 12.22 | 41 |
| 13.62 | 15 |
| 14.04 | 30 |
| 16.72 | 48 |
| 17.04 | 11 |
| 20.10 | 50 |
| 20.90 | 16 |
| 21.56 | 11 |
| 23.28 | 13 |
| 23.68 | 20 |
| 23.98 | 14 |
| 24.68 | 13 |
| 26.36 | 19 |
| 26.92 | 10 |

Infrared absorption spectrum wavenumber of IX-A in KBr (cm$^{-1}$): 532.3, 572.8, 671.1, 723.2, 775.3, 821.5, 879.4, 935.3, 960.4, 997.0, 1068.4, 1141.7, 1184.1, 1234.2, 1292.1, 1409.7, 1484.9, 1537.0, 1633.4, 2186.9, 2607.3, 2651.7, 2815.6, 2875.4, 2987.2, 3052.8, 3099.1, 3708.5, 3741.3, 3812.6, 3851.2, 3878.2, 3939.9, 3988.1.

(10) The Two Polymorphs (X-A and X-B) of Donepezil Maleate (X)
Peaks in Powder X-Ray Diffraction Pattern of the Polymorph (X-A) of Donepezil Maleate (X)

| Diffraction Angel (2θ, °) | Intensity (I/I₀) |
|---|---|
| 7.98 | 12 |
| 9.56 | 48 |
| 10.86 | 21 |
| 11.18 | 57 |
| 12.20 | 17 |
| 12.70 | 28 |
| 13.26 | 18 |
| 15.36 | 13 |
| 15.64 | 19 |
| 16.50 | 11 |
| 17.54 | 21 |
| 18.32 | 29 |
| 18.66 | 26 |
| 19.32 | 37 |
| 19.76 | 58 |
| 20.30 | 100 |
| 21.08 | 11 |
| 21.94 | 45 |
| 22.48 | 67 |
| 23.80 | 17 |
| 25.00 | 40 |
| 25.34 | 17 |
| 26.20 | 16 |
| 27.56 | 12 |
| 29.12 | 13 |
| 29.44 | 16 |
| 29.94 | 10 |

Infrared absorption spectrum wavenumber of the polymorph (X-A) of Donepezil maleate (X) in KBr (cm$^{-1}$): 437.8, 472.5, 595.9, 682.7, 723.2, 788.8, 821.5, 908.3, 958.5, 989.3, 1054.9, 1145.5, 1236.2, 1286.3, 1336.4, 1396.2, 1481.1, 1535.1, 1637.3, 1664.3, 1774.2, 1870.6, 2044.2, 2125.2, 2314.2, 2460.8, 2742.3, 2823.3, 2879.2, 2989.2, 3097.2, 3691.1, 3712.4, 3752.9, 3822.3, 3855.1, 3934.1.

Peaks in Powder X-ray Diffraction Pattern of the polymorph (X-B) of Donepezil Maleate (X)

| Diffraction Angel (2θ, °) | Intensity (I/I₀) |
|---|---|
| 4.24 | 13 |
| 4.92 | 57 |
| 9.60 | 31 |
| 10.84 | 10 |
| 11.18 | 36 |
| 12.76 | 24 |
| 15.76 | 44 |
| 16.94 | 19 |

-continued

| Diffraction Angel (2θ, °) | Intensity (I/I₀) |
|---|---|
| 17.58 | 22 |
| 17.90 | 75 |
| 18.30 | 12 |
| 18.68 | 11 |
| 19.32 | 35 |
| 19.74 | 100 |
| 20.26 | 68 |
| 21.16 | 17 |
| 21.94 | 15 |
| 22.40 | 38 |
| 22.82 | 11 |
| 23.28 | 13 |
| 23.86 | 12 |
| 24.28 | 11 |
| 24.88 | 21 |
| 25.26 | 18 |
| 26.24 | 15 |
| 29.24 | 17 |

Infrared absorption spectrum wavenumber of the other polymorph (X-B) of Donepezil maleate (X) in KBr ($cm^{-1}$): 426.2, 480.2, 594.0, 680.8, 719.3, 790.7, 821.5, 908.3, 960.4, 989.3, 1053.0, 1143.6, 1236.2, 1284.4, 1334.5, 1398.2, 1484.9, 1537.0, 1641.2, 1805.1, 1855.2, 1897.6, 2028.8, 2094.3, 2460.8, 2738.5, 2780.9, 2821.4, 2875.4, 2989.2, 3097.2, 3714.3, 3752.9, 3855.1, 3934.1.

(11) The Polymorph (XI-A) of Donepezil Malate (XI)

Peaks in Powder X-Ray Diffraction Pattern of the Polymorph (XI-A) of Donepezil Malate (XI)

| Diffraction Angel (2θ, °) | Intensity (I/I₀) |
|---|---|
| 3.977 | 17.3 |
| 8.158 | 11.7 |
| 12.362 | 35.8 |
| 15.637 | 71.5 |
| 16.548 | 57.9 |
| 17.601 | 16.9 |
| 19.545 | 100 |
| 20.022 | 12.5 |
| 20.869 | 49.6 |
| 21.398 | 25.7 |
| 23.288 | 42 |
| 25.090 | 52.4 |
| 25.413 | 32.8 |
| 26.882 | 15.1 |
| 29.594 | 10.2 |

(12) The Polymorph (XII-A) of Donepezil Benzenesulphonate (XII)

Peaks in Powder X-Ray Diffraction Pattern of the Polymorph (XII-A) of Donepezil Benzenesulphonate (XII)

| Diffraction Angel (2θ, °) | Intensity (I/I₀) |
|---|---|
| 8.078 | 24.9 |
| 11.928 | 88.1 |
| 12.365 | 26.3 |
| 14.880 | 16.6 |
| 15.367 | 52.7 |
| 17.721 | 100 |
| 18.324 | 25.9 |
| 18.858 | 44.4 |
| 20.786 | 12.9 |
| 21.286 | 12.9 |
| 21.776 | 10.3 |
| 22.118 | 46.9 |
| 23.110 | 20.9 |
| 23.998 | 11.5 |
| 25.194 | 39.5 |
| 25.799 | 11.6 |

The present invention discloses various methods for preparing Donepezil mesylate (I) and a polymorph thereof (I-A).

The methods for preparing Donepezil mesylate (I) include:

(I-1) adding a solution of methanesulphonic acid in absolute ethanol to a solution of Donepezil in ethyl acetate, and stirring at room temperature to precipitate a solid;

(I-2) adding a solution of methanesulphonic acid in acetone to a solution of Donepezil in ethyl acetate, and stirring at room temperature to precipitate a solid;

(I-3) adding a solution of methanesulphonic acid in 2-propanol to a solution of Donepezil in ethyl acetate, and stirring at room temperature to precipitate a solid; and (I-4) adding a solution of methanesulphonic acid in absolute ethanol to a solution of Donepezil in acetone at room temperature.

Examples 1 to 4 illustrate the methods (I-1) to (I-3).

The methods for preparing of the polymorph (I-A) of Donepezil mesylate (I) include:

(I-A-1) dissolving Donepezil mesylate in absolute ethanol to form a clear solution, and cooling to obtain a crystal;

(I-A-2) dissolving Donepezil mesylate in absolute ethanol to form a clear solution, adding dipropyl ether to the clear solution, and cooling to obtain a crystal;

(I-A-3) dissolving Donepezil mesylate in absolute ethanol to form a clear solution, adding n-hexane to the clear solution, and cooling to obtain a crystal;

(I-A-4) adding a solution of methanesulphonic acid in acetone to a solution of Donepezil in ethyl acetate to form a clear solution, and cooling to obtain a crystal;

(I-A-5) adding a solution of methanesulphonic acid in absolute ethanol to a solution of Donepezil in absolute ethanol to form a clear solution, adding dipropyl ether to the clear solution, and stirring at room temperature to obtain a crystal; and (I-A-6) adding a solution of methanesulphonic acid in a mixture of absolute ethanol and dipropyl ether to a solution of Donepezil in absolute ethanol to form a clear solution, and stirring at room temperature to obtain a crystal.

Examples 5 to 10 illustrate the methods (I-A-1) to (I-A-6).

The present invention discloses various methods for preparing Donepezil para-toluenesulfonate (II) and a polymorph thereof (II-A).

The methods for preparing Donepezil para-toluenesulfonate (II) include:

(II-1) adding a solution of para-toluenesulfonic acid in absolute ethanol to a solution of Donepezil in ethyl acetate, and stirring at room temperature to precipitate a solid;

(II-2) adding a solution of para-toluenesulfonic acid in acetone to a solution of Donepezil in ethyl acetate, and stirring at room temperature to precipitate a solid; and (II-3) adding a solution of para-toluenesulfonic acid in 2-propanol to a solution of Donepezil in ethyl acetate, and stirring at room temperature to precipitate a solid.

Examples 11 to 13 illustrate the methods (II-1) to (II-3).

The methods for preparing the polymorph (II-A) of Donepezil para-toluenesulfonate (II) include:

(II-A-1) dissolving Donepezil para-toluenesulfonate in absolute ethanol, and cooling to obtain a crystal; and (II-A-2) dissolving Donepezil para-toluenesulfonate in absolute ethanol, adding dipropyl ether to the above solution, and cooling to obtain a crystal.

Examples 14 to 15 illustrate the methods (II-A-1) to (II-A-2).

The present invention discloses various methods for preparing Donepezil succinate (III) and a polymorph thereof (III-A).

The methods for preparing Donepezil succinate (III) include:

(III-1) adding a solution of succinic acid in absolute ethanol to a solution of Donepezil in ethyl acetate, and stirring at room temperature to precipitate a solid;

(III-2) adding a solution of succinic acid in acetone to a solution of Donepezil in ethyl acetate, and stirring at room temperature to precipitate a solid;

(III-3) adding a solution of succinic acid in 2-propanol to a solution of Donepezil in ethyl acetate, and stirring at room temperature to precipitate a solid;

(III-4) adding a solution of Donepezil in ethyl acetate to a solution of succinic acid in absolute ethanol, and stirring at room temperature to precipitate a solid;

(III-5) adding a solution of Donepezil in ethyl acetate to a solution of succinic acid in acetone, and stirring at room temperature to precipitate a solid; and (III-6) adding a solution of Donepezil in ethyl acetate to a solution of succinic acid in 2-propanol, and stirring at room temperature to precipitate a solid.

Examples 16 to 22 illustrate the methods (III-1) to (III-6).

The methods for preparing the polymorph (III-A) of Donepezil succinate (III) include:

(III-A-1) dissolving Donepezil succinate in absolute ethanol, and cooling;

(III-A-2) dissolving Donepezil succinate in absolute ethanol, adding n-hexane to the above solution, and cooling;

(III-A-3) dissolving Donepezil succinate in absolute ethanol, adding distilled water to the above solution, and cooling;

(III-A-4) dissolving Donepezil succinate in a mixture of acetone and water, and cooling; and (III-A-5) dissolving Donepezil succinate in 2-propanol, and cooling.

Examples 23 to 27 illustrate the methods (III-A-1) to (III-A-5).

The present invention discloses various methods for preparing Donepezil tartrate (IV) and a polymorph thereof (IV-A).

The methods for preparing Donepezil tartrate (IV) include:

(IV-1) adding a solution of tartaric acid in absolute ethanol to a solution of Donepezil in ethyl acetate, and stirring at room temperature to precipitate a solid;

(IV-2) adding a solution of tartaric acid in a mixture of acetone and water to a solution of Donepezil in ethyl acetate, and stirring at room temperature to precipitate a solid;

(IV-3) adding a solution of tartaric acid in a mixture of 2-propanol and water to a solution of Donepezil in ethyl acetate, and concentrating;

(IV-4) adding a solution of Donepezil in ethyl acetate to a solution of tartaric acid in absolute ethanol, and stirring at room temperature to precipitate a solid;

(IV-5) adding a solution of Donepezil in ethyl acetate to a solution of tartaric acid in acetone, and stirring at room temperature to precipitate a solid; and (IV-6) adding a solution of Donepezil in ethyl acetate to a solution of tartaric acid in 2-propanol, and concentrating.

Examples 28 to 34 illustrate the methods (IV-1) to (IV-6).

The methods for preparing the polymorph (IV-A) of Donepezil tartrate (IV) include:

(IV-A-1) dissolving Donepezil tartrate in acetone, and cooling; and (IV-A-2) dissolving Donepezil tartrate in 2-propanol, and cooling.

Examples 35 to 36 illustrate the methods (IV-A-1) to (IV-A-2).

The present invention discloses various methods for preparing Donepezil sulphate (V) and two polymorphs thereof (V-A and V-B).

The methods for preparing Donepezil sulphate (V) include:

(V-1) adding a solution of sulfuric acid in absolute ethanol to a solution of Donepezil in ethyl acetate, and stirring at room temperature to precipitate a solid;

(V-2) adding a solution of sulfuric acid in acetone to a solution of Donepezil in ethyl acetate, and stirring at room temperature to precipitate a solid; and (V-3) adding a solution of sulfuric acid in 2-propanol to a solution of Donepezil in ethyl acetate, and stirring at room temperature to precipitate a solid.

Examples 37 to 39 illustrate the methods (V-1) to (V-3).

The method for preparing the polymorph (V-A) of Donepezil sulphate (V) comprises (V-A-1) dissolving Donepezil sulphate in absolute ethanol, and cooling.

The method for preparing the polymorph (V-B) of Donepezil sulphate (V) comprises (V-B-1) dissolving Donepezil sulphate in 2-propanol, and cooling.

Examples 40 to 41 illustrate the methods (V-A-1) to (V-B-1).

The present invention discloses various methods for preparing Donepezil nitrate (VI) and a polymorph thereof (VI-A).

The methods for preparing Donepezil nitrate (VI) include:

(VI-1) adding a solution of nitric acid in absolute ethanol to a solution of Donepezil in ethyl acetate, and stirring at room temperature to precipitate a solid;

(VI-2) adding a solution of nitric acid in acetone to a solution of Donepezil in ethyl acetate, and stirring at room temperature to precipitate a solid; and (VI-3) adding a solution of nitric acid in 2-propanol to a solution of Donepezil in ethyl acetate, and stirring at room temperature to precipitate a solid.

Examples 42 to 44 illustrate the methods (VI-1) to (VI-3).

The methods for preparing the polymorph (VI-A) of Donepezil nitrate (VI) include:

(VI-A-1) dissolving Donepezil nitrate in a mixture of absolute ethanol and water, and cooling;

(VI-A-2) dissolving Donepezil nitrate in a mixture of acetone and water, and cooling; and (VI-A-3) dissolving Donepezil nitrate in a mixture of 2-propanol and water, and cooling.

Examples 45 to 47 illustrate the methods (VI-A-1) to (VI-A-3).

The present invention discloses various methods for preparing Donepezil phosphate (VII) and a polymorph thereof (VII-A).

The methods for preparing Donepezil phosphate (VII) include:

(VII-1) adding a solution of phosphoric acid in acetone to a solution of Donepezil in ethyl acetate, and stirring at room temperature to precipitate a solid;

(VII-2) adding a solution of phosphoric acid in 2-propanol to a solution of Donepezil in ethyl acetate, and stirring at room temperature to precipitate a solid;

(VII-3) adding a solution of Donepezil in ethyl acetate to a solution of phosphoric acid in acetone, and stirring at room temperature to precipitate a solid; and (VII-4) adding a solution of Donepezil in ethyl acetate to a solution of phosphoric acid in 2-propanol, and stirring at room temperature to precipitate a solid.

Examples 48 to 51 illustrate the methods (VII-1) to (VII-4).

The method for preparing the polymorph (VII-A) of Donepezil phosphate (VII) comprises (VII-A-1) dissolving Donepezil phosphate in 2-propanol, adding dipropyl ether to the solution, and cooling.

Example 52 illustrates the method (VII-A-1).

The present invention discloses various methods for preparing Donepezil salicylate (VIII) and a polymorph thereof (VIII-A).

The methods for preparing Donepezil salicylate (VIII) include:

(VIII-1) adding a solution of salicylic acid in absolute ethanol to a solution of Donepezil in ethyl acetate, and stirring at room temperature to precipitate a solid;

(VIII-2) adding a solution of salicylic acid in acetone to a solution of Donepezil in ethyl acetate, and stirring at room temperature to precipitate a solid; and (VIII-3) adding a solution of salicylic acid in 2-propanol to a solution of Donepezil in ethyl acetate, and stirring at room temperature to precipitate a solid.

Examples 53 to 55 illustrate the methods (VIII-1) to (VIII-3). The methods for preparing the polymorph (VIII-A) of Donepezil salicylate (VIII) include:

(VIII-A-1) dissolving Donepezil salicylate in a mixture of acetone and water, and cooling; and (VIII-A-2) dissolving Donepezil salicylate in a mixture of 2-propanol and water, and cooling.

Examples 56 to 57 illustrate the methods (VIII-A-1) to (VIII-A-2).

The present invention discloses various methods for preparing Donepezil fumarate (IX) and a polymorph thereof (IX-A).

The methods for preparing Donepezil furmatrate (IX) include:

(IX-1) adding a solution of fumaric acid in absolute ethanol to a solution of Donepezil in ethyl acetate, and stirring at room temperature to precipitate a solid;

(IX-2) adding a solution of fumaric acid in acetone to a solution of Donepezil in ethyl acetate, and stirring at room temperature to precipitate a solid;

(IX-3) adding a solution of fumaric acid in 2-propanol to a solution of Donepezil in ethyl acetate, and stirring at room temperature to precipitate a solid;

(IX-4) adding a solution of Donepezil in ethyl acetate to a solution of fumaric acid in absolute ethanol, and stirring at room temperature to precipitate a solid;

(IX-5) adding a solution of Donepezil in ethyl acetate to a solution of fumaric acid in acetone, and stirring at room temperature to precipitate a solid; and (IX-6) adding a solution of Donepezil in ethyl acetate to a solution of fumaric acid in 2-propanol, and stirring at room temperature to precipitate a solid.

Examples 58 and 63 illustrate the methods (IX-1) to (IX-6).

The methods for preparing the polymorph (IX-A) of Donepezil fumarate (IX) include:

(IX-A-1) dissolving Donepezil fumarate in absolute ethanol, and cooling; and (IX-A-2) dissolving Donepezil fumarate in 2-propanol, and cooling.

Examples 64 and 65 illustrate the methods (IX-A-1) to (IX-A-2).

The present invention discloses various methods for preparing Donepezil maleate (X) and two polymorphs thereof (X-A and X-B).

The methods for preparing Donepezil maleate (X) include:

(X-1) adding a solution of maleic acid in absolute ethanol to a solution of Donepezil in ethyl acetate, and concentrating;

(X-2) adding a solution of maleic acid in acetone to a solution of Donepezil in ethyl acetate, and concentrating;

(X-3) adding a solution of maleic acid in 2-propanol to a solution of Donepezil in ethyl acetate, and concentrating;

(X-4) adding a solution of Donepezil in ethyl acetate to a solution of maleic acid in absolute ethanol, and concentrating;

(X-5) adding a solution of Donepezil in ethyl acetate to a solution of maleic acid in acetone, and concentrating;

(X-6) adding a solution of Donepezil in ethyl acetate to a solution of maleic acid in 2-propanol, and concentrating;

(X-7) adding a solution of maleic acid in absolute ethanol to a solution of Donepezil in ethyl acetate, and stirring at room temperature to precipitate a solid;

(X-8) adding a solution of maleic acid in acetone to a solution of Donepezil in ethyl acetate, and stirring at room temperature to precipitate a solid;

(X-9) adding a solution of maleic acid in 2-propanol to a solution of Donepezil in ethyl acetate, and stirring at room temperature to precipitate a solid;

(X-10) adding a solution of Donepezil in ethyl acetate to a solution of maleic acid in absolute ethanol, and stirring at room temperature to precipitate a solid;

(X-11) adding a solution of Donepezil in ethyl acetate to a solution of maleic acid in acetone, and stirring at room temperature to precipitate a solid; and (X-12) adding a solution of Donepezil in ethyl acetate to a solution of maleic acid in 2-propanol, and stirring at room temperature to precipitate a solid.

Examples 66 to 77 illustrate the methods (X-1) to (X-12).

The methods for preparing the polymorph (X-A) of Donepezil maleate (X) include:

(X-A-1) dissolving Donepezil maleate in absolute ethanol, and cooling;

(X-A-2) dissolving Donepezil maleate in acetone, and cooling;

(X-A-3) dissolving Donepezil maleate in 2-propanol, and cooling; and (X-A-4) dissolving Donepezil maleate (½ acid) in absolute ethanol, and cooling.

Examples 78 to 81 illustrate the methods (X-A-1) to (X-A-4).

The methods for preparing the polymorph (X-B) of Donepezil maleate (X) include:

(X-B-1) dissolving Donepezil maleate (½ acid) in acetone, and cooling; and (X-B-1) dissolving Donepezil maleate (½ acid) in 2-propanol, and cooling.

Examples 82 to 83 illustrate the methods (X-B-1) to (X-B-2).

From the embodiments for preparing mesylate, para-toluenesulfonate, succinate, tartrate, salicylate, fumarate, maleate, gallate, acetylsalicylate, citrate, aspartate, glutaminate, lactate, gluconate, ascorbate, malonate, malate, sorbate, acetate, formate, sulphate, nitrate, phosphate, or benzenesulphonate of Donepezil according to the present invention, a general method for preparing a salt of Donepezil is generalized, which comprises:

a) dissolving Donepezil in a suitable first solvent to form solution A;

b) dissolving a corresponding acid in a suitable second solvent to form solution B;

c) adding solution A to solution B or vice versa to form a mixed solution; and d) concentrating the mixed solution obtained in step c) or stirring it at room temperature to obtain a solid of the corresponding salt of Donepezil.

The first and second solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropylether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane, and mixtures thereof. The ratio of Donepezil to the acid is 1:0.2-5 (molar ratio).

From the various methods for preparing polymorphs of mesylate, para-toluenesulfonate, succinate, tartrate, salicylate, fumarate, maleate, gallate, acetylsalicylate, citrate, aspartate, glutaminate, lactate, gluconate, ascorbate, malonate, malate, sorbate, acetate, formate, sulphate, nitrate, phosphate, or benzenesulphonate of Donepezil according to the present invention, a general method for preparing a polymorph of a salt of Donepezil is generalized, which comprises:

a) dissolving Donepezil in a suitable third solvent to form solution C;

b) dissolving a corresponding acid in a suitable fourth solvent to form solution D;

c) adding solution C to solution D or vice versa to form a clear solution E; and d) stirring solution E obtained in step c) at room temperature to precipitate a polymorph of a salt of Donepezil, or concentrating or cooling solution E to obtain a corresponding polymorph of a salt of Donepezil, or adding a fifth solvent to solution E and cooling or concentrating to obtain a corresponding polymorph of a salt of Donepezil.

The third, fourth and fifth solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropylether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane, and mixtures thereof.

From the various methods for preparing polymorphs of mesylate, para-toluenesulfonate, succinate, tartrate, salicylate, fumarate, maleate, gallate, acetylsalicylate, citrate, aspartate, glutaminate, lactate, gluconate, ascorbate, malonate, malate, sorbate, acetate, formate, sulphate, nitrate, phosphate, or benzenesulphonate of Donepezil according to the present invention, a second general method for preparing a polymorph of a salt of Donepezil is generalized, which comprises:

a) dissolving a salt of Donepezil in a suitable solvent (a sixth solvent) to form a solution;

b) concentrating or cooling the solution of the salt of Donepezil to obtain a polymorph of the corresponding salt of Donepezil, or adding a seventh solvent to the solution of the salt of Donepezil and cooling subsequently to obtain a polymorph of the corresponding salt of Donepezil.

The sixth and seventh solvents are independently selected from the group consisting of ethyl acetate, methyl acetate, methyl formate, ethyl formate, propyl formate, methanol, ethanol, propanol, isopropanol, butanol, ethylene glycol, propylene glycol, ethylene glycol monomethyl ether, ethylene glycol monoethyl ether, ethylene glycol dimethyl ether, propylene glycol monomethyl ether, propylene glycol monoethyl ether, propylene glycol dimethyl ether, tetrahydrofuran, acetone, butanone, and water.

The fifth solvent is selected from the group consisting of ethyl acetate, methyl acetate, propyl acetate, methyl formate, ethyl formate, propyl formate, butyl formate, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane, and mixtures thereof.

The compound of formula (I), the solvates of the compound of formula (I), the polymorphs of the compound of formula (I), or the polymorphs of the solvates of the compound of formula (I) according to the present invention may be used as active ingredients to treat and/or ameliorate diseases, physiological dysfunctions and various pains caused by low level of acetylcholine, including but not limited to senile dementia (AD), attention deficient disorder of childhood, memory deterioration, paralysis agitans (demeritia), brain injury, multiple sclerosis, Down's Syndrome, delirium, mood disorder, Huntington's disease, and sleep disorder.

The compound of formula (I), the solvates of the compound of formula (I), the polymorphs of the compound of formula (I), or the polymorphs of the solvates of the compound of formula (I) according to the present invention may be used as active ingredients to treat various pains, including all discomforts involving a sense of pain, functional pain syndromes or organic pain syndromes, which include but are not limited to neuropathic headache, in particular migraine, primary fibromyalgia, amputation, tumoral denervation, traumatic denervation or pains caused by autoimmune mechanism.

Unit dosages of the compound of formula (I), the solvates of the compound of formula (I), the polymorphs of the compound of formula (I), or the polymorphs of the solvates of the compound of formula (I) according to the present invention when used as active ingredients are in the range of from 1.0 mg to 50 mg.

Unless otherwise indicated, the term "unit dosage" as used herein refers to a dosage to be taken as a single dose in a single administration.

The present invention discloses for the first time some non-bitter or slightly bitter salts of Donepezil, i.e., compounds of formula (II), and orally disintegrating tablets, oral liquids, buccal tablets, effervescent tablets, chewable tablets, granules or lyophilized rapid dissolving tablets comprising at least one of the compounds of formula (II), polymorphs of the compounds of formula (II), solvates of the compounds of formula (II), and polymorphs of solvates of the compound of formula (II),

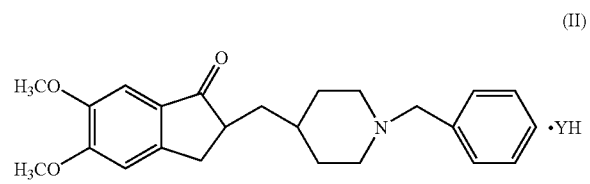

(II) ·YH wherein YH represents nitric acid, salicylic acid, acetylsalicylic acid, gallic acid, or maleic acid.

The compound of formula (II) is non-bitter wherein YH represents nitric acid, salicylic acid, acetylsalicylic acid or gallic acid; and the compound of formula (II) is slightly bitter wherein YH represents maleic acid, of which the slightly bitter taste may be masked by a taste-masking agent when preparing a pharmaceutical formulation.

A method for preparing a compound of formula (II) or a solvate thereof according to the present invention comprises the following steps:

1) dissolving a compound of formula (XX) in a suitable eighth solvent to form Solution F;

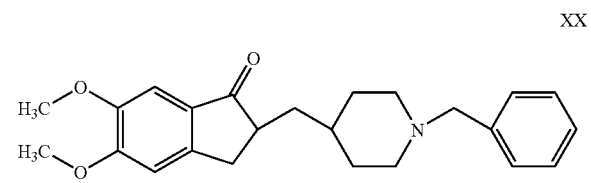 [SMILES: COc1cc2c(cc1OC)C(=O)C(CC1CCN(Cc3ccccc3)CC1)C2]

XX 2) dissolving a corresponding acid YH in a suitable ninth solvent to form Solution G; and 3) adding Solution F to Solution G or vice versa to form a mixed solution, and separating a salt of Donepezil (i.e., the compound of formula (II)) from the solution.

The eighth and ninth solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane, and mixtures thereof.

A method for preparing a polymorph of the compound of formula (II) or a polymorph of a solvate of the compound of formula (II) according to the present invention comprises the following steps:

1) dissolving a compound of formula (XX) in a suitable eighth solvent to form Solution H;

2) dissolving a corresponding acid YH in a suitable ninth solvent to form Solution J; and 3) adding Solution H to Solution J or vice versa to form a Solution K; and 4) stirring Solution K at room temperature to precipitate the polymorph of the compound of formula (II) or the polymorph of the solvate of the compound of formula (II); or concentrating or cooling Solution K to obtain the polymorph of the compound of formula (II) or the polymorph of the solvate of the compound of formula (II); or adding a tenth solvent to Solution K, then stirring, and cooling or concentrating to obtain the polymorph of the compound of formula (II) or the polymorph of the solvate of the compound of formula (II).

The eighth, ninth and tenth solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform, 1,2-dichloroethane and mixtures thereof. The ratio of Donepezil to the acid is in the range of 1:0.2-5 (molar ratio).

When in use, the compound of formula (II) according to the present invention may be in a non-solvated form or in a solvated form, in particular a hydrated or alcoholated form.

The present invention further discloses methods for preparing oral liquids, granules, buccal tablets, effervescent tablets, orally disintegrating tablets, lyophilized rapid dissolving tablets, chewable tablets and tables comprising the compound of formula (II), the polymorphs of the compound of formula (II), the solvates of the compound of formula (II), or the polymorphs of the solvates of the compound of formula (II).

Accordingly, the present invention provides preparations and formulations of orally disintegrating tablets comprising the compound of formula (II), the polymorphs of the compound of formula (II), the solvates of the compound of formula (II), or the polymorphs of the solvates of the compound of formula (II). The preparation can be easily performed, and the resulted orally disintegrating tablets can rapidly disintegrate and release active ingredients in mouth and can possess a good taste. A representative formulation of the orally disintegrating tablets comprises the following components expressed in weight percentage (Donepezil nitrate as an example):

| Donepezil Nitrate: | 0.1-20% | Filler: | 35-90% |
| --- | --- | --- | --- |
| Disintegrant: | 1-30% | Flavoring Agent: | 0.0-5% |
| Lubricant: | 0.1-10% | Glidant: | 0.01-5% |
| Colorant: | 0.0-1% | Binder: | 0-5% |

Preferred Formulation:

| Donepezil Nitrate: | 1-15% | Filler: | 50-80% |
| --- | --- | --- | --- |
| Disintegrant: | 4-25% | Flavoring Agent: | 0.1-2% |
| Lubricant: | 0.4-8% | Glidant: | 0.1-3% |
| Colorant: | 0.0-1% | Binder: | 0-5% |

More Preferred Formulation:

| Donepezil Nitrate: | 5-13% | Filler: | 65-75% |
| --- | --- | --- | --- |
| Disintegrant: | 8-20% | Flavoring Agent: | 0.5-1% |
| Lubricant: | 0.5-5% | Glidant: | 0.2-1.5% |
| Colorant: | 0.0-1% | Binder: | 0-5% |

The filler used in the orally disintegrating tablets according to the present invention is selected from the group consisting of dextrin, microcrystalline cellulose (MCC), lactose, mannitol, erythritol, starch, sugar powder, and mixtures thereof.

The disintegrant used in the orally disintegrating tablets according to the present invention is selected from the group consisting of low substituted hydropropyl cellulose (L-HPC), cross-linked polyvinylpyrrolidone (PVPP), cross-linked carboxymethylcellulose sodium (CCNa), cross-linked carboxymethylstarch sodium (CCMS-Na), treated agar (TAG), and mixtures thereof.

The flavoring agent used in the orally disintegrating tablets according to the present invention can be a natural or artificial sweetening agent, such as stevioside, xylitol, aspartame, orange solid essence, sodium cyclamate, sorbose, and mixtures thereof.

The lubricant used in the orally disintegrating tablets according to the present invention is selected from the group consisting of magnesium stearate, talc powder, magnesium lauryl sulfate, and mixtures thereof.

The glidant used in the orally disintegrating tablets according to the present invention is selected from the group consisting of micropowder silica gel, Cab-O-sil (Cabot Company), Arosil (Degussa Company), hydrated sodium aluminosilicate, and mixtures thereof.

The binder used in the orally disintegrating tablets according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The above-mentioned orally disintegrating tablets comprising non-bitter salts of Donepezil may further comprise a suitable colorant, which is selected from the group consisting of carotene, sunset yellow, tartrazine, carmine, chlorophyl, and mixtures thereof.

The above-mentioned orally disintegrating tablet formulations comprising non-bitter salts of Donepezil are only specific examples to illustrate the spirit of the present invention, and should not be interpreted as any limitation to the present invention. Accordingly, any other formulations suitable for the orally disintegrating tablets are also within the scope of the present invention.

The present invention further discloses a method for preparing the orally disintegrating tablets comprising non-bitter salts of Donepezil, which comprises: a) pulverizing an active ingredient, a filler, a disintegrant and a flavoring agent, sieving with a 80-mesh screen, and mixing uniformly; b) adding a glidant and a lubricant, mixing uniformly, and determining contents of the powder; and c) tabletting to provide the orally disintegrating tablets with pre-determined tablet weight. The preparation has a disintegrating time in the range of from 1 to 60 seconds and the particle size after disintegrating is less than 710 μm.

The above-mentioned method for preparing the orally disintegrating tablets comprising non-bitter salts of Donepezil is only a specific example to illustrate the spirit of the present invention, and should not be interpreted as any limitation to the present invention. Accordingly, any other methods suitable for preparing the orally disintegrating tablets are also within the scope of the present invention.

The beneficial features of the orally disintegrating tablets comprising non-bitter salts of Donepezil according to the present invention lie in a reasonable formulation, a good disintegrating property, not producing a gritty feeling and an unpleasant taste in mouth, and improving the compliance of a patient, particularly suitable for elder patients having difficulty in swallowing. The dosage form can be produced with conventional equipments for preparing tablets. The preparing process utilizes a direct powder-pressing procedure, which is very simple and can be easily controlled and is suitable for an industrial-scale production.

The present invention further provides preparations and formulations of granules comprising the compound of formula (II), the polymorphs of the compound of formula (II), the solvates of the compound of formula (II), or the polymorphs of the solvates of the compound of formula (II). The preparation can be easily performed, and the resulted granules can be rapidly dissolved in water, juice, acidic beverage and milk and release active ingredients, and can possess a good taste. A representative formulation of the granule comprises the following components expressed in weight percentage (Donepezil nitrate as an example):

| Donepezil Nitrate: | 0.05-1% | Filler: | 92-99.9% |
|---|---|---|---|
| Flavoring Agent: | 0.0-5% | Colorant: | 0.0-2% |
| Binder: | 0.01-3% | | |

The filler used in the granules according to the present invention is selected from the group consisting of starch, sugar powder, lactose, dextrin, microcrystalline cellulose, erythritol, mannitol, and mixtures thereof.

The binder used in the granules according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The flavoring agent used in the granules according to the present invention can be a natural or artificial sweetening agent, such as stevioside, aspartame, orange solid essence, sodium cyclamate, sorbose, sucrose, glucose, and mixtures thereof.

The above-mentioned granules comprising non-bitter salts of Donepezil may further comprise a suitable colorant, which is selected from the group consisting of carotene, sunset yellow, tartrazine, carmine, chlorophyl, and mixtures thereof.

The above-mentioned granule formulations comprising non-bitter salts of Donepezil are only specific examples to illustrate the spirit of the present invention, and should not be interpreted as any limitation to the formulations of the present invention. Accordingly, any other formulations suitable for the granules are also within the scope of the present invention.

The present invention further discloses a method for preparing the granules comprising non-bitter salts of Donepezil, which comprises: a) pulverizing an active ingredient, a filler, and a flavoring agent, sieving with a 80-mesh screen, and mixing uniformly; b) dissolving a colorant in a binder, and adding the binder portion-wisely to form a soft material; and c) granulating the soft material with a 14-mesh screen, drying the resulted particles at 60° C. for 1-2 hours and sizing with a 16-mesh screen.

The above-mentioned method for preparing the granules comprising non-bitter salts of Donepezil is only a specific example to illustrate the spirit of the present invention, and should not be interpreted as any limitation to the present invention. Accordingly, any other methods suitable for preparing the granules are also within the scope of the present invention.

The present invention further provides preparations and formulations of effervescent tablets comprising the compound of formula (II), the polymorphs of the compound of formula (II), the solvates of the compound of formula (II), or the polymorphs of the solvates of the compound of formula (II). The preparation can be easily performed, and the resulted effervescent tablets can be rapidly dissolved in water, juice, acidic beverage and milk and release active ingredients, and can possess a good taste. A representative formulation of the effervescent tablets comprises the following components expressed in weight percentage (Donepezil nitrate as an example):

| Donepezil Nitrate: | 1-20% | Filler: | 30-80% |
| Effervescent: | 5-40% | Disintegrant: | 1-30% |
| Flavoring Agent: | 0.0-5% | Binder: | 0.1-3% |
| Lubricant: | 0.1-10% | Colorant: | 0-1% |

The filler used in the effervescent tablets according to the present invention is selected from the group consisting of starch, sugar powder, lactose, dextrin, microcrystalline cellulose, mannitol, and mixtures thereof.

The acid source in the effervescent used in the effervescent tablets according to the present invention is selected from the group consisting of citric acid, tartaric acid, tetrahexanoic acid, lysine, arginine, and mixtures thereof.

The base source in the effervescent used in the effervescent tablets according to the present invention is selected from the group consisting of sodium bicarbonate, sodium carbonate, potassium bicarbonate, potassium carbonate, and mixtures thereof.

The disintegrant used in the effervescent tablets according to the present invention is selected from the group consisting of low substituted hydropropyl cellulose (L-HPC), carboxymethylstarch sodium, cross-linked polyvinylpyrrolidone (PVPP), cross-linked carboxymethylcellulose sodium (CCNa), cross-linked carboxymethylstarch sodium (CCMS-Na), treated agar (TAG), and mixtures thereof.

The binder used in the effervescent tablets according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The flavoring agent used in the effervescent tablets according to the present invention can be a natural or artificial sweetening agent, such as stevioside, aspartame, orange solid essence, sodium cyclamate, sorbose, and mixtures thereof.

The lubricant used in the effervescent tablets according to the present invention is selected from the group consisting of magnesium stearate, talc powder, magnesium lauryl sulfate, and mixtures thereof.

The above-mentioned effervescent tablets comprising non-bitter salts of Donepezil may further comprise a suitable colorant, which is selected from the group consisting of carotene, sunset yellow, tartrazine, carmine, chlorophyl, and mixtures thereof.

The above-mentioned effervescent tablet formulations comprising non-bitter salts of Donepezil are only specific examples to illustrate the spirit of the present invention, and should not be interpreted as any limitation to the effervescent tablet formulations of the present invention. Accordingly, any other formulations suitable for the effervescent tablets are also within the protection scope of the present invention.

The present invention further discloses a process for preparing the effervescent tablets comprising non-bitter salts of Donepezil, which comprises: a) pulverizing an active ingredient, a filler, a disintegrant, and a flavoring agent, sieving with a 80-mesh screen, and mixing uniformly; b) adding a binder portion-wisely to form a soft material; c) granulating the soft material with a 25-mesh screen, drying the resulted particles at 60° C. for 1-2 hours, and sizing with a 30-mesh screen; d) adding a lubricant, mixing uniformly, and determining the content of the active ingredient in particles; and e) tabletting to produce the effervescent tablets with pre-determined tablet weigh.

The above-mentioned method for preparing the effervescent tablets comprising non-bitter salts of Donepezil is only a specific example to illustrate the spirit of the present invention, and should not be interpreted as any limitation to the present invention. Accordingly, any other methods suitable for preparing the effervescent tablets are also within the scope of the present invention.

The present invention further provides preparations and formulations of buccal tablets comprising the compound of formula (II), the polymorphs of the compound of formula (II), the solvates of the compound of formula (II), or the polymorphs of the solvates of the compound of formula (II). The preparation can be easily performed, and the resulted buccal tablets possess a good taste. A representative formulation of the buccal tablets comprises the following components expressed in weight percentage (Donepezil nitrate as an example):

| Donepezil Nitrate: | 1-20% | Filler: | 70-95% |
| Lubricant: | 0.05-5% | Binder: | 0.1-3% |
| Flavoring Agent: | 0.0-5% | Colorant: | 0.0-1% |

The filled used in the buccal tablets according to the present invention is selected from the group consisting of starch, sugar powder, lactose, dextrin, microcrystalline cellulose, mannitol, xylitol, erythritol, sorbitol, and mixtures thereof.

The binder used in the buccal tablets according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The flavoring agent used in the buccal tablets according to the present invention is selected from the group consisting of stevioside, aspartame, fruit essence, sodium cyclamate, sorbose, sucrose, glucose, menthol crystal, citric acid, ascorbic acid, and mixtures thereof.

The lubricant used in the buccal tablets according to the present invention is selected from the group consisting of magnesium stearate, talc powder, calcium stearate, stearic acid, polyethylene glycol 4000, polyethylene glycol 6000, magnesium lauryl sulfate, and mixtures thereof.

The above-mentioned buccal tablets comprising non-bitter salts of Donepezil may further comprise a suitable colorant, which is selected from the group consisting of carotene, sunset yellow, tartrazine, carmine, chlorophyl, and mixtures thereof.

The above-mentioned buccal tablet formulations comprising non-bitter salts of Donepezil are only specific examples to illustrate the spirit of the present invention, and should not be interpreted as any limitation to the buccal tablet formulations of the present invention. Accordingly, any other formulations suitable for the buccal tablets are also within the scope of the present invention.

The present invention further discloses a process for preparing the buccal tablets comprising non-bitter salts of Donepezil, which comprises: a) pulverizing an active ingredient, a filler, and a flavoring agent, sieving with a 80-mesh screen, and mixing uniformly; b) adding a binder portion-wisely to form a soft material; c) granulating the soft material with a 25-mesh screen, drying the resulted particles at 60° C. for 1-2 hours, and sizing with a 30-mesh screen; d) adding a lubricant and a colorant, mixing uniformly, and determining the content of the active ingredient in particles; and e) tabletting to produce the buccal tablets with pre-determined tablet weigh.

The above-mentioned method for preparing the buccal tablets comprising non-bitter salts of Donepezil is only a specific example to illustrate the spirit of the present invention, and should not be interpreted as any limitation to the methods for preparing the buccal tables according to the present invention. Accordingly, any other methods suitable for preparing the buccal tablets are also within the scope of the present invention.

The present invention further provides preparations and formulations of chewable tablets comprising the compound of formula (II), the polymorphs of the compound of formula (II), the solvates of the compound of formula (II), or the polymorphs of the solvates of the compound of formula (II). The preparation can be easily performed, and the resulted chewable tablets possess a good taste. A representative formulation of the chewable tablets comprises the following components expressed in weight percentage (Donepezil nitrate as an example):

| | | | |
|---|---|---|---|
| Donepezil Nitrate: | 1-20% | Filler: | 65-95% |
| Flavoring Agent: | 0.0-5% | Binder: | 0.1-3% |
| Lubricant: | 0.1-10% | Disintegrant: | 0-10% |
| Colorant: | 0-1% | | |

The filler used in the chewable tablets according to the present invention is selected from the group consisting of starch, sugar powder, lactose, dextrin, microcrystalline cellulose, mannitol, xylitol, erythritol, sorbitol, and mixtures thereof.

The binder used in the chewable tablets according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The flavoring agent used in the chewable tablets according to the present invention is selected from the group consisting of stevioside, aspartame, fruit essence, orange essence, sodium cyclamate, sorbose, sucrose, glucose, menthol crystal, citric acid, ascorbic acid, and mixtures thereof.

The lubricant used in the chewable tablets according to the present invention is selected from the group consisting of magnesium stearate, talc powder, calcium stearate, stearic acid, polyethylene glycol 4000, polyethylene glycol 6000, magnesium lauryl sulfate, and mixtures thereof.

The above-mentioned chewable tablet formulations comprising non-bitter salts of Donepezil may further comprise a suitable disintegrant, which is selected from the group consisting of starch, low substituted hydropropyl cellulose (L-HPC), carboxymethylstarch sodium, cross-linked polyvinylpyrrolidone (PVPP), cross-linked carboxymethylcellulose sodium (CCNa), cross-linked carboxymethylstarch sodium (CCMS-Na), treated agar (TAG), and mixtures thereof.

The above-mentioned chewable tablet formulations comprising non-bitter salts of Donepezil may further comprise a suitable colorant, which is selected from the group consisting of carotene, sunset yellow, tartrazine, carmine, chlorophyl, and mixtures thereof.

The above-mentioned chewable tablet formulations comprising non-bitter salts of Donepezil are only specific examples to illustrate the spirit of the present invention, and should not be interpreted as any limitation to the chewable tablet formulations of the present invention. Accordingly, any other formulations suitable for the chewable tablets are also within the scope of the present invention.

The present invention further discloses a process for preparing the chewable tablets comprising non-bitter salts of Donepezil, which comprises: a) pulverizing an active ingredient, a filler, and a flavoring agent, sieving with a 80-mesh screen, and mixing uniformly; b) adding a binder portion-wisely to form a soft material; c) granulating the soft material with a 25-mesh screen, drying the resulted particles at 60° C. for 1-2 hours, and sizing with a 30-mesh screen; d) adding a lubricant, mixing uniformly, and determining the content of the active ingredient in the particles; and e) tableing to provide the chewable tablets with pre-determined tablet weigh. If desired, when preparing the soft material, a disintegrant and a colorant can be added.

The above-mentioned method for preparing the chewable tablets comprising non-bitter salts of Donepezil is only a specific example to illustrate the spirit of the present invention, and should not be interpreted as any limitation to the methods for preparing the chewable tables according to the present invention. Accordingly, any other methods suitable for preparing the chewable tablets are also within the protection scope of the present invention.

The present invention further provides preparations and formulations of lyophilized rapid dissolving tablets comprising the compound of formula (II), the polymorphs of the compound of formula (II), the solvates of the compound of formula (II), or the polymorphs of the solvates of the compound of formula (II). The preparation can be easily performed, and the resulted lyophilized rapid dissolving tablets can be rapidly dissolved in mouth and possess a good taste. A representative formulation of the lyophilized rapid dissolving tablets comprises the following components expressed in weight percentage (Donepezil nitrate as an example):

| | |
|---|---|
| Donepezil Nitrate: | 1-20% |
| Filler: | 78-96% |
| Flavoring Agent: | 0.0-5% |

The filler used in the lyophilized rapid dissolving tablets according to the present invention is selected from the group consisting of mannitol, gelatin, sodium chloride, dextran, glucose, lactose, maltose, sucrose, sorbitol, hydroethylcellulose, and mixtures thereof.

The flavoring agent used in the lyophilized rapid dissolving tablets according to the present invention is selected from the group consisting of stevioside, aspartame, fruit essence, sodium cyclamate, menthol crystal, citric acid, ascorbic acid, and mixtures thereof.

The above-mentioned lyophilized rapid dissolving tablet formulations comprising non-bitter salts of Donepezil are only specific examples to illustrate the spirit of the present invention, and should not be interpreted as any limitation to the lyophilized rapid dissolving tablet formulations of the present invention. Accordingly, any other formulations suitable for the lyophilized rapid dissolving tablets are also within the scope of the present invention.

The present invention further discloses a process for preparing the lyophilized rapid dissolving tablets comprising non-bitter salts of Donepezil, which comprises: a) pulverizing an active ingredient and a filler, and sieving with a 80-mesh screen; b) suspending the active ingredient in a solution of hydroethylcellulose; c) dissolving other excipients to form a solution; d) mixing the two solutions, and placing the resultant solution in a mold to freeze at low temperature; and e) completely drying the mixture at vacuum in a lyophilizer, and sealing to obtain the lyophilized rapid dissolving tablets.

The above-mentioned method for preparing the lyophilized rapid dissolving tablets comprising non-bitter salts of Donepezil is only a specific example to illustrate the spirit of the present invention, and should not be interpreted as any limitation to the methods for preparing the lyophilized rapid dissolving tablets according to the present invention. Accordingly, any other methods suitable for preparing the lyophilized rapid dissolving tablets are also within the scope of the present invention.

The present invention further provides preparations and formulations of oral liquids comprising the compound of formula (II), the polymorphs of the compound of formula (II), the solvates of the compound of formula (II), or the polymorphs of the solvates of the compound of formula (II). The preparation can be easily performed, and the resulted oral liquids possess a good taste. A representative formulation of the oral liquids comprises the following components expressed in weight percentage (Donepezil nitrate as an example):

| Donepezil Nitrate: | 0.05-0.5% | Cosolvent: | 0.2-10% |
|---|---|---|---|
| Preservative: | 0.01-1% | Flavoring Agent: | 0.0-5% |
| Solvent: | 85-99.5% | Colorant: | 0-1% |

The solvent used in the oral liquids according to the present invention is selected from the group consisting of water, a mixture of water and polyethylene glycol 200, polyethylene glycol 300, polyethylene glycol 400 or polyethylene glycol 600, and a mixture of water and glycerol.

The cosolvent used in the oral liquids according to the present invention is selected from the group consisting of poloxamer, ethanol, 1,2-propylene glycol, glycerol, polyethylene glycol 200-600, and mixtures thereof.

The preservative used in the oral liquids according to the present invention is selected from the group consisting of nipagins, benzoic acid, sodium benzoate, sorbic acid, and mixtures thereof, in which the nipagins are selected from the group consisting of methyl Nipagin ester, ethyl Nipagin ester, propyl Nipagin ester, butyl Nipagin ester, and mixtures thereof.

The flavoring agent used in the oral liquids according to the present invention can be a neutral or artificial sweetening agent, such as stevioside, aspartame, orange solid essence, sodium cyclamate, sorbose, sucrose, glucose, and mixtures thereof.

The above-mentioned oral liquids comprising non-bitter salts of Donepezil may further comprise a suitable colorant, which is selected from the group consisting of carotene, sunset yellow, tartrazine, carmine, chlorophyl, and mixtures thereof.

The above-mentioned oral liquid formulations comprising non-bitter salts of Donepezil are only specific examples to illustrate the spirit of the present invention, and should not be interpreted as any limitation to the oral liquid formulations according to the present invention. Accordingly, any other formulations suitable for the oral liquids are also within the scope of the present invention.

The present invention further discloses a process for preparing the oral liquids comprising non-bitter salts of Donepezil, which comprises: a) dissolving a cosolvent in distilled water, adding an active ingredient, and stirring until complete dissolution; b) adding a preservative, stirring to mix uniformly, and filtering; and c) adding distilled water to a certain volume, and sterilizing to obtain the oral liquids.

The above-mentioned process for preparing the oral liquids comprising non-bitter salts of Donepezil is only a specific example to illustrate the spirit of the present invention, and should not be interpreted as any limitation to the methods for preparing the oral liquids according to the present invention. Accordingly, any other processes suitable for preparing the oral liquids are also within the scope of the present invention.

The present invention further discloses a use of oral liquids, granules, buccal tablets, effervescent tablets, chewable tablets, orally disintegrating tablets, or lyophilized rapid dissolving tablets comprising at least one of the compound of formula (II), the solvates of the compound of formula (II), the polymorphs of the compound of formula (II), and the polymorphs of the solvates of the compound of formula (II) in the preparation of inhibitors of acetylcholinesterase, wherein YH represents salicylic acid, nitric acid, gallic acid, maleic acid, or acetylsalicylic acid, which is characterized in that the said use is to prepare a medicament for the treatment of Alzheimer's disease (AD), hypomnesis, hyperkinetic syndrome of childhood, progressive cerebral atrophy, and parkinson's disease.

The unit dosage of the oral liquids, granules, buccal tablets, effervescent tablets, chewable tablets, orally disintegrating tablets, or lyophilized rapid dissolving tablets comprising at least one of the compound of formula (II), the solvates of the compound of formula (II), the polymorphs of the compound of formula (II), and the polymorphs of the solvates of the compound of formula (II) according to the present invention in the medicament used as inhibitors of acetylcholinesterase may range from 0.5 mg to 50 mg, more preferably from 1 mg to 30 mg, most preferably from 2 mg to 20 mg.

The most convenient unit dosage of the oral liquids, granules, buccal tablets, effervescent tablets, chewable tablets, orally disintegrating tablets, or lyophilized rapid dissolving tablets comprising at least one of the compound of formula (II), the solvates of the compound of formula (II), the polymorphs of the compound of formula (II), and the polymorphs of the solvates of the compound of formula (II) according to the present invention used as inhibitors of acetylcholinesterase is that equivalent to 5 mg, 10 mg, or 20 mg of Donepezil hydrochloride.

A method for preparing the compound of formula (III), the solvate of the compound of formula (III), the co-crystal of the compound of formula (III), and the co-crystal of the solvate of the compound of formula (III) according to the present invention comprises: dissolving a salt of Donepezil in suitable γ solvent, optionally adding β solvent, adding a corresponding acid QH, and concentrating, cooling or adding ψ solvent to precipitate a solid, i.e., obtaining the compound of formula (III), the solvate of the compound of formula (III), the co-crystal of the compound of formula (III), or the co-crystal of the solvate of the compound of formula (III).

The γ, β and ψ solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform or 1,2-dichloroethane, and mixtures thereof. The ratio of Donepezil to acid QH is in the range of 1:0.1-10 (molar ratio).

A second method for preparing the compound of formula (III), the solvate of the compound of formula (III), the co-crystal of the compound of formula (III), and the co-crystal of the solvate of the compound of formula (III) according to the present invention comprises: dissolving the compound of formula (III) or a solvate thereof in δ solvent, and cooling or adding π solvent to precipitate a solid, i.e., obtaining the co-crystal of the compound of formula (III), or the co-crystal of the solvate of the compound of formula (III).

The δ and π solvents are independently selected from the group consisting of ethyl acetate, methyl acetate, propyl acetate, methyl formate, ethyl formate, propyl formate, butyl formate, water, methanol, ethanol, propanol, isopropanol, butanol, ethylene glycol, propylene glycol, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, acetone, butanone, ethyl ether, propyl ether, isopropyl ether, n-pentane, n-hexane, petroleum ether, dichloromethane, chloroform or 1,2-dichloroethane, and mixtures thereof.

The powder X-ray diffraction pattern data of the polymorphs of the compound of formula (III) and the polymorphs of the solvates of the compound of formula (III) according to the present invention are as follows.

1. Peaks in Powder X-Ray Diffraction Pattern of Co-Crystal Φ-1 of Donepezil Hydrochloride and Maleic Acid

| Diffranction Angel (2θ, °) | Intensity (I/I$_0$) | Diffraction Angel (2θ, °) | Intensity (I/I$_0$) |
| --- | --- | --- | --- |
| 4.065 | 9.3 | 26.465 | 3.7 |
| 6.192 | 15.9 | 26.876 | 10.5 |
| 9.607 | 9.5 | 27.879 | 28.6 |
| 12.677 | 15.3 | 28.332 | 12.6 |
| 12.969 | 6.7 | 29.663 | 6.1 |
| 14.697 | 57.7 | 30.683 | 2.5 |
| 15.549 | 39.2 | 31.843 | 4.0 |
| 16.173 | 61.7 | 32.454 | 9.5 |
| 16.920 | 5.4 | 32.945 | 3.3 |
| 17.427 | 5.8 | 33.783 | 5.6 |
| 17.819 | 12.7 | 34.599 | 4.4 |
| 18.187 | 75.5 | 35.740 | 3.4 |
| 19.335 | 18.7 | 36.140 | 5.9 |
| 19.769 | 20.6 | 36.469 | 2.8 |
| 20.747 | 16.8 | 37.241 | 2.1 |
| 21.330 | 100 | 37.801 | 3.7 |
| 21.973 | 19.2 | 38.559 | 3.7 |
| 22.616 | 25.3 | 40.040 | 5.0 |
| 23.195 | 3.6 | 41.063 | 2.7 |
| 23.604 | 25.1 | 42.640 | 4.9 |
| 24.422 | 17.2 | 43.804 | 2.9 |
| 25.208 | 5.5 | 44.988 | 5.6 |
| 25.731 | 37.4 | | |

2. Peaks in Powder X-Ray Diffraction Pattern of Co-Crystal Φ-2 of Donepezil Hydrochloride and Fumaric Acid

| Diffranction Angel (2θ, °) | Intensity (I/I$_0$) | Diffraction Angel (2θ, °) | Intensity (I/I$_0$) |
| --- | --- | --- | --- |
| 6.233 | 28.7 | 28.343 | 9.9 |
| 9.640 | 7.5 | 29.748 | 8.9 |
| 10.132 | 3.8 | 29.982 | 3.3 |
| 12.729 | 13.8 | 30.569 | 1.3 |
| 12.959 | 4.0 | 31.908 | 3.9 |
| 13.438 | 1.0 | 32.447 | 8.1 |
| 13.963 | 4.3 | 32.968 | 2.8 |
| 14.722 | 44.4 | 33.809 | 4.8 |
| 15.464 | 3.8 | 34.663 | 3.4 |
| 16.186 | 36.8 | 35.719 | 1.9 |
| 17.805 | 16.1 | 36.180 | 5.1 |
| 18.199 | 58.4 | 37.741 | 2.1 |
| 19.234 | 10.9 | 38.551 | 3.3 |
| 19.818 | 28.5 | 39.274 | 4.3 |
| 20.675 | 22.4 | 40.061 | 10.4 |
| 21.352 | 100 | 41.159 | 1.3 |
| 22.018 | 21.7 | 42.347 | 1.7 |
| 22.642 | 13.8 | 42.680 | 4.5 |
| 23.598 | 20.4 | 43.800 | 2.5 |
| 24.420 | 14.5 | 44.969 | 4.3 |
| 25.300 | 2.0 | 46.493 | 1.6 |
| 25.765 | 34.1 | 47.687 | 1.1 |
| 26.919 | 17.2 | 48.828 | 1.8 |
| 27.941 | 35.3 | 49.611 | 2.0 |

3. Peaks in Powder X-Ray Diffraction Pattern of Co-Crystal Φ-3 of Donepezil Hydrochloride and Fumaric Acid

| Diffranction Angle (2θ, °) | Intensity (I/I$_0$) | Diffraction Angle (2θ, °) | Intensity (I/I$_0$) |
| --- | --- | --- | --- |
| 6.176 | 12.5 | 29.710 | 4.9 |
| 9.590 | 6.5 | 30.952 | 5.3 |
| 12.670 | 6.4 | 31.837 | 4.8 |
| 14.691 | 41.5 | 32.425 | 12.4 |
| 16.148 | 46.1 | 32.845 | 4.9 |
| 17.811 | 10.8 | 33.724 | 7.0 |
| 18.176 | 58.8 | 34.539 | 4.6 |
| 19.202 | 5.9 | 35.613 | 8.8 |
| 19.815 | 20.4 | 36.159 | 5.3 |
| 20.698 | 15.7 | 37.747 | 24.6 |
| 21.320 | 69.9 | 38.409 | 19.7 |
| 22.011 | 17.0 | 39.607 | 5.7 |
| 22.558 | 100 | 40.072 | 5.1 |
| 23.571 | 23.1 | 41.987 | 6.3 |
| 24.430 | 23.4 | 42.657 | 10.4 |
| 25.690 | 34.4 | 43.765 | 3.4 |
| 26.597 | 8.5 | 44.922 | 7.7 |
| 26.830 | 12.3 | 46.392 | 3.6 |
| 27.863 | 27.6 | 47.434 | 4.3 |
| 28.508 | 78.6 | 48.753 | 2.9 |
| 29.132 | 27.7 | | |

4. Peaks in Powder X-ray Diffraction Pattern of co-crystal Φ-4 of Donepezil Hydrochloride and Citric Acid

| Diffranction Angle (2θ, °) | Intensity (I/I$_0$) | Diffraction Angle (2θ, °) | Intensity (I/I$_0$) |
| --- | --- | --- | --- |
| 6.308 | 16.2 | 25.846 | 35.6 |
| 9.731 | 9.5 | 27.000 | 15.9 |
| 12.823 | 8.2 | 28.009 | 32.3 |
| 13.073 | 6.3 | 27.447 | 14.8 |
| 14.822 | 53.1 | 29.800 | 5.9 |
| 15.063 | 18.5 | 31.990 | 5.5 |
| 15.587 | 5.0 | 32.546 | 10.0 |

-continued

| Diffraction Angle (2θ, °) | Intensity (I/I₀) | Diffraction Angle (2θ, °) | Intensity (I/I₀) |
|---|---|---|---|
| 16.288 | 55.4 | 33.085 | 4.6 |
| 17.909 | 13.9 | 33.908 | 4.6 |
| 18.307 | 68.5 | 34.692 | 3.1 |
| 19.364 | 7.3 | 34.670 | 4.1 |
| 19.923 | 25.1 | 35.833 | 3.1 |
| 20.837 | 19.3 | 36.291 | 6.6 |
| 21.454 | 100 | 36.385 | 4.6 |
| 22.115 | 22.4 | 38.693 | 4.5 |
| 22.741 | 14.0 | 39.339 | 3.4 |
| 23.719 | 28.9 | 40.118 | 7.5 |
| 24.523 | 15.4 | 42.805 | 5.6 |
|  |  | 45.112 | 5.5 |

5. Peaks in Powder X-ray Diffraction Pattern of co-crystal Φ-5 of Donepezil Hydrochloride and Salicylic Acid

| Diffraction Angle (2θ, °) | Intensity (I/I₀) | Diffraction Angle (2θ, °) | Intensity (I/I₀) |
|---|---|---|---|
| 6.323 | 15.7 | 26.731 | 3.8 |
| 7.501 | 2.7 | 27.036 | 12.6 |
| 9.759 | 6.2 | 27.998 | 32.6 |
| 10.237 | 14.8 | 28.483 | 14.8 |
| 10.920 | 4.1 | 29.850 | 7.0 |
| 11.659 | 2.8 | 30.120 | 4.2 |
| 12.242 | 1.6 | 32.011 | 2.8 |
| 12.833 | 8.1 | 32.551 | 8.2 |
| 13.068 | 3.8 | 33.094 | 2.6 |
| 14.085 | 18.4 | 33.917 | 3.9 |
| 14.851 | 40.0 | 34.776 | 2.3 |
| 15.576 | 3.1 | 34.965 | 2.9 |
| 16.313 | 35.2 | 35.934 | 1.9 |
| 17.334 | 6.2 | 36.258 | 4.0 |
| 17.788 | 22.1 | 36.585 | 2.4 |
| 18.325 | 50.2 | 37.877 | 2.2 |
| 19.170 | 9.5 | 38.678 | 3.6 |
| 19.935 | 21.5 | 39.420 | 3.4 |
| 20.771 | 41.0 | 40.171 | 7.3 |
| 21.474 | 100 | 41.274 | 2.2 |
| 22.131 | 17.8 | 42.841 | 3.6 |
| 22.803 | 12.1 | 43.942 | 2.8 |
| 23.639 | 38.8 | 45.092 | 4.4 |
| 24.503 | 14.1 | 46.600 | 2.1 |
| 25.873 | 27.5 | 48.970 | 1.6 |

6. Peaks in Powder X-Ray Diffraction Pattern of Co-Crystal Φ-6 of Donepezil Hydrochloride and Tartaric Acid

| Diffraction Angle (2θ, °) | Intensity (I/I₀) | Diffraction Angle (2θ, °) | Intensity (I/I₀) |
|---|---|---|---|
| 6.313 | 16.9 | 27.007 | 13.9 |
| 9.727 | 10.3 | 28.012 | 28.0 |
| 12.827 | 10.2 | 28.465 | 12.7 |
| 13.084 | 9.0 | 29.826 | 5.6 |
| 14.818 | 61.8 | 30.103 | 3.2 |
| 15.049 | 17.9 | 31.971 | 4.9 |
| 15.577 | 5.8 | 32.556 | 9.5 |
| 16.285 | 63.9 | 33.107 | 3.2 |
| 17.283 | 3.8 | 33.858 | 4.7 |
| 17.928 | 15.0 | 34.729 | 3.3 |
| 18.297 | 79.1 | 35.866 | 2.9 |
| 19.424 | 6.8 | 36.275 | 4.4 |
| 19.934 | 24.5 | 36.442 | 3.6 |
| 20.831 | 19.8 | 37.889 | 3.3 |
| 21.446 | 100 | 38.650 | 3.1 |
| 22.104 | 25.4 | 39.365 | 2.7 |
| 22.732 | 14.1 | 40.203 | 4.1 |
| 23.722 | 27.9 | 42.815 | 3.3 |
| 24.524 | 16.9 | 45.068 | 4.5 |
| 25.837 | 32.7 |  |  |

7. Peaks in Powder X-Ray Diffraction Pattern of Co-Crystal Φ-7 of Donepezil Hydrochloride and Succinic Acid

| Diffraction Angle (2θ, °) | Intensity (I/I₀) | Diffraction Angle (2θ, °) | Intensity (I/I₀) |
|---|---|---|---|
| 6.300 | 39.7 | 28.028 | 36.9 |
| 9.716 | 6.0 | 28.448 | 8.5 |
| 12.793 | 19.7 | 29.800 | 10.8 |
| 14.806 | 38.2 | 31.011 | 1.9 |
| 15.540 | 2.6 | 31.360 | 2.6 |
| 16.271 | 27.7 | 32.065 | 3.6 |
| 17.263 | 1.7 | 32.532 | 7.6 |
| 17.907 | 14.8 | 33.055 | 2.4 |
| 18.294 | 48.0 | 33.904 | 5.3 |
| 19.327 | 18.1 | 34.753 | 3.3 |
| 19.890 | 30.8 | 35.826 | 2.0 |
| 20.750 | 16.5 | 36.244 | 6.8 |
| 21.440 | 100 | 37.862 | 2.3 |
| 21.808 | 13.4 | 38.605 | 4.0 |
| 22.086 | 19.1 | 39.386 | 5.1 |
| 22.728 | 13.4 | 40.132 | 12.7 |
| 23.720 | 15.2 | 42.826 | 4.6 |
| 24.520 | 11.9 | 43.923 | 2.4 |
| 25.838 | 40.0 | 45.036 | 3.9 |
| 26.992 | 22.4 | 46.598 | 1.7 |
|  |  | 48.950 | 1.7 |

The compound of formula (III), the solvates of the compound of formula (III), the co-crystals of the compound of formula (III), or the co-crystals of the solvates of the compound of formula (III) according to the present invention may be used as active ingredients to treat and/or ameliorate diseases, physiological dysfunctions and various pains caused by low level of acetylcholine, including but not limited to senile dementia (AD), attention deficient disorder of childhood, memory deterioration, paralysis agitans (demeritia), brain injury, multiple sclerosis, Down's Syndrome, delirium, mood disorder, Huntington's disease, and sleep disorder.

The compound of formula (III), the solvates of the compound of formula (III), the co-crystals of the compound of formula (III), or the co-crystals of the solvates of the compound of formula (III) according to the present invention may be used as active ingredients to treat various pains, including all discomforts involving a sense of pain, functional pain syndromes or organic pain syndromes, which include but are not limited to neuropathic headache, in particular migraine, primary fibromyalgia, amputation, tumoral denervation, traumatic denervation or pains caused by autoimmune mechanism.

Unit dosages of the compound of formula (III), the solvates of the compound of formula (III), the co-crystals of the compound of formula (III), or the co-crystals of the solvates of the compound of formula (III) according to the present invention when used as active ingredients are in the range of from 1.0 mg to 50 mg.

The present invention further discloses a pharmaceutical formulation comprising the compound of formula (III), the solvates of the compound of formula (III), the co-crystals of the compound of formula (III), or the co-crystals of the solvates of the compound of formula (III) which may be prepared from at least one of the above-mentioned components and a suitable excipient. The excipient includes a carrier, filler, solvent, diluent, colorant, and binder. The kind and amount of the excipient can be tailored depending on an administration route of the pharmaceutical formulation, such as oral, sublingual and buccal, intravenous, intraperitoneal, subcutaneous injection, intramuscular injection, intranasal, intraocular, inhalation, rectal, vaginal, transdermal administration, and the like.

The inventors of the present invention find that the compound of formula (I)

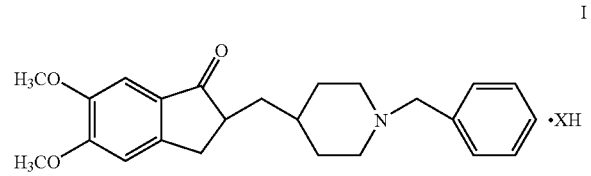

wherein XH represents methanesulfonic acid, benzenesulphonic acid, para-toluenesulfonic acid, salicylic acid, nitric acid, tartaric acid, citric acid, gallic acid, aspartic acid, glutamic acid, phosphoric acid, acetylsalicylic acid, lactic acid, gluconic acid, ascorbic acid, malonic acid, malic acid, sorbic acid, acetic acid, formic acid, fumaric acid, maleic acid, sulfuric acid, or succinic acid, has a good water-solubility; a tablet prepared therefrom has a release cuve similar to that of Donepezil hydrochloride tablet in artificial gastric fluid. Therefore, the compound of formula (I) is suitable for preparing an ordinary tablet.

Accordingly, the present invention further relates to a use of tablets or coated tablets comprising at least one of the compound of formula (I), the polymorphs of the compound of formula (I), the solvates of the compound of formula (I) and the polymorphs of the compound of formula (I), wherein XH represents methanesulfonic acid, benzenesulphonic acid, para-toluenesulfonic acid, salicylic acid, nitric acid, tartaric acid, citric acid, gallic acid, aspartic acid, glutamic acid, phosphoric acid, acetylsalicylic acid, lactic acid, gluconic acid, ascorbic acid, malonic acid, malic acid, sorbic acid, acetic acid, formic acid, fumaric acid, maleic acid, sulfuric acid, or succinic acid, in the preparation a medicament for the treatment of Alzheimer's disease (AD), hypomnesis, hyperkinetic syndrome of childhood, progressive cerebral atrophy, and parkinson's disease. A representative formulation of such dosage form comprises the following components expressed in weigh percentage.

| Compound of Formula (I): | 1-20% | Filler: | 35-90% |
|---|---|---|---|
| Disintegrant: | 1-30% | Flavoring Agent: | 0.01-5% |
| Lubricant: | 0.1-10% | Glidant: | 0.01-5% |
| Binder: | 0-5% | | |

The filler used in the tablets comprising at least one of the compound of formula (I), the polymorphs of the compound of formula (I), the solvates of the compound of formula (I) and the polymorphs of the compound of formula (I) according to the present invention is selected from the group consisting of starch, dextrin, lactose, sugar powder, glucose, mannitol, calcium sulphate, calcium hydrogen phosphate, tricalcium phosphate, microcrystalline cellulose, erythritol, and mixtures thereof.

The binder used in the tablets comprising at least one of the compound of formula (I), the polymorphs of the compound of formula (I), the solvates of the compound of formula (I) and the polymorphs of the compound of formula (I) according to the present invention is selected from the group consisting of water, starch, hydropropyl methylcellulose (HPMC), carboxymethylcellulose sodium (CMC-Na), hydropropyl cellulose (HPC), methylcellulose (MC), ethylcellulose (EC), polyvinylpyrrolidone (PVP), ethanol, and mixtures thereof.

The disintegrant used in the tablets comprising at least one of the compound of formula (I), the polymorphs of the compound of formula (I), the solvates of the compound of formula (I) and the polymorphs of the compound of formula (I) according to the present invention is selected from the group consisting of starch, modified starch, cellulose, alginic acid carboxymethylstarch sodium, microcrystalline cellulose, low substituted hydropropyl cellulose (L-HPC), carboxymethylstarch sodium, cross-linked polyvinylpyrrolidone (PVPP), cross-linked carboxymethylcellulose sodium (CCNa), cross-linked carboxymethylstarch sodium (CCMS-Na),treated agar (TAG), and mixtures thereof.

The flavoring agent used in the tablets comprising at least one of the compound of formula (I), the polymorphs of the compound of formula (I), the solvates of the compound of formula (I) and the polymorphs of the compound of formula (I) according to the present invention is selected from the group consisting of stevioside, aspartame, fruit essence, sodium cyclamate, sorbose, sucrose, glucose, menthol crystal, citric acid, ascorbic acid, and mixtures thereof.

The lubricant used in the tablets comprising at least one of the compound of formula (I), the polymorphs of the compound of formula (I), the solvates of the compound of formula (I) and the polymorphs of the compound of formula (I) according to the present invention is selected from the group consisting of magnesium stearate, talc powder, calcium stearate, stearic acid, hydrogenated vegetable oil, polyoxyethylene monostearate, light mineral oil, waxes, triacetin, polyethylene glycol 4000, polyethylene glycol 6000, magnesium lauryl sulfate, and mixtures thereof.

The glidant used in the tablets comprising at least one of the compound of formula (I), the polymorphs of the compound of formula (I), the solvates of the compound of formula (I) and the polymorphs of the compound of formula (I) according to the present invention is selected from the group consisting of micropowder silica gel, Cab-O-sil, Arosil, hydrated sodium aluminosilicate, and mixtures thereof.

The unit dosage of the tablets or the coated tablets comprising at least one of the compound of formula (I), the polymorphs of the compound of formula (I), the solvates of the compound of formula (I) and the polymorphs of the compound of formula (I) used as inhibitors of acetylcholinesterase may range from 0.5 mg to 50 mg, more preferably from 1 mg to 30 mg, most preferably from 2 mg to 20 mg.

The most convenient unit dosage of the tablets or the coated tablets comprising at least one of the compound of formula (I), the polymorphs of the compound of formula (I), the solvates of the compound of formula (I) and the polymorphs of the compound of formula (I) used as inhibitors of acetylcholinesterase is equivalent to 5 mg, 10 mg, or 20 mg of Donepezil hydrochloride.

Similarly, the compound of formula (III), the solvates of the compound of formula (III), the co-crystals of the compound of formula (III), and the co-crystals of the solvates of the compound of formula (III) according to the present invention may be formulated into ordinary tablets, oral liquids, granules, buccal tablets, orally disintegrating tablets, effervescent tablets, lyophilized rapid dissolving tablets, chewable tablets or capsules, and the like.

The unit dosage of the oral liquids, granules, buccal tablets, effervescent tablets, chewable tablets, orally disintegrating tablets, lyophilized rapid dissolving tablets, or ordinary tablets comprising at least one of the compound of formula (III), the solvates of the compound of formula (III), the co-crystals of the compound of formula (III), and the co-crystals of the solvates of the compound of formula (III) used as inhibitors of acetylcholinesterase may range from 0.5 mg to 50 mg, more preferably from 1 mg to 30 mg, most preferably from 2 mg to 20 mg.

The most convenient unit dosage of the oral liquids, granules, buccal tablets, effervescent tablets, chewable tablets, orally disintegrating tablets, lyophilized rapid dissolving tablets, or ordinary tablets comprising at least one of the compound of formula (III), the solvates of the compound of formula (I), the co-crystals of the compound of formula (III), and the co-crystals of the solvates of the compound of formula (III) used as inhibitors of acetylcholinesterase is equivalent to 5 mg, 10 mg, or 20 mg of Donepezil hydrochloride.

The representative formulation, the methods for preparation and the excipients used when formulating a compound of formula (III), a solvate of the compound of formula (III), a co-crystal of the compound of formula (III), or a co-crystal of the solvate of the compound of formula (III) into an ordinary tablet may be determined referring to those used when formulating a compound of formula (I) into an ordinary tablet.

However, the representative formulation, the methods for preparation and the excipients used when formulating the compound of formula (I) into an ordinary tablet are only specific examples to illustrate the formulations, the methods for preparation and the excipients used when formulating the compound of formula (III), the solvate of the compound of formula (III), the co-crystal of the compound of formula (III), or the co-crystal of the solvate of the compound of formula (III) into an ordinary tablet, and should not be interpreted as any limitation to the formulation of the ordinary tablet from the compound of formula (III), the solvate of the compound of formula (III), the co-crystal of the compound of formula (III), or the co-crystal of the solvate of the compound of formula (III) according to the present invention.

Any other formulations, methods for preparation and excipients used in ordinary tablets comprising at least one of the compound of formula (III), the solvate of the compound of formula (III), the co-crystal of the compound of formula (III), and the co-crystal of the solvate of the compound of formula (III) that a person skilled in the art may design in light of common knowledge are within the scope of the present invention.

The representative formulation, the methods for preparation and the excipients used when formulating a compound of formula (III), a solvate of the compound of formula (III), a co-crystal of the compound of formula (III), or a co-crystal of the solvate of the compound of formula (III) into oral liquids, granules, buccal tablets, effervescent tablets, chewable tablets, orally disintegrating tablets, or lyophilized rapid dissolving tablets may be determined referring to those used when formulating a compound of formula (II), a solvate of the compound of formula (II), a co-crystal of the compound of formula (II), or a co-crystal of the solvate of the compound of formula (II) into the oral liquids, granules, buccal tablets, effervescent tablets, chewable tablets, orally disintegrating tablets, or lyophilized rapid dissolving tablets.

However, the representative formulation, the methods for preparation and the excipients used when formulating the compound of formula (I) into oral liquids, granules, buccal tablets, effervescent tablets, chewable tablets, orally disintegrating tablets, or lyophilized rapid dissolving tablets are only specific examples to illustrate the formulations, the methods for preparation and the excipients used when formulating the compound of formula (III), the solvate of the compound of formula (III), the co-crystal of the compound of formula (III), or the co-crystal of the solvate of the compound of formula (III) into oral liquids, granules, buccal tablets, effervescent tablets, chewable tablets, orally disintegrating tablets, or lyophilized rapid dissolving tablets, and should not be interpreted as any limitation to the formulation of oral liquids, granules, buccal tablets, effervescent tablets, chewable tablets, orally disintegrating tablets, and lyophilized rapid dissolving tablets from the compound of formula (III), the solvate of the compound of formula (III), the co-crystal of the compound of formula (III), or the co-crystal of the solvate of the compound of formula (III) according to the present invention.

Any other formulations, methods for preparation and excipients used in oral liquids, granules, buccal tablets, effervescent tablets, chewable tablets, orally disintegrating tablets, or lyophilized rapid dissolving tablets comprising at least one of the compound of formula (III), the solvate of the compound of formula (III), the co-crystal of the compound of formula (III), and the co-crystal of the solvate of the compound of formula (III) that a person skilled in the art may design in light of common knowledge are within the scope of the present invention.

Taste Test: Seven volunteers are buccally administered a solution of 2 mg of active ingredient in 1 ml of deionized water or an orally disintegrating tablet containing 5 mg of active ingredient and a flavoring agent. The taste is ranked as follows: utmost-bitter: ++++, highly-bitter: +++, quite-bitter: ++, bitter: +, slightly-bitter ±, non-bitter: −.

When the ranking results are evaluated, the taste is ranked non-bitter only when all of the seven volunteers rank it non-bitter; the taste is ranked slightly-bitter if less than 4 volunteers rank it slightly-bitter and other volunteers rank it non-bitter. Test results are shown in Table 1.

TABLE 1

Taste Test Results for Donepezil salts and orally disintegrating tablets thereof

| Samples | Active ingredient | Tablet | Description |
|---|---|---|---|
| Example 42 | − | − | non-bitter |
| Example 53 | − | − | non-bitter |
| Example 58 | ++ | ++ | bitter |
| Example 66 | ++ | ± | slightly-bitter |
| Example 91 | ++ | ++ | bitter |
| Example 48 | ++ | +++ | highly-bitter, sour |
| Example 11 | ++++ | +++ | highly-bitter, acerbic, tongue is numb |
| Example 1 | +++++ | +++++ | utmost-bitter, tongue is numb |
| Example 93 | + | ± | slightly-bitter after tabletting |
| Example 92 | − | − | non-bitter |
| Example 99 | +++ | +++ | highly-bitter |
| Example 28 | +++ | +++ | sour, highly-bitter |
| Example 94 | +++ | Not tabletting | highly-bitter |
| Example 95 | +++ | Not tabletting | sour, highly-bitter |
| Example 96 | +++ | Not tabletting | highly-bitter |
| Example 84 | +++ | Not tabletting | highly-bitter |
| Example 97 | +++ | Not tabletting | highly-bitter |
| Example 98 | − | − | non-bitter |
| Example 37 | ++ | + | slightly-bitter after tabletting |

TABLE 1-continued

Taste Test Results for Donepezil salts and orally disintegrating tablets thereof

| Samples | Active ingredient | Tablet | Description |
|---|---|---|---|
| Example 100 | +++ | Not tabletting | highly-bitter |
| Example 101 | +++ | Not tabletting | highly-bitter |
| Example 102 | +++ | Not tabletting | highly-bitter |
| Example 16 | ++ | ++ | bitter |
| Example 86 | +++ | Not tabletting | tongue is numb, highly-bitter |
| Example 103 | +++ | Not tabletting | highly-bitter |

Note:
Degrees of bitterness and acerbity of the taste are represented by numbers of "+". "−" represents non-bitter, "±" represents a slightly bitter.

The present invention further discloses a pharmaceutical formulation comprising the compound of formula (I), the polymorph of the compound of formula (I), the solvate of the compound of formula (I), or the polymorph of the solvate of the compound of formula (I), which are formulated from at least one of the compound of formula (I), the polymorph of the compound of formula (I), the solvate of the compound of formula (I), and the polymorph of the solvate of the compound of formula (I) and a suitable excipient. The excipient includes a carrier, filler, solvent, diluent, colorant, and binder. The kind and amount of the excipient may be tailored according to the administration route of the pharmaceutical formulation, such as oral, sublingual and buccal, intravenous, intraperitoneal, subcutaneous injection, intramuscular injection, intranasal, intraocular, inhalation, rectal, vaginal, transdermal administration, and the like.

A tabletting process and dissolution test of a tablet comprising the polymorph (I-A) of Donepezil mesylate according to the present invention Formulation: Compound I-A 1.14 g; water-soluble starch 6 g; microcrystalline cellulose 4 g; lactose 7.46 g; low-substituted HPMC 0.8 g; 1% HPMC 10 ml; magnesium stearate 0.6 g.

Preparing process: The active ingredient and the excipients are sieved with a 80-mesh screen, weighted according to the formulation, and mixed uniformly. 1% HPMC is added portion-wisely to form a soft material, and the soft material is granulated with a 24-mesh screen. The resulted particles are dried for 2.5 hours in a drying oven at 60° C. and sized with 30-mesh screen. Based on the amount of the particles actually measured, magnesium stearate is added proportionally. The materials are mixed uniformly and tabletted.

Diameter of puncher: 6 mm; tablet weight: 100±2 mg.

Dissolution test is performed on a RC806 dissolution tester

Six tablets are used as samples and the test is performed according to the second method of dissolution test specified in the US Pharmacopoeia. The dissolution media is 900 ml of de-gassed water; the temperature is 37° C.; the rotation rate is 100 rpm. 1 ml of samples is withdrawn at 5 min, 10 min, 15 min, 20 min, respectively, and no additional dissolution media is added. The samples are filtered by a 0.45 micropore film and 90 μl of sample is injected to test. The test results are shown in FIG. 13

The elemental analysis results of compounds Φ-1~Φ-7 of the compounds of formula (III) according to the present invention are shown as follows:

| | C/% | | | H/% | | | N/% | | | Cl/% | | Donepezil:HCl:organic acid:water |
|---|---|---|---|---|---|---|---|---|---|---|---|---|
| | | Measured | | | Measured | | | Measured | | | | |
| Numbers | Calcd. | 1 | 2 | Calcd. | 1 | 2 | Calcd. | 1 | 2 | Calcd. | Measured | |
| Example 115 | 68.21 | 68.47 | 68.29 | 7.10 | 7.50 | 7.46 | 3.19 | 3.25 | 3.34 | 6.05 | 5.97 | 4:3:1:1 |
| Example 116 | 68.91 | 68.74 | 68.59 | 7.06 | 6.99 | 7.15 | 3.22 | 3.28 | 3.31 | 6.12 | 6.19 | 4:3:1:0 |
| Example 117 | 57.7 | 58.27 | 58.32 | 6.01 | 6.14 | 6.30 | 2.10 | 2.14 | 2.22 | 5.33 | 4.62 | 1:1:2:0 |
| Example 118 | 66.61 | 66.12 | 66.30 | 7.02 | 7.15 | 7.22 | 3.05 | 2.83 | 2.79 | 5.80 | 5.24 | 4:3:1:1 |
| Example 119 | 70.70 | 69.99 | 70.05 | 6.96 | 7.24 | 7.32 | 3.00 | 2.90 | 2.84 | 3.8 | 3.10 (interfered) | 2:1:1:0 |
| Example 120 | 66.17 | 65.47 | 65.55 | 7.11 | 7.57 | 7.67 | 3.09 | 2.98 | 2.79 | 5.87 | 6.10 | 4:3:1:2 |
| Example 121 | 67.34 | 66.78 | 66.95 | 7.07 | 6.34 | 6.44 | 3.14 | 2.92 | 2.68 | 7.97 | 7.99 | 4:4:1:0 |

Measurement of chlorine content: A proper amount of sample is dissolved in water under sonication. Dilute nitric acid is added to acidify the solution, and an excess amount of 0.1 M silver nitrate titration solution is added. The precipitate is filtered off, and a proper amount of a solution of 8% $NH_4Fe(SO_4)_4$ is added to the filtrate as an indicator. The excess amount of silver nitrate is titrated with 0.1 M $NH_4SCN$ titration solution, and the consumed amount of $Ag^+$ is calculated to determine the chlorine content in the sample.

Unless otherwise indicated, the solvent used in the nuclear magnetic resonance test in the present invention is $D_2O$.

EXAMPLES

Example 1

Donepezil Mesylate (I)

3.79 g of Donepezil is dissolved in 70 ml of ethyl acetate, and a solution of methanesulfonic acid (0.65 ml) in absolute ethanol (35 ml) is slowly added with stirring at room temperature. The solid precipitated is filtered and dried at 55° C. under vacuum to give the title compound. Melting point: 181.9° C.

Example 2

Donepezil Mesylate (I)

Methanesulfonic acid (0.65 ml, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound. Melting point: 181.1° C.

Example 3

Donepezil Mesylate (I)

Methanesulfonic acid (0.65 ml, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound. Melting point: 182.2° C.

Example 4

Donepezil Mesylate (I)

3.79 g of Donepezil is dissolved in 80 ml of acetone, and 10 ml of a solution of methanesulfonic acid in absolute ethanol is slowly added. The solid precipitated is filtered to give the title compound, which is dried at 55° C. under vacuum. Melting point: 181.6° C.

Example 5

Polymorph (I-A) of Donepezil Mesylate

Donepezil mesylate (any form) is dissolved in a proper amount of absolute ethanol with heating. The resulted solution is slowly cooled and the crystal precipitated is filtered and dried at 55° C. under vacuum to give the title compound. Melting point: 182.6° C.

Example 6

Polymorph (I-A) of Donepezil Mesylate

Donepezil mesylate (any form) is dissolved in a proper amount of absolute ethanol with heating. A proper amount of dipropyl ether is added to make the solution slightly turbid. The solution is further heated to become clear again, and is then slowly cooled. The crystal precipitated is filtered and dried at 55° C. under vacuum to give the title compound. Melting point: 182.6° C.

Example 7

Polymorph (I-A) of Donepezil Mesylate

Donepezil mesylate (any form) is dissolved in a proper amount of absolute ethanol with heating. A proper amount of n-hexane is added to make the solution slightly turbid. The solution is further heated to become clear again, and is then slowly cooled. The crystal precipitated is filtered and dried at 55° C. under vacuum to give the title compound. Melting point: 181.5° C.

Example 8

Polymorph (I-A) of Donepezil Mesylate

Methanesulfonic acid (0.65 ml, dissolved in 35 ml of acetone) is slowly added to a solution of Donepezil (3.79 g) in ethyl acetate (70 ml) with stirring at room temperature. The solid precipitated is filtered immediately and dried at 55° C. under vacuum to give the title compound. Melting point: 180.1° C.

Example 9

Polymorph (I-A) of Donepezil Mesylate

Methanesulfonic acid (1.3 ml, dissolved in 11 ml of absolute ethanol) is slowly added to a solution of Donepezil (3.79 g) in absolute ethanol (38 ml) with stirring at room temperature, and 50 ml of dipropyl ether is added. The solid precipitated is filtered and dried at 55° C. under vacuum to give the title compound. Melting point: 180.3° C.

Example 10

Polymorph (I-A) of Donepezil Mesylate

Methanesulfonic acid (1.3 ml, dissolved in 11 ml of absolute ethanol and 50 ml of dipropyl ether) is slowly added to a solution of Donepezil (3.79 g) in absolute ethanol (38 ml) with stirring at room temperature. The mixed solution is stirred at room temperature and the solid precipitated is filtered and dried 55° C. under vacuum to give the title compound. Melting point: 177.4° C.

Example 11

Donepezil Para-Toluenesulfonate (II)

Para-toluenesulfonic acid (1.902 g, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 170.8° C.

Example 12

Donepezil Para-Toluenesulfonate (II)

Para-toluenesulfonic acid (1.902 g, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound. Melting point: 170.8° C.

Example 13

Donepezil Para-Toluenesulfonate (II)

Para-toluenesulfonic acid (1.902 g, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound. Melting point: 170.8° C.

Example 14

Polymorph (II-A) of Donepezil Para-Toluenesulfonate

Donepezil para-toluenesulfonate (any form) is dissolved in a proper amount of absolute ethanol with heating, and the solution is then slowly cooled. The crystal precipitated is filtered and dried at 55° C. under vacuum to give the title compound. Melting point: 171.0° C.

Example 15

Polymorph (II-A) of Donepezil Para-Toluenesulfonate

Donepezil para-toluenesulfonate (any form) is dissolved in a proper amount of absolute ethanol with heating. A proper amount of dipropyl ether is added to make the solution slightly turbid. The solution is further heated to become clear again, and is then slowly cooled. The crystal precipitated is filtered and dried at 55° C. under vacuum to give the title compound. Melting point: 170.3° C.

Example 16

Donepezil Succinate (III)

Succinic acid (1.18 g, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 169.1° C.

Example 17

Donepezil Succinate (III)

Succinic acid (1.18 g, dissolved in 35 ml of acetone and 5 ml of water) is slowly added to a solution of Donepezil (3.79 g) in ethyl acetate (70 ml) with stirring at room temperature. The solid precipitated is filtered and dried at 55° C. under vacuum to give the title compound. Melting point: 168.0° C.

Example 18

Donepezil Succinate (III)

Succinic acid (1.18 g, dissolved in 35 ml of acetone and 5 ml of water) is slowly added to a solution of Donepezil (3.79 g) in tetrahydrofuran (70 ml) with stirring at room temperature. The solid precipitated is filtered and dried at 55° C. under vacuum to give the title compound. Melting point: 168.7° C.

Example 19

Donepezil Succinate (III)

Succinic acid (1.18 g, dissolved in 35 ml of 2-propanol and 5 ml of water) is slowly added to a solution of Donepezil (3.79 g) in ethyl acetate (70 ml) with stirring at room temperature. The solid precipitated is filtered and dried at 55° C. under vacuum to give the title compound. Melting point: 165.7° C.

Example 20

Donepezil Succinate (III)

Donepezil (3.79 g, dissolved in 70 ml of ethyl acetate) is slowly added to a solution of succinic acid (0.59 g) in absolute ethanol (35 ml) with stirring at room temperature. The solid precipitated is filtered and dried at 55° C. under vacuum to give the title compound. Melting point: 169.5° C.

Example 21

Donepezil Succinate (III)

Donepezil (3.79 g, dissolved in 70 ml of ethyl acetate) is slowly added to a solution of succinic acid (0.59 g) in acetone (35 ml) and water (5 ml) with stirring at room temperature. The solid precipitated is filtered and dried at 55° C. under vacuum to give the title compound. Melting point: 169.2° C.

Example 22

Donepezil Succinate (III)

Donepezil (3.79 g, dissolved in 70 ml of ethyl acetate) is slowly added to a solution of succinic acid (0.59 g) in 2-propanol (35 ml) and water (5 ml) with stirring at room temperature. The solid precipitated is filtered and dried at 55° C. under vacuum to give the title compound. Melting point: 167.5° C.

Example 23

Polymorph (III-A) of Donepezil Succinate

Donepezil succinate (any form) is dissolved in a proper amount of absolute ethanol with heating, and the solution is then slowly cooled. The crystal precipitated is filtered and dried at 55° C. under vacuum to give the title compound. Melting point: 169.6° C.

Example 24

Polymorph (III-A) of Donepezil Succinate

Donepezil succinate (any form) is dissolved in a proper amount of absolute ethanol with heating. A proper amount of n-hexane is added to make the solution slightly turbid. The solution is further heated to become clear again, and is then slowly cooled. The crystal precipitated is filtered and dried at 55° C. under vacuum to give the title compound. Melting point: 168.4° C.

Example 25

Polymorph (III-A) of Donepezil Succinate

Donepezil succinate (any form) is dissolved in a proper amount of absolute ethanol with heating. A proper amount of distilled water is added to make the solution slightly turbid. The solution is further heated to become clear again, and is then slowly cooled. The crystal precipitated is filtered and dried at 55° C. under vacuum to give the title compound. Melting point: 168.8° C.

Example 26

Polymorph (III-A) of Donepezil Succinate

Donepezil succinate (any form) is dissolved in a proper amount of acetone-water mixture with heating, and the resulted solution is slowly cooled. The crystal precipitated is filtered and dried at 55° C. under vacuum to give the title compound. Melting point: 170.2° C.

Example 27

Polymorph (III-A) of Donepezil Succinate

Donepezil succinate (any form) is dissolved in a proper amount of 2-propanol with heating, and the resulted solution slowly cooled. The crystal precipitated is filtered and dried at 55° C. under vacuum to give the title compound. Melting point: 169.3° C.

Example 28

Donepezil Tartrate (IV)

Tartaric acid (1.5 g, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 169.6° C.

Example 29

Donepezil Tartrate (IV)

Tartaric acid (1.5 g, dissolved in 35 ml of acetone) is slowly added to a solution of Donepezil (3.79 g) in ethyl acetate (200 ml) with stirring at room temperature. The solid precipitated is filtered and dried at 55° C. under vacuum to give the title compound.

Example 30

Donepezil Tartrate (IV)

Tartaric acid (1.5 g, dissolved in 35 ml of 2-propanol-water mixture) is slowly added to a solution of Donepezil (3.79 g) in ethyl acetate (70 ml) with stirring at room temperature. The mixture is stirred for 3 hours at room temperature and concentrated at vacuum to give the title compound.

Example 31

Donepezil Tartrate (IV)

Donepezil (3.79 g, dissolved in 70 ml of ethyl acetate) is slowly added to a solution of tartaric acid (0.75 g) in absolute ethanol (35 ml) with stirring at room temperature. The solid precipitated is filtered and dried at 55° C. under vacuum to give the title compound. Melting point: 168.0° C.

Example 32

Donepezil Tartrate (IV)

Donepezil (3.79 g, dissolved in 200 ml of ethyl acetate) is slowly added to a solution of tartaric acid in acetone (35 ml) with stirring at room temperature. The solid precipitated is filtered and dried at 55° C. under vacuum to give the title compound.

Example 33

Donepezil Tartrate (IV)

Tartaric acid (1.18 g, dissolved in 7 ml of water) is slowly added to a solution of Donepezil (3.79 g) in absolute ethanol (70 ml) with stirring at room temperature. The solid precipitated is filtered and dried at 55° C. under vacuum to give the title compound.

Example 34

Donepezil Tartrate (IV)

Donepezil (3.79 g, dissolved in 70 ml of ethyl acetate) is slowly added to a solution of tartaric acid (0.75 g) in 2-propanol (35 ml) with stirring at room temperature. The mixture is stirred for 3 hours at room temperature and concentrated at vacuum to give the title compound.

Example 35

Polymorph (IV-A) of Donepezil Tartrate

Donepezil tartrate (any form) is dissolved in a proper amount of acetone with heating, and the resulted solution is then slowly cooled. The crystal precipitated is filtered and dried at 55° C. under vacuum to give the title compound. Melting point: 164.5° C.

Example 36

Polymorph (IV-A) of Donepezil Tartrate

Donepezil tartrate (any form) is dissolved in a proper amount of 2-propanol with heating, and the resulted solution is then slowly cooled. The crystal precipitated is filtered and dried at 55° C. under vacuum to give the title compound. Melting point: 161.6° C.

Example 37

Donepezil Sulphate (V)

Sulfuric acid (0.53 ml, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound.

Example 38

Donepezil Sulphate (V)

Sulfuric acid (0.53 ml, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound.

Example 39

Donepezil Sulphate (V)

Sulfuric acid (0.53 ml, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound.

Example 40

Polymorph (V-A) of Donepezil Sulphate

Donepezil sulphate (any form) is dissolved in a proper amount of absolute ethanol with heating, and the resulted solution is then slowly cooled. The crystal precipitated is filtered and dried at 55° C. under vacuum to give the title compound. Melting point: 175.1° C.

Example 41

Polymorph (V-B) of Donepezil Sulphate

Donepezil sulphate (any form) is dissolved in a proper amount of absolute ethanol with heating. A proper amount of dipropyl ether is added to make the solution slightly turbid. The solution is further heated to become clear again, and is then slowly cooled. The crystal precipitated is filtered and dried at 55° C. under vacuum to give the title compound. Melting point: 130.5° C.

Example 42

Donepezil Nitrate (VI)

Nitric acid (0.45 ml, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 213.7° C.

Example 43

Donepezil Nitrate (VI)

Nitric acid (0.45 ml, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound. Melting point: 212.8° C.

Example 44

Donepezil Nitrate (VI)

Nitric acid (0.45 ml, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound. Melting point: 213.7° C.

Example 45

Polymorph (VI-A) of Donepezil Nitrate

Donepezil nitrate (any form) is dissolved in a proper amount of absolute ethanol-water mixture with heating, and the resulted solution is then slowly cooled. The crystal precipitated is filtered and dried at 55° C. under vacuum to give the title compound. Melting point: 215.8° C.

Example 46

Polymorph (VI-A) of Donepezil Nitrate

Donepezil nitrate (any form) is dissolved in a proper amount of acetone-water mixture with heating, and the resulted solution is then slowly cooled. The crystal precipitated is filtered and dried at 55° C. under vacuum to give the title compound. Melting point: 213.5° C.

Example 47

Polymorph (VI-A) of Donepezil Nitrate

Donepezil nitrate (any form) is dissolved in a proper amount of 2-propanol-water mixture with heating, and the resulted solution is then slowly cooled. The crystal precipitated is filtered and dried at 55° C. under vacuum to give the title compound. Melting point: 216.3° C.

Example 48

Donepezil Phosphate (VII)

Phosphoric acid (0.58 ml, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound.

Example 49

Donepezil Phosphate (VII)

Phosphoric acid (0.58 ml, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound.

Example 50

Donepezil Phosphate (VII)

Donepezil (3.79 g, dissolved in 70 ml of ethyl acetate) is slowly added to a solution of phosphoric acid (0.29 ml) in acetone (35 ml) with stirring at room temperature. The solid precipitated is filtered and dried at 55° C. under vacuum to give the title compound.

Example 51

Donepezil Phosphate (VII)

Donepezil (3.79 g, dissolved in 70 ml of ethyl acetate) is slowly added to a solution of phosphoric acid (0.29 ml) in 2-propanol (35 ml) with stirring at room temperature. The solid precipitated is filtered and dried at 55° C. under vacuum to give the title compound.

Example 52

Polymorph (VII-A) of Donepezil Phosphate

Donepezil phosphate (any form) is dissolved in a proper amount of 2-propanol with heating. A proper amount of dipropyl ether is added to make the solution slightly turbid. The solution is further heated to become clear again, and is then slowly cooled. The crystal precipitated is filtered and dried at 55° C. under vacuum to give the title compound. Melting point: 156.5° C.

Example 53

Donepezil Salicylate (VIII)

Salicylic acid (1.38 g, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 176.5° C.

Example 54

Donepezil Salicylate (VIII)

Salicylic acid (1.38 g, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound. Melting point: 175.8° C.

Example 55

Donepezil Salicylate (VIII)

Salicylic acid (1.38 g, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound. Melting point: 174.5° C.

Example 56

Polymorph (VIII-A) of Donepezil Salicylate

Donepezil salicylate (any form) is dissolved in a proper amount of acetone-water mixture with heating, and the resulted solution is then slowly cooled. The crystal precipitated is filtered and dried at 55° C. under vacuum to give the title compound. Melting point: 175.5° C.

Example 57

Polymorph (VIII-A) of Donepezil Salicylate

Donepezil salicylate (any form) is dissolved in a proper amount of 2-propanol-water mixture with heating, and the resulted solution is then slowly cooled. The crystal precipitated is filtered and dried at 55° C. under vacuum to give the title compound. Melting point: 174.8° C.

Example 58

Donepezil Fumarate (IX)

Fumaric acid (1.16 g, dissolved in 35 ml of absolute ethanol) is slowly added to a solution of Donepezil (3.79 g) in ethyl acetate (70 ml) with stirring at room temperature. The solid precipitated is filtered and dried at 55° C. under vacuum to give the title compound. Melting point: 167.7° C.

Example 59

Donepezil Fumarate (IX)

Fumaric acid (1.16 g, dissolved in 35 ml of acetone) is slowly added to a solution of Donepezil (3.79 g) in ethyl acetate (70 ml) with stirring at room temperature. The solid precipitated is filtered and dried at 55° C. under vacuum to give the title compound. Melting point: 170.1° C.

Example 60

Donepezil Fumarate (IX)

Fumaric acid (1.16 g, dissolved in 35 ml of 2-propanol) is slowly added to a solution of Donepezil (3.79 g) in ethyl acetate (70 ml) with stirring at room temperature. The solid precipitated is filtered and dried at 55° C. under vacuum to give the title compound. Melting point: 168.5° C.

Example 61

Donepezil Fumarate (IX)

Donepezil (3.79 g, dissolved in 70 ml of ethyl acetate) is slowly added to a solution of fumaric acid (0.58 g) in absolute ethanol (35 ml) with stirring at room temperature. The solid precipitated is filtered and dried at 55° C. under vacuum to give the title compound. Melting point: 166.9° C.

Example 62

Donepezil Fumarate (IX)

Donepezil (3.79 g, dissolved in 70 ml of ethyl acetate) is slowly added to a solution of fumaric acid (0.58 g) in acetone (35 ml) with stirring at room temperature. The solid precipitated is filtered and dried at 55° C. under vacuum to give the title compound. Melting point: 167.4° C.

Example 63

Donepezil Fumarate (IX)

Donepezil (3.79 g, dissolved in 70 ml of ethyl acetate) is slowly added to a solution of fumaric acid (0.58 g) in 2-propanol (35 ml) with stirring at room temperature. The solid precipitated is filtered and dried at 55° C. under vacuum to give the title compound. Melting point: 173.1° C.

Example 64

Polymorph (IX-A) of Donepezil Fumarate

Donepezil fumarate (any form) is dissolved in a proper amount of absolute ethanol with heating, and the resulted solution is then slowly cooled. The crystal precipitated is filtered and dried at 55° C. under vacuum to give the title compound. Melting point: 170.4° C.

Example 65

Polymorph (IX-A) of Donepezil Fumarate

Donepezil fumarate (any form) is dissolved in a proper amount of 2-propanol with heating, and the resulted solution is then slowly cooled. The crystal precipitated is filtered and dried at 55° C. under vacuum to give the title compound. Melting point: 170.0° C.

Example 66

Donepezil Maleate (X)

Maleic acid (1.161 g, dissolved in 35 ml of absolute ethanol) is slowly added to a solution of Donepezil (3.79 g) in ethyl acetate (70 ml) with stirring at room temperature. The mixture is stirred for 3 hours at room temperature and concentrated at vacuum to give the title compound.

Example 67

Donepezil Maleate (X)

Maleic acid (1.161 g, dissolved in 35 ml of acetone) is slowly added to a solution of Donepezil (3.79 g) in ethyl acetate (70 ml) with stirring at room temperature. The mixture is stirred for 3 hours at room temperature and concentrated at vacuum to give the title compound.

Example 68

Donepezil Maleate (X)

Maleic acid (1.161 g, dissolved in 35 ml of 2-propanol) is slowly added to a solution of Donepezil (3.79 g) in ethyl acetate (70 ml) with stirring at room temperature. The mixture is stirred for 3 hours at room temperature and concentrated at vacuum to give the title compound.

Example 69

Donepezil Maleate (X)

Donepezil (3.79 g, dissolved in 70 ml of ethyl acetate) is slowly added to a solution of maleic acid (0.58 g) in absolute ethanol (35 ml) with stirring at room temperature. The mixture is stirred for 3 hours at room temperature and concentrated at vacuum to give the title compound.

Example 70

Donepezil Maleate (X)

Donepezil (3.79 g, dissolved in 70 ml of ethyl acetate) is slowly added to a solution of maleic acid (0.58 g) in acetone (35 ml) with stirring at room temperature. The mixture is stirred for 3 hours at room temperature and concentrated at vacuum to give the title compound.

Example 71

Donepezil Maleate (X)

Donepezil (3.79 g, dissolved in 70 ml of ethyl acetate) is slowly added to a solution of maleic acid (0.58 g) in 2-propanol (35 ml) with stirring at room temperature. The mixture is stirred for 3 hours at room temperature and concentrated at vacuum to give the title compound.

Example 72

Donepezil Maleate (X)

Maleic acid (1.161 g, dissolved in 10 ml of absolute ethanol) is slowly added to a solution of Donepezil (3.79 g) in ethyl acetate (20 ml) with stirring at room temperature followed by adding 10 ml of dipropyl ether. The solid precipitated is filtered and dried at 55° C. under vacuum to give the title compound. Melting point: 132.2° C.

Example 73

Donepezil Maleate (X)

Maleic acid (1.161 g, dissolved in 10 ml of acetone) is slowly added to a solution of Donepezil (3.79 g) in ethyl acetate (20 ml) with stirring at room temperature. The solid precipitated is filtered and dried at 55° C. under vacuum to give the title compound.

Example 74

Donepezil Maleate (X)

Maleic acid (1.161 g, dissolved in 10 ml of 2-propanol) is slowly added to a solution of Donepezil (3.79 g) in ethyl acetate (20 ml) with stirring at room temperature followed by adding 10 ml of dipropyl ether. The solid precipitated is filtered and dried at 55° C. under vacuum to give the title compound. Melting point: 126.8° C.

Example 75

Donepezil Maleate (X)

Donepezil (3.79 g, dissolved in 20 ml of ethyl acetate) is slowly added to a solution of maleic acid (0.58 g) in absolute ethanol (5 ml) with stirring at room temperature followed by adding 10 ml of dipropyl ether. The solid precipitated is filtered and dried at 55° C. under vacuum to give the title compound. Melting point: 127.8° C.

Example 76

Donepezil Maleate (X)

Donepezil (3.79 g, dissolved in 20 ml of ethyl acetate) is slowly added to a solution of maleic acid (0.58 g) in acetone (5 ml) with stirring at room temperature. The solid precipitated is filtered and dried at 55° C. under vacuum to give the title compound. Melting point: 130.3° C.

Example 77

Donepezil Maleate (X)

Donepezil (3.79 g, dissolved in 20 ml of ethyl acetate) is slowly added to a solution of maleic acid (0.58 g) in 2-propanol (5 ml) with stirring at room temperature. The solid precipitated is filtered and dried at 55° C. under vacuum to give the title compound. Melting point: 129.5° C.

Example 78

Polymorph (X-A) of Donepezil Maleate

Donepezil maleate (the ratio of Donepezil to maleic acid is 1:1) is dissolved in a proper amount of absolute ethanol with heating, and the resulted solution is then slowly cooled. The crystal precipitated is filtered and dried at 55° C. under vacuum to give the title compound. Melting point: 130.1° C.

Example 79

Polymorph (X-A) of Donepezil Maleate

Donepezil maleate (the ratio of Donepezil to maleic acid is 1:1) is dissolved in a proper amount of acetone with heating, and the resulted solution is then slowly cooled. The crystal precipitated is filtered and dried at 55° C. under vacuum to give the title compound. Melting point: 132.4° C.

Example 80

Polymorph (X-A) of Donepezil Maleate

Donepezil maleate (the ratio of Donepezil to maleic acid is 1:1) is dissolved in a proper amount of 2-propanol with heating, and the resulted solution is then slowly cooled. The crystal precipitated is filtered and dried at 55° C. under vacuum to give the title compound.

Example 81

Polymorph (X-A) of Donepezil Maleate

Donepezil maleate (the ratio of Donepezil to maleic acid is 2:1) is dissolved in a proper amount of absolute ethanol with heating, and the resulted solution is then slowly cooled. The crystal precipitated is filtered and dried at 55° C. under vacuum to give the title compound. Melting point: 130.5° C.

Example 82

Polymorph (X-B) of Donepezil Maleate

Donepezil maleate (the ratio of Donepezil to maleic acid is 2:1) is dissolved in a proper amount of acetone with heating, and the resulted solution is then slowly cooled. The crystal precipitated is filtered and dried at 55° C. under vacuum to give the title compound. Melting point: 131.1° C.

Example 83

Polymorph (X-B) of Donepezil Maleate

Donepezil maleate (the ratio of Donepezil to maleic acid is 2:1) is dissolved in a proper amount of 2-propanol with heating, and the resulted solution is then slowly cooled. The crystal precipitated is filtered and dried at 55° C. under vacuum to give the title compound.

Example 84

Donepezil Malate (XI)

1.901 g of Donepezil is dissolved in 15 ml of ethyl acetate. A solution (4 ml) of malic acid (0.679 g) in absolute ethanol is added slowly and drop-wisely and the resulted solution is stirred. The solid precipitated is filtered with suction to give the title compound.

Example 85

Polymorph (XI-A) of Donepezil Malate 3.206 g of Donepezil malate is dissolved in 10 ml of absolute ethanol and the resulted solution is heated to become clear. The solution is cooled to precipitate a solid of the title compound.

Example 86

Donepezil Benzenesulphonate (XII)

3.790 g of Donepezil is dissolved in 70 ml of ethyl acetate. A solution (35 ml) of benzenesulfonic acid (1.852 g) in absolute ethanol is added slowly and drop-wisely. The solid precipitated is filtered under suction to give the title compound.

Example 87

Donepezil Benzenesulphonate (XII)

3.790 g of Donepezil is dissolved in 70 ml of ethyl acetate. A solution (35 ml) of benzenesulfonic acid (1.852 g) in acetone is slowly added drop-wisely. The solid precipitated is filtered under suction to give the title compound.

Example 88

Donepezil Benzenesulphonate (XII)

3.790 g of Donepezil is dissolved in 70 ml of ethyl acetate. A solution (35 ml) of benzenesulfonic acid (1.852 g) in iso-propanol is added slowly and drop-wisely. The solid precipitated is filtered under suction to give the title compound.

Example 89

Donepezil Benzenesulphonate (XII)

3.790 g of Donepezil is dissolved in 20 ml of ethanol. A solution (35 ml) of benzenesulfonic acid (1.852 g) in acetone is added slowly and drop-wisely. The solid precipitated is filtered with suction to give the title compound.

Example 90

Polymorph (XII-A) of Donepezil benzenesulphonate 3.790 g of Donepezil is dissolved in 70 ml of ethyl acetate. A solution (35 ml) of benzenesulfonic acid (1.852 g) in acetone is added slowly and drop-wisely. The solid precipitated is filtered under suction to give the title compound.

Example 91

Donepezil Malonate

Malonic acid (1.18 g, dissolved in 35 ml of 2-propanol and 5 ml of water) is added slowly to a solution of Donepezil (3.79 g) in ethyl acetate (70 ml) with stirring at room temperature. The solid precipitated is filtered and dried at 55° C. under vacuum to give the title compound. Melting point: 165.7° C.

Example 92

Donepezil Acetylsalicylate 3.79 g of Donepezil is dissolved in 70 ml of ethyl acetate, and a solution of acetylsalicylic acid (1.80 g) in acetone (35 ml) is added slowly with stirring at room temperature. The solid precipitated is filtered. Melting point: 173-176° C.

Example 93

Donepezil Benzoate

Donepezil benzoate is prepared following the same method as described in Example 92.

$^1$H NMR ($D_2O$): δ 7.33-7.28 (m, 5H), 6.87 (s, 1H), 6.84 (s, 1H), 4.07 (s, 2H), 3.70 (s, 3H), 3.62 (s, 3H), 3.35-3.28 (m, 2H), 3.05-2.98 (m, 1H), 2.83-2.75 (m, 2H), 2.63 (d, 2H, J=16 Hz), 2.53 (s, 2H), 2.49 (s, 2H), 1.88-1.82 (m, 1H), 1.72-1.67 (m, 1H), 1.53-1.48 (m, 2H), 1.25-1.13 (m, 3H)

Example 94

Donepezil Aspartate

Donepezil aspartate is prepared following the same method as described in Example 92.

$^1$H NMR ($D_2O$): δ 7.30-7.28 (m, 5H), 6.68 (s, 1H), 6.66 (s, 1H), 4.08 (s, 2H), 3.66 (dd, 1H, J=4 Hz, J=16 Hz), 3.62 (s, 3H), 3.54 (s, 3H), 3.34-3.28 (m, 2H), 2.89-2.76 (m, 3H), 2.58 (dd, 1H, J=4 Hz, J=16 Hz), 2.47-2.33 (m, 3H), 1.82-1.79 (m, 1H), 1.70-1.66 (m, 1H), 1.57-1.51 (m, 2H), 1.21-1.09 (m, 3H)

Example 95

Donepezil Citrate

Donepezil citrate is prepared following the same method as described in Example 92.

$^1$H NMR (D$_2$O): δ 7.33-7.28 (m, 5H), 6.87 (s, 1H), 6.84 (s, 1H), 4.07 (s, 2H), 3.70 (s, 3H), 3.62 (s, 3H), 3.35-3.28 (m, 2H), 3.05-2.98 (m, 1H), 2.83-2.75 (m, 2H), 2.63 (d, 2H, J=16 Hz), 2.53 (s, 2H), 2.49 (s, 2H), 1.88-1.82 (m, 1H), 1.72-1.67 (m, 1H), 1.53-1.48 (m, 2H), 1.25-1.13 (m, 3H)

Example 96

Donepezil Ascorbate

Donepezil ascorbate is prepared following the same method as described in Example 92.

Example 97

Donepezil Formate

Donepezil formate is prepared following the same method as described in Example 92.

$^1$H NMR (D$_2$O): δ 8.21 (s, 1H), 7.30-7.28 (m, 5H), 6.71 (s, 2H), 4.07 (s, 2H), 3.64 (s, 3H), 3.56 (s, 3H), 3.35-3.28 (m, 2H), 2.93-2.86 (m, 1H), 2.82-2.75 (m, 2H), 2.38 (d, 2H, J=16 Hz), 1.84-1.80 (m, 1H), 1.70-1.66 (m, 1H), 1.55-1.45 (m, 2H), 1.24-1.08 (m, 3H)

Example 98

Donepezil Gallate

Donepezil gallate is prepared following the same method as described in Example 92.

$^1$H NMR (D$_2$O): δ 7.28-7.24 (m, 5H), 6.74 (s, 2H), 6.72 (s, 1H), 6.69 (s, 1H), 4.03 (s, 2H), 3.63 (s, 3H), 3.56 (s, 3H), 3.31-3.23 (m, 2H), 2.89-2.83 (m, 1H), 2.77-2.70 (m, 2H), 2.35 (d, 2H, J=16 Hz), 2.53 (s, 2H), 2.49 (s, 2H), 1.88-1.77 (m, 1H), 1.67-1.63 (m, 1H), 1.49-1.45 (m, 2H), 1.24-1.05 (m, 3H)

Example 99

Donepezil Hydrochloride

Donepezil hydrochloride is prepared following the same method as described in Example 92.

Example 100

Donepezil Acetate

Donepezil acetate is prepared following the same method as described in Example 92.

Example 101

Donepezil Lactate

Donepezil lactate is prepared following the same method as described in Example 92.

$^1$H NMR (D$_2$O): δ 7.30-7.28 (m, 5H), 6.78 (s, 1H), 6.77 (s, 1H), 4.07 (s, 2H), 3.91-3.85 (m, 1H), 3.66 (s, 3H), 3.59 (s, 3H), 3.31-3.23 (m, 2H), 2.97-2.91 (m, 1H), 2.84-2.74 (m, 2H), 2.43 (d, 2H, J=16 Hz), 1.84-1.78 (m, 1H), 1.70-1.66 (m, 1H), 1.58-1.46 (m, 2H), 1.23-1.13 (m, 3H), 1.09 (d, 3H, J=3.0)

Example 102

Donepezil Sorbate

Donepezil sorbate is prepared following the same method as described in Example 92.

$^1$H NMR (D$_2$O): δ 7.22 (s, 5H), 6.79 (s, 1H), 6.78 (s, 1H), 6.69-6.62 (m, 1H), 5.92-5.86 (m, 1H), 5.82-5.74 (m, 1H), 5.48 (d, 1H, J=16 Hz), 4.01 (s, 2H), 3.63 (s, 3H), 3.55 (s, 3H), 3.23-3.16 (m, 2H), 2.93 (d, 2H, J=16 Hz), 2.74-2.68 (m, 2H), 2.41 (d, 2H, J=16 Hz), 1.74 (d, 1H, J=14 Hz), 1.63 (d, 1H, J=14 Hz), 1.53-1.46 (m, 2H), 1.49 (d, 3H, J=4 Hz), 1.28-1.12 (m, 3H)

Example 103

Donepezil Glutaminate

Donepezil glutaminate is prepared following the same method as described in Example 92.

$^1$H NMR (D$_2$O): δ 7.28-7.23 (m, 5H), 6.67 (s, 2H), 4.03 (s, 2H), 3.59 (s, 3H), 3.52 (s, 3H), 3.48-3.45 (m, 2H), 3.29-3.22 (m, 2H), 2.88-2.68 (m, 3H), 2.34 (d, 2H, J=16 Hz), 2.09-2.06 (m, 2H), 1.85-1.73 (m, 3H), 1.66-1.62 (m, 1H), 1.50-1.39 (m, 2H), 1.10-1.03 (m, 3H)

Example 104

Preparation of an Orally Disintegrating Tablet of Donepezil Salicylate Formulation

| | |
|---|---|
| Donepezil Salicylate | 5% |
| Lactose | 15% |
| MCC | 25% |
| PVPP | 10% |
| Mannitol | 40% |
| Micropowder Silica Gel | 3% |
| Magnesium Stearate | 1% |
| Aspartame | 1% |

Method for its preparation comprises the following steps: weighing the above-mentioned ingredients; pulverizing the active ingredient, the filler, the disintegrant and the flavoring agent, sieving them with a 80-mesh screen, and mixing uniformly; adding the glidant and the lubricant, and mixing uniformly; determining the content of these powders; and tabletting to give the orally disintegrating tablet with a predetermined tablet weight.

The tablet has a disintegration time of 25 s in pure water, produces a sweet taste and a refreshing feeling, without a gritty feeling.

Example 105

Preparation of an Orally Disintegrating Tablet of Donepezil Nitrate Formulation

| | |
|---|---|
| Donepezil Nitrate | 5% |
| MCC | 30% |
| CCMs-Na | 7% |
| Mannitol | 50% |
| Micropowder Silica Gel | 5% |
| Talc Powder | 1% |
| Stevioside | 2% |

The method for preparation is the same as that of Example 26.

The tablet has a disintegration time of 49 s in pure water, produces a sweet taste and a refreshing feeling, without a gritty feeling.

Example 106

Preparation of an Orally Disintegrating Tablet of Donepezil Nitrate Formulation

| | |
|---|---|
| Donepezil Nitrate | 10% |
| Sugar Powder | 10% |
| MCC | 28% |
| L-HPC | 7% |
| PVPP | 5% |
| Mannitol | 35% |
| Micropowder Silica Gel | 3% |
| Magnesium Stearate | 1% |
| Xylitol | 1% |

The method for preparation is the same as that of Example 104.

The tablet has a disintegration time of 37 s in pure water, produces a sweet taste and a refreshing feeling, without a gritty feeling.

Example 107

Preparation of an Orally Disintegrating Tablet of Donepezil Mesylate Formulation

| | |
|---|---|
| Donepezil Mesylate | 5% |
| Lactose | 15% |
| MCC | 25% |
| CCNa | 6% |
| Mannitol | 46.5% |
| Micropowder Silica Gel | 2% |
| Magnesium Stearate | 0.5% |

The method for preparation is the same as that of Example 104.

The tablet has a disintegration time of 21 s in pure water.

Example 108

Preparation of an Orally Disintegrating Tablet of Donepezil Gallate Formulation

| | |
|---|---|
| Donepezil Gallate | 5% |
| Lactose | 15% |
| MCC | 25% |
| CCNa | 6% |
| Mannitol | 31% |
| Erythritol | 15% |
| Micropowder Silica Gel | 2% |
| Magnesium Stearate | 0.5% |
| Aspartame | 0.5% |

The method for preparation is the same as that of Example 104.

Orally disintegrating tablets of hydrochloride, nitrate, bisulfate, dihydric phosphate, succinate, maleate, fumarate, para-toluenesulphonate, tartrate, acetylsalicylate, benzoate, aspartate, citrate, ascorbate, nicotinate, and phthalate of Donepezil are prepared following the formulation and the method for preparing the orally disintegrating tablet disclosed in Example 104 (Method A), and a taste test is performed on these Orally disintegrating tablets.

Orally disintegrating tablets of hydrochloride, nitrate, bisulfate, dihydric phosphate, succinate, maleate, fumarate, para-toluenesulphonate, tartrate, acetylsalicylate, benzoate, aspartate, citrate, ascorbate, nicotinate, and phthalate of Donepezil are prepared following the formulation and the method for preparing the orally disintegrating tablet specified in Example 106 (Method B).

Example 109

Preparation of a Buccal Tablet of Donepezil Nitrate Formulation

| | |
|---|---|
| Donepezil Nitrate | 5.3% |
| Lactose | 29% |
| Mannitol | 40% |
| Erythritol | 23.15% |
| Menthol Crystal | 0.5% |
| Tartrazine | 0.05% |
| 4% PVP-50% Ethanol Solution | Proper amount |
| Polyethylene Glycol 4000 | 1% |

Method for its preparation comprises the following steps: pulverizing the active ingredient, the filler and the flavoring agent, sieving with a 80-mesh screen, and mixing uniformly; adding the binder portion-wisely to form a soft material, and granulating the soft material with a 25-mesh screen; drying the resulted particles at 60° C. for 1-2 hours, and sizing with a 30-mesh screen; adding the lubricant and the colorant, and mixing uniformly; determining the content of the active ingredient in the particles; and tabletting with predetermined tablet weight.

The tablet produces a sweet taste and refreshing feeling, without a gritty feeling.

Example 110

Preparation of an Effervescent Tablet of Donepezil Nitrate Formulation

| | |
|---|---|
| Donepezil Nitrate | 5.3% |
| Citric Acid | 15% |
| Sodium Bicarbonate | 9% |
| Cross-linked Carboxymethylcellulose Sodium | 6% |
| Lactose | 15% |
| Starch | 27.7% |
| Microcrystalline Cellulose | 20% |
| Orange Essence | 0.5% |
| 1% HPMC Solution | Proper amount |
| Magnesium Stearate | 0.5% |

Method for its preparation comprises the following steps: pulverizing the active ingredient, the filler, the disintegrant and the flavoring agent, sieving with a 80-mesh screen, and mixing uniformly; adding the binder portion-wisely to form a soft material, and granulating the soft material with a 25-mesh screen; drying the resulted particles at 60° C. for 1-2 hours, and sizing with a 30-mesh screen; adding the lubricant, and mixing uniformly; determining the content of the active ingredient in the particles; and tabletting with predetermined tablet weight.

The tablet completely disintegrates within 2 minutes in pure water and produces a sweet taste and refreshing feeling.

Example 111

Preparation of Granules of Donepezil Nitrate Formulation

| | |
|---|---|
| Donepezil Nitrate | 0.2% |
| Starch | 34% |
| Microcrystalline Cellulose | 27% |
| Lactose | 38.7% |
| Stevioside | 0.05% |
| Sunset Yellow | 0.05% |
| 80% Ethanol | Proper amount |

Method for its preparation comprises the following steps: pulverizing the active ingredient, the filler, and the flavoring agent, sieving with a 80-mesh screen, and mixing uniformly; dissolving the colorant in the binder, adding the binder portion-wisely to form a soft material, and granulating the soft material with a 14-mesh screen; and drying the resulted particles at 60° C. for 1-2 hours, and sizing with a 16-mesh screen to give the granules.

The granule is completely dissolved within 5 minutes in hot water and produces a sweet taste and refreshing feeling.

Example 112

Preparation of oral liquids of Donepezil nitrate

| | |
|---|---|
| Donepezil Nitrate | 0.1% |
| Poloxamer | 0.5% |
| Aspartame | 0.2% |
| Methyl Hydroxybenzoate | 0.05% |
| Distilled Water | 99.15% |

Method for its preparation comprises the following steps: dissolving poloxamer in distilled water; adding Donepezil nitrate, and stirring to completely dissolve; adding methyl hydroxybenzoate, mixing uniformly, and filtering; and adding distilled water to 1000 ml, and sterilizing to give the oral liquid.

Example 113

Preparation of a Chewable Tablet of Donepezil Nitrate Formulation

| | |
|---|---|
| Donepezil Nitrate | 5.3% |
| Lactose | 40% |
| Sorbitol | 22% |
| Mannitol | 30% |
| Menthol Crystal | 0.1% |
| Orange Essence | 0.1% |
| Carotene | 0.5% |
| 1% HPMC Solution | Proper amount |
| Magnesium Stearate | 1% |

Method for its preparation comprises the following steps: pulverizing the active ingredient, the filler, and the flavoring agent, sieving with a 80-mesh screen, and mixing uniformly; adding the binder portion-wisely to form a soft material, and granulating the soft material with a 25-mesh screen; drying the resulted particles at 60° C. for 1-2 hours, and sizing with a 30-mesh screen; adding the lubricant and the colorant, and mixing uniformly; determining the content of the active ingredient in the particles; and tabletting to give the chewable tablet with predetermined tablet weight.

The tablet produces a fruit sweet taste, without a gritty feeling

Example 114

Preparation of a Lyophilized Rapid Dissolving Tablet of Donepezil Nitrate Formulation

| | |
|---|---|
| Donepezil Nitrate | 10.6% |
| Mannitol | 49.4% |
| Glucose | 30% |
| Gelatin | 2.5% |
| Hydroxyethyl Cellulose | 7.5% |
| Water | Proper amount |

Method for its preparation comprises the following steps: pulverizing the active ingredient and the filler, sieving with a 80-mesh screen, and suspending the active ingredient in a solution of hydroxyethyl cellulose; dissolving the other excipients to form a solution; mixing the two solutions, and placing the resulted solution in a mold to freeze at low temperature; and completely drying the mixture at vacuum in a lyophilizer, and sealing to obtain the lyophilized rapid dissolving tablet.

The tablet is rapidly dissolved within 5 seconds in oral cavity and produces a sweet taste.

Example 114

Preparation of a Tablet of Donepezil Nitrate Formulation

| | |
|---|---|
| Donepezil Nitrate | 5% |
| Lactose | 16% |
| MCC | 25% |
| CCNa | 6% |
| Mannitol | 31% |
| Erythritol | 15% |
| Micropowder Silica Gel | 1.5% |
| Aaspartame | 0.5% |

Method for its preparation comprises the following steps: weighing the above-mentioned ingredients; pulverizing the active ingredient, the filler, the disintegrant and the flavoring agent, sieving with a 80-mesh screen, and mixing uniformly; adding the glidant and the lubricant, and mixing uniformly; determining the content of the active ingredient in the powders; and tabletting to give the tablet with predetermined tablet weight.

Example 115

Preparation of a Co-Crystal Φ-1 of Donepezil Hydrochloride and Maleic Acid 1 g (2.5 mmol) of Donepezil hydrochloride is added into a 250 ml flask, followed by adding 20 ml of ethanol. The mixture is stirred at 65° C. in a water-bath until the solid is almost dissolved to render a clear solution. 1 ml of water is added to completely dissolve the solid. 5 mmol of maleic acid is added, and the mixture is stirred at 65° C. for additional 0.5 hour in the water-bath, and at room temperature for 20 hours. No solid is precipitated. To the mixture are added 20 ml of ethyl acetate and ml of petroleum ether. Still, no solid is precipitated. The solvents are rotary-evaporated, and 10 ml of ethanol is added. The mixture is heated at 70° C. to dissolve the solid, and further stirred at room temperature. The solid is precipitated is filtered under suction, and the cake is washed to give a white solid, which is dried under vacuum.

Melting point Measurement: the sample begins to turn grey at 167° C., turns brown at 196° C., completely turns black and produces air bubbles at 203° C.

The melting point is measured three times to give the following results: 212.6-212.7° C., 213.3-212.2° C., 211.1-211.7° C. The melting point measured in the inlet tube is 208.1° C.

Example 116

Preparation of a Co-Crystal Φ-2 of Donepezil Hydrochloride and Fumaric Acid 1 g (2.5 mmol) of Donepezil hydrochloride is added into a 250 ml flask, followed by adding 20 ml of ethanol. The mixture is stirred at 60° C. in a water-bath until the solid is completely dissolved 2.5 mmol of fumaric acid is added, and the mixture is stirred at 65° C. for additional 0.5 hour in the water-bath, and then stirred at room temperature for 20 hours. The solid precipitated is filtered under suction and the cake is washed to give a white solid, which is dried under vacuum.

Melting point Measurement: the sample begins to turn yellow at 168° C., turns black at the top and gradually decomposes at 185° C.

The melting point is measured three times to give the following results: 211.8-214.8° C., 213.8-217.1° C., and 217.0-217.1° C. The melting point measured in the inlet tube is 204.3° C.

Example 117

Preparation of a Co-Crystal Φ-3 of Donepezil Hydrochloride and Fumaric Acid 1 g (2.5 mmol) of Donepezil hydrochloride is added into a 250 ml flask, followed by adding 20 ml of ethanol. The mixture is stirred at 65° C. in a water-bath until the solid is almost dissolved to render a clear solution. 1 ml of water is added to completely dissolve the solid. 5 mmol of fumaric acid is added, and the mixture is stirred at 65° C. for additional 0.5 hour in the water-bath, and then stirred at room temperature for 20 hours. No solid is precipitated. To the mixture are added 20 ml of ethyl acetate and 20 ml of petroleum ether to precipitate a solid. The mixture is stirred overnight at room temperature, and filtered under suction. The cake is washed to give a white solid.

Melting point Measurement: the sample begins to turn yellow and slightly melts at 159° C., melts at the top at 185° C., begins to gasify and slightly expands at 195° C.

The melting point is measured three times to give the following results: 211.3° C., 211.9° C., and 208.6° C. The melting point measured in the inlet tube is 199.1° C.

Example 118

Preparation of a Co-Crystal Φ-4 of Donepezil Hydrochloride and Citric Acid 1 g (2.5 mmol) of Donepezil hydrochloride is added into a 250 ml flask, followed by adding 5 ml of ethanol and 1 ml of water. The mixture is stirred at 70° C. in a water-bath until the solid is completely dissolved. 5 mmol of citric acid is added, and the mixture is stirred at 70° C. for additional 0.5 hour in the water-bath, and then stirred at room temperature for 20 hours. No solid is precipitated. Ethyl ether is added, and the mixture is stirred overnight at room temperature, and filtered under suction. The cake is washed to give a white solid.

Melting point Measurement: the sample begins to turn yellow at 135° C., begins to turn black at 208° C., turns black and slightly melts at 210° C., and produces bubbles at 212° C.

The melting point is measured three times to give the following results: 219.4° C., 216.3° C., and 216.1° C., and the average is 217.3° C.

Example 119

Preparation of a Co-Crystal Φ-5 of Donepezil Hydrochloride and Salicylic Acid 1 g (2.5 mmol) of Donepezil hydrochloride is added into a 250 ml flask, followed by adding 5 ml of ethanol and 1 ml of water. The mixture is stirred at 70° C. in a water-bath until the solid is completely dissolved. 5 mmol of salicylic acid is added, and the mixture is stirred at 70° C. for additional 0.5 hour in the water-bath, and then stirred at room temperature for 20 hours. No solid is precipitated. Ethyl ether is added, and the mixture is stirred overnight at room temperature, and filtered under suction. The cake is washed to give a white solid.

Melting point Measurement: at 167° C., the sample begins to turn grey; at 180° C., the sample turns silver grey and the top turns yellow; at 193° C., the silver grey part gasify to become transparent and the yellow part at the top expands and replaces the original silver grey part; at 200° C., the sample turns black at the top and produces bubbles; at 202° C., the sample turns grey black; and at 206° C., the sample turns black and most of the sample has decomposed.

The melting point is measured three times to give the following results: 204.5° C., 208.1° C., and 206.1° C., and the average is 206.2° C.

Example 120

Preparation of a Co-Crystal Φ-6 of Donepezil Hydrochloride and Tartaric Acid 1 g (2.5 mmol) of Donepezil hydrochloride is added into a 250 ml flask, followed by adding 5 ml of ethanol and 1 ml of water. The mixture is stirred at 70° C. in a water-bath until the solid is completely dissolved. 5 mmol of tartaric acid is added, and the mixture is stirred at 70° C. for additional 0.5 hour in the water-bath, and then stirred at room temperature for 20 hours. No solid is precipitated. Ethyl ether is added, and the mixture is stirred overnight at room temperature, and filtered under suction. The cake is washed to give a white solid.

Melting point Measurement: the sample begins to turn yellow at 180° C., turns brown and slightly expands at 198° C., turns black at the top at 206° C., begins to expand and turns burned black at 210° C., and begins to produce bubbles at 212° C.

The melting point is measured three times to give the following results: 215.2° C., 215.5° C., and 214.9° C., and the average is 215.2° C.

Example 121

Preparation of a Co-Crystal Φ-7 of Donepezil Hydrochloride and Succinic Acid 1 g (2.5 mmol) of Donepezil hydrochloride is added into a 250 ml flask, followed by adding 5 ml of ethanol and 1 ml of water. The mixture is stirred at 70° C. in a water-bath until the solid is completely dissolved. 5 mmol of succinic acid is added, and the mixture is stirred at 70° C. for additional 0.5 hour in the water-bath, and then stirred at room temperature for 20 hours. No solid is precipitated. Ethyl ether is added, and the mixture is stirred overnight at room temperature, and filtered under suction. The cake is washed to give a white solid.

Melting point Measurement: the sample begins to turn yellow at 173° C., begins to produces air bubbles at 215° C., and begins to turn black at the top, produces bubbles, and decomposes to a brownish-black liquid at 219° C.

The melting point is measured three times to give the following results: 228.2° C., 229.0° C., and 225.7° C., and the average is 227.6° C.

Example 122

Melting Point Measurement of Donepezil Hydrochloride

The sample turns black at the top at 219° C., and completely turns black and produces bubbles at 222° C.

BRIEF DESCRIPTION OF THE DRAWINGS

FIGS. 1-A-1 to 1-A-4 respectively show X-ray powder diffraction pattern, infrared absorption spectrum, thermogravimetric and differential thermal analysis spectrum and nuclear magnetic resonance spectrum of the polymorph (I-A) of Donepezil mesylate (I).

FIGS. 2-A-1 to 2-A-4 respectively show X-ray powder diffraction pattern, infrared absorption spectrum, thermogravimetric and differential thermal analysis spectrum and nuclear magnetic resonance spectrum of the polymorph (II-A) of Donepezil para-toluenesulfonate (II).

FIGS. 3-A-1 to 3-A-4 respectively show X-ray powder diffraction pattern, infrared absorption spectrum, thermogravimetric and differential thermal analysis spectrum and nuclear magnetic resonance spectrum of the polymorph (III-A) of Donepezil succinate (III).

FIGS. 4-A-1 to 4-A-4 respectively show X-ray powder diffraction pattern, infrared absorption spectrum, thermogravimetric and differential thermal analysis spectrum and nuclear magnetic resonance spectrum of the polymorph (IV-A) of Donepezil tartrate (IV).

FIGS. 5-A-1 to 5-A-4 respectively show X-ray powder diffraction pattern, infrared absorption spectrum, thermogravimetric and differential thermal analysis spectrum and nuclear magnetic resonance spectrum of the polymorph (V-A) of Donepezil sulphate (V).

FIGS. 5-B-1 to 5-B-4 respectively show X-ray powder diffraction pattern, infrared absorption spectrum, thermogravimetric and differential thermal analysis spectrum and nuclear magnetic resonance spectrum of the polymorph (V-B) of Donepezil sulphate (V).

FIGS. 6-A-1 to 6-A-4 respectively show X-ray powder diffraction pattern, infrared absorption spectrum, thermogravimetric and differential thermal analysis spectrum and nuclear magnetic resonance spectrum of the polymorph (VI-A) of Donepezil nitrate (VI).

FIGS. 7-A-1 to 7-A-4 respectively show X-ray powder diffraction pattern, infrared absorption spectrum, thermogravimetric and differential thermal analysis spectrum and nuclear magnetic resonance spectrum of the polymorph (VII-A) of Donepezil phosphate (VII).

FIGS. 8-A-1 to 8-A-4 respectively show X-ray powder diffraction pattern, infrared absorption spectrum, thermogravimetric and differential thermal analysis spectrum and nuclear magnetic resonance spectrum of the polymorph (VIII-A) of Donepezil salicylate (VIII).

FIGS. 9-A-1 to 9-A-4 respectively show X-ray powder diffraction pattern, infrared absorption spectrum, thermogravimetric and differential thermal analysis spectrum and nuclear magnetic resonance spectrum of the polymorph (IX-A) of Donepezil fumarate (IX).

FIGS. 10-A-1 to 10-A-4 respectively show X-ray powder diffraction pattern, infrared absorption spectrum, thermogravimetric and differential thermal analysis spectrum and nuclear magnetic resonance spectrum of the polymorph (X-A) of Donepezil maleate (X).

FIGS. 10-B-1 to 10-B-4 respectively show X-ray powder diffraction pattern, infrared absorption spectrum, thermogravimetric and differential thermal analysis spectrum and nuclear magnetic resonance spectrum of the polymorph (X-B) of Donepezil maleate (X).

FIG. 14-1 shows X-ray powder diffraction pattern of the co-crystal Φ-1 of Donepezil hydrochloride and maleic acid.

FIG. 14-2 shows nuclear magnetic resonance spectrum of the co-crystal Φ-1 of Donepezil hydrochloride and maleic acid.

FIG. 15-1 shows X-ray powder diffraction pattern of the co-crystal Φ-2 of Donepezil hydrochloride and fumaric acid.

FIG. 15-2 shows nuclear magnetic resonance spectrum of the co-crystal Φ-2 of Donepezil hydrochloride and fumaric acid.

FIG. 16-1 shows X-ray powder diffraction pattern of the co-crystal Φ-3 of Donepezil hydrochloride and fumaric acid.

FIG. 16-2 shows nuclear magnetic resonance spectrum of the co-crystal Φ-3 of Donepezil hydrochloride and fumaric acid.

FIG. 17-1 shows X-ray powder diffraction pattern of the co-crystal Φ-4 of Donepezil hydrochloride and citric acid.

FIG. 17-2 shows nuclear magnetic resonance spectrum of the co-crystal Φ-4 of Donepezil hydrochloride and citric acid.

FIG. 18-1 shows X-ray powder diffraction pattern of the co-crystal Φ-5 of Donepezil hydrochloride and salicylic acid.

FIG. 18-2 shows nuclear magnetic resonance spectrum of the co-crystal Φ-5 of Donepezil hydrochloride and salicylic acid.

FIG. 19-1 shows X-ray powder diffraction pattern of the co-crystal Φ-6 of Donepezil hydrochloride and tartaric acid.

FIG. 19-2 shows nuclear magnetic resonance spectrum of the co-crystal Φ-6 of Donepezil hydrochloride and tartaric acid.

FIG. 20-1 shows X-ray powder diffraction pattern of the co-crystal Φ-7 of Donepezil hydrochloride and succinic acid.

FIG. 20-2 shows nuclear magnetic resonance spectrum of the co-crystal Φ-7 of Donepezil hydrochloride and succinic acid.

Figure 11:
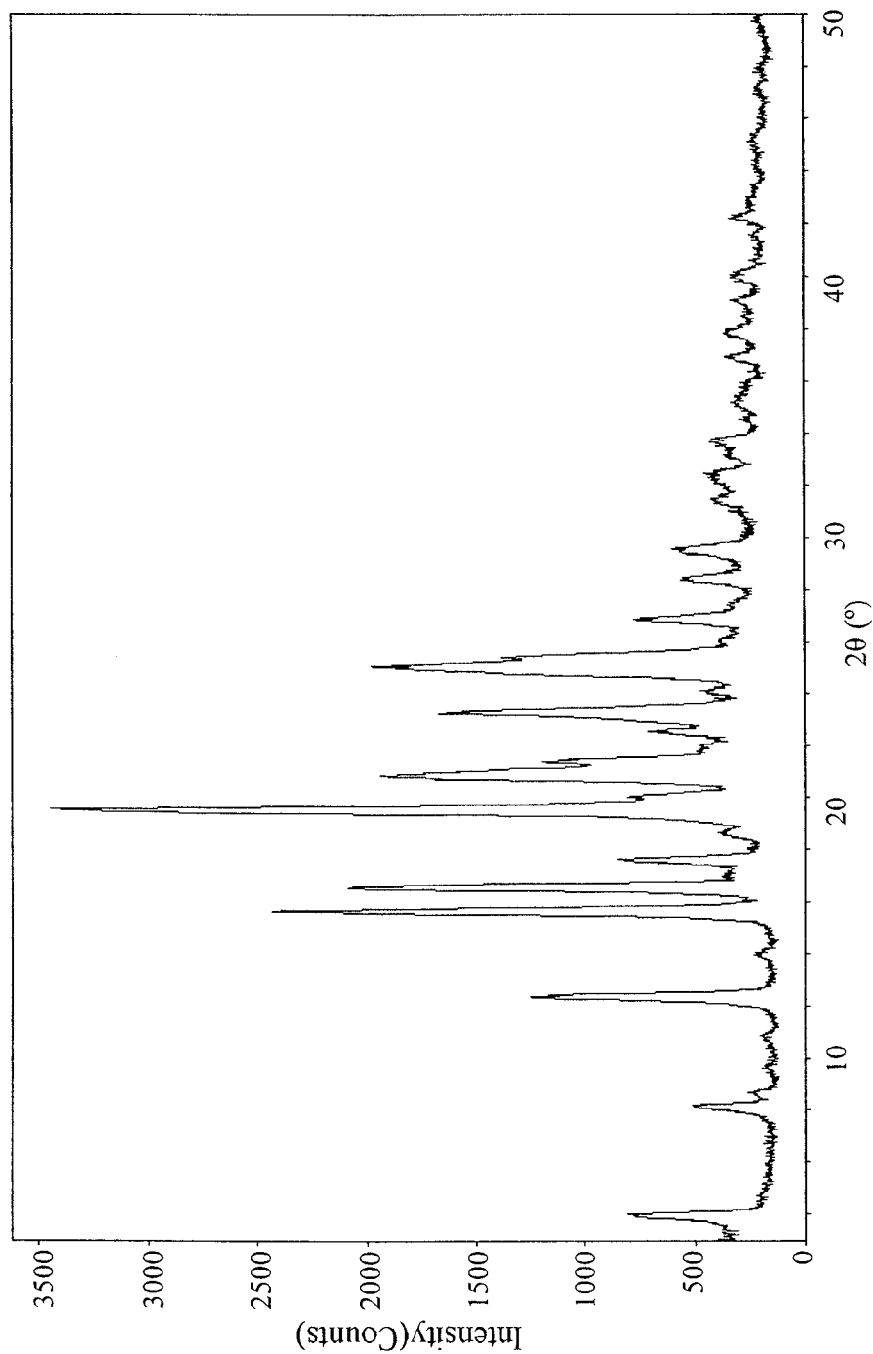
FIG. 11 shows X-ray powder diffraction pattern of a polymorph of Donepezil malate.
Figure 12:
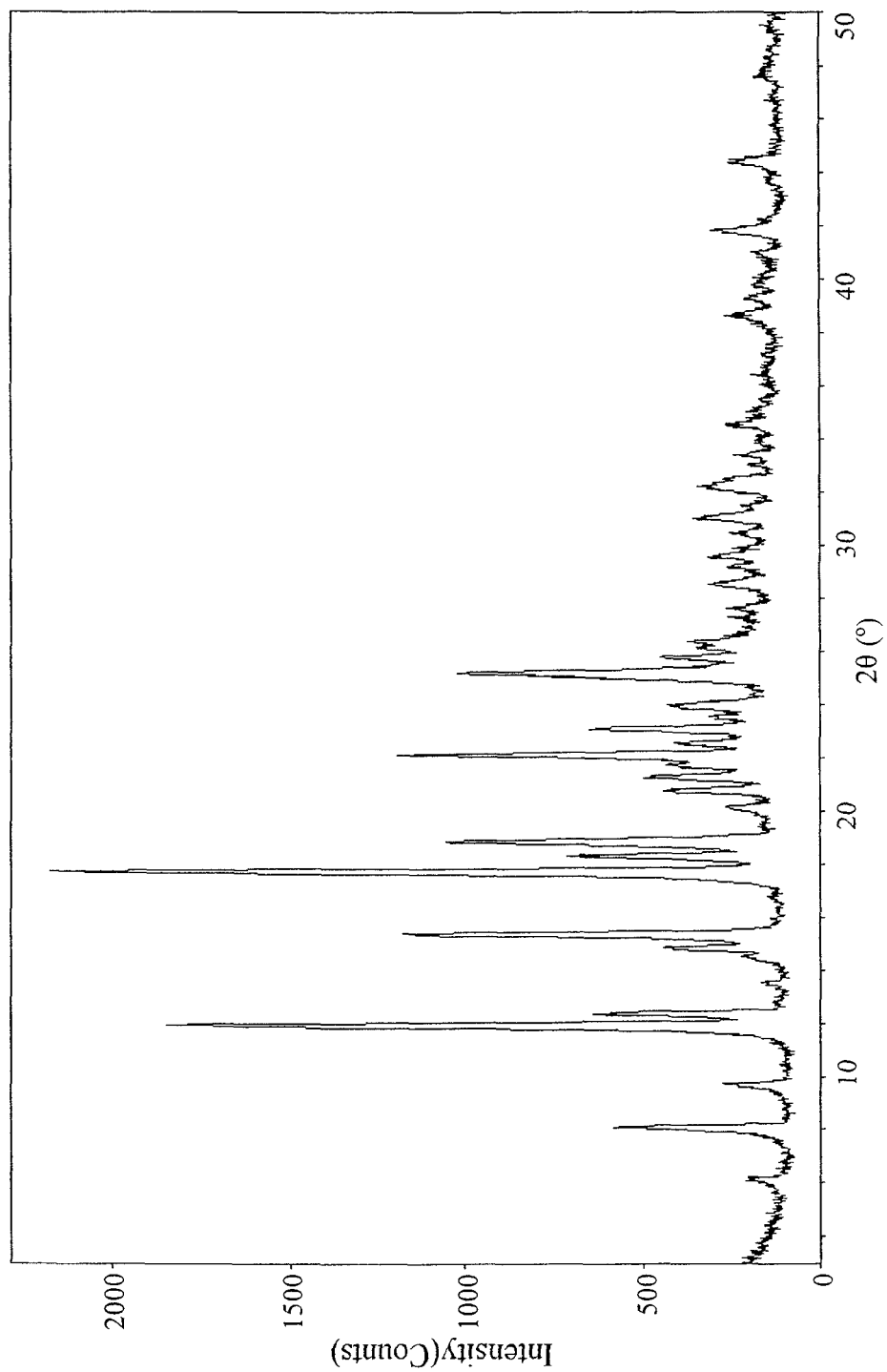
FIG. 12 shows X-ray powder diffraction pattern of a polymorph of Donepezil benzenesulphonate.
Figure 13:
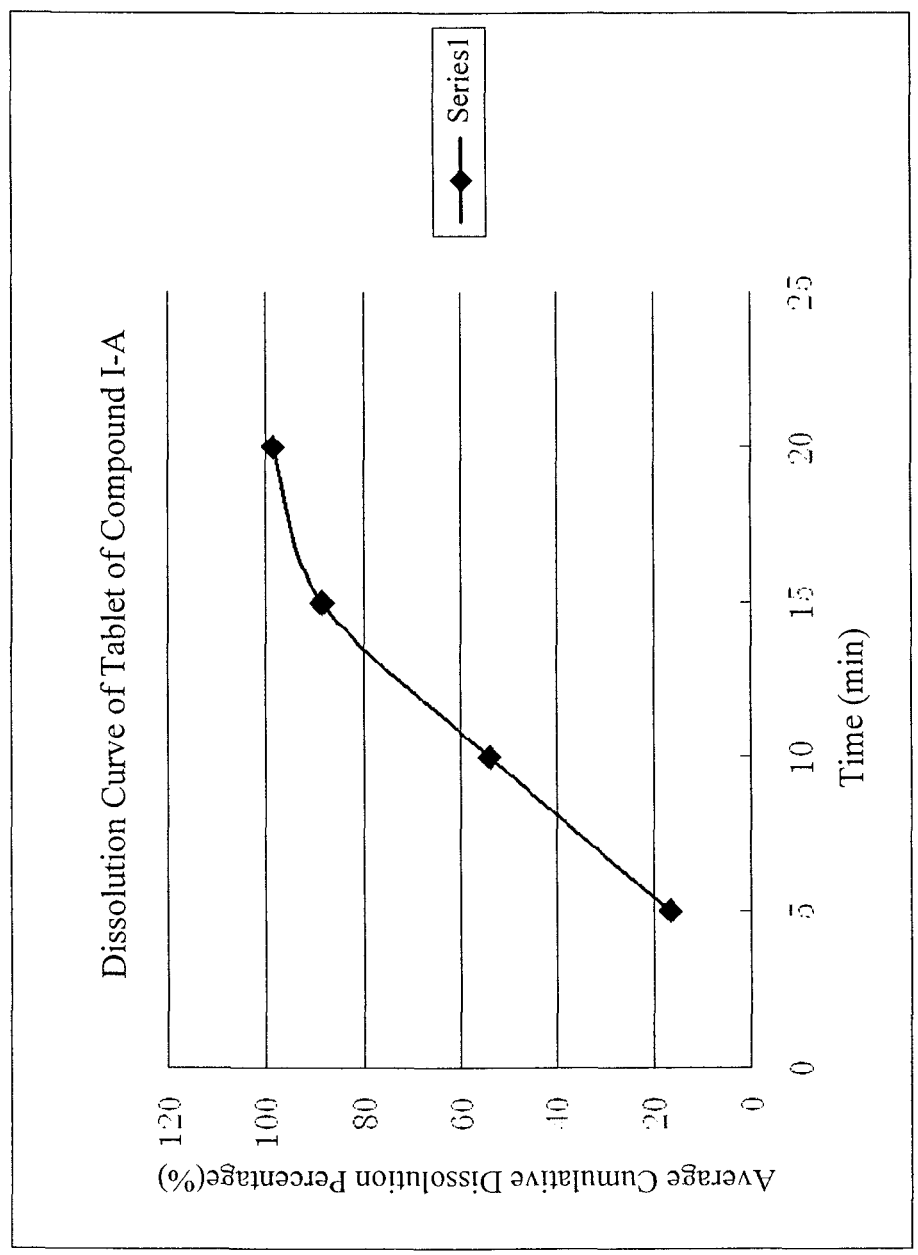
FIG. 13 shows results of dissolution test of a tablet comprising the polymorph (I-A) of Donepezil mesylate.
Figures 1, 14:
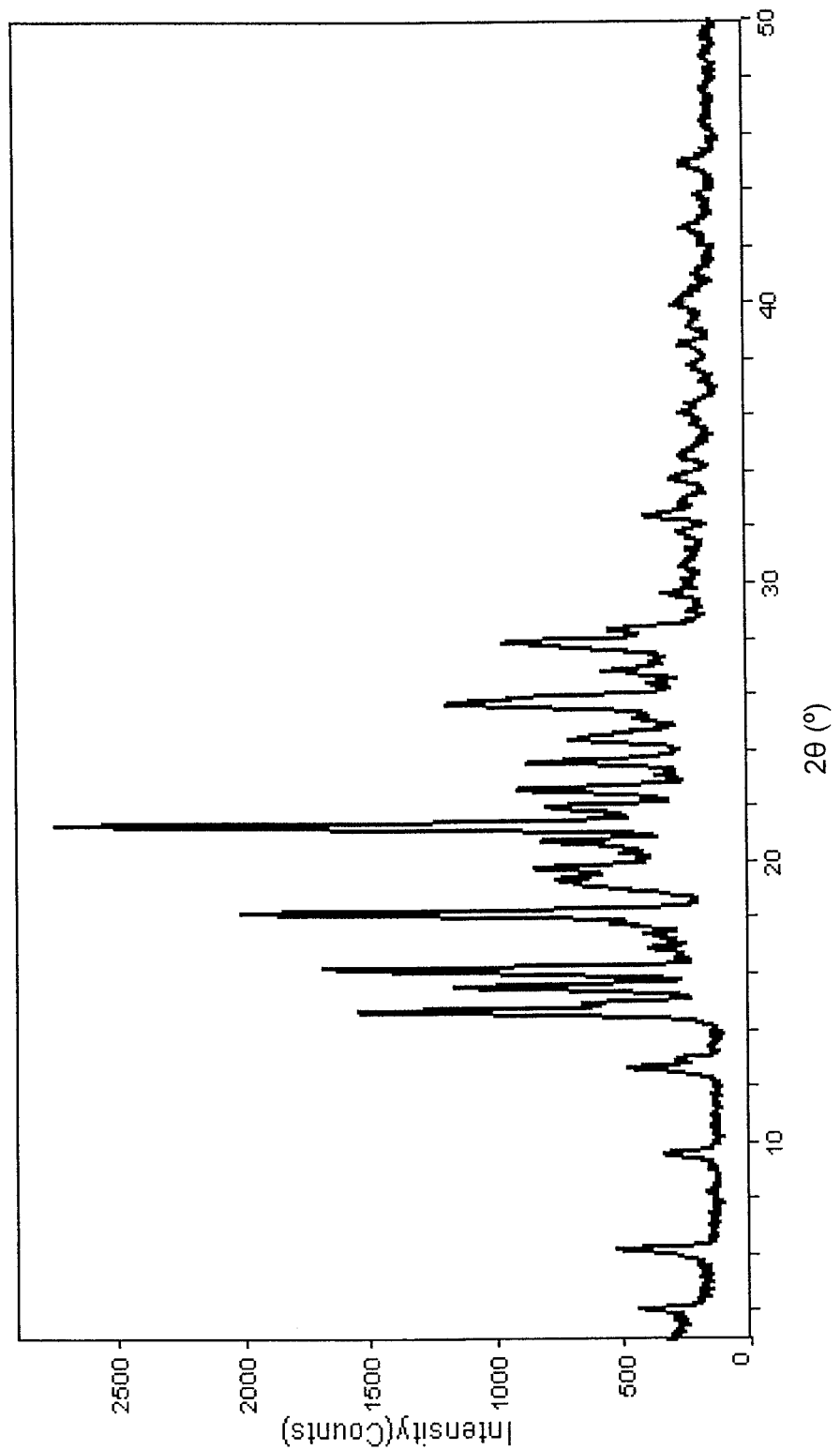
Figures 2, 14:
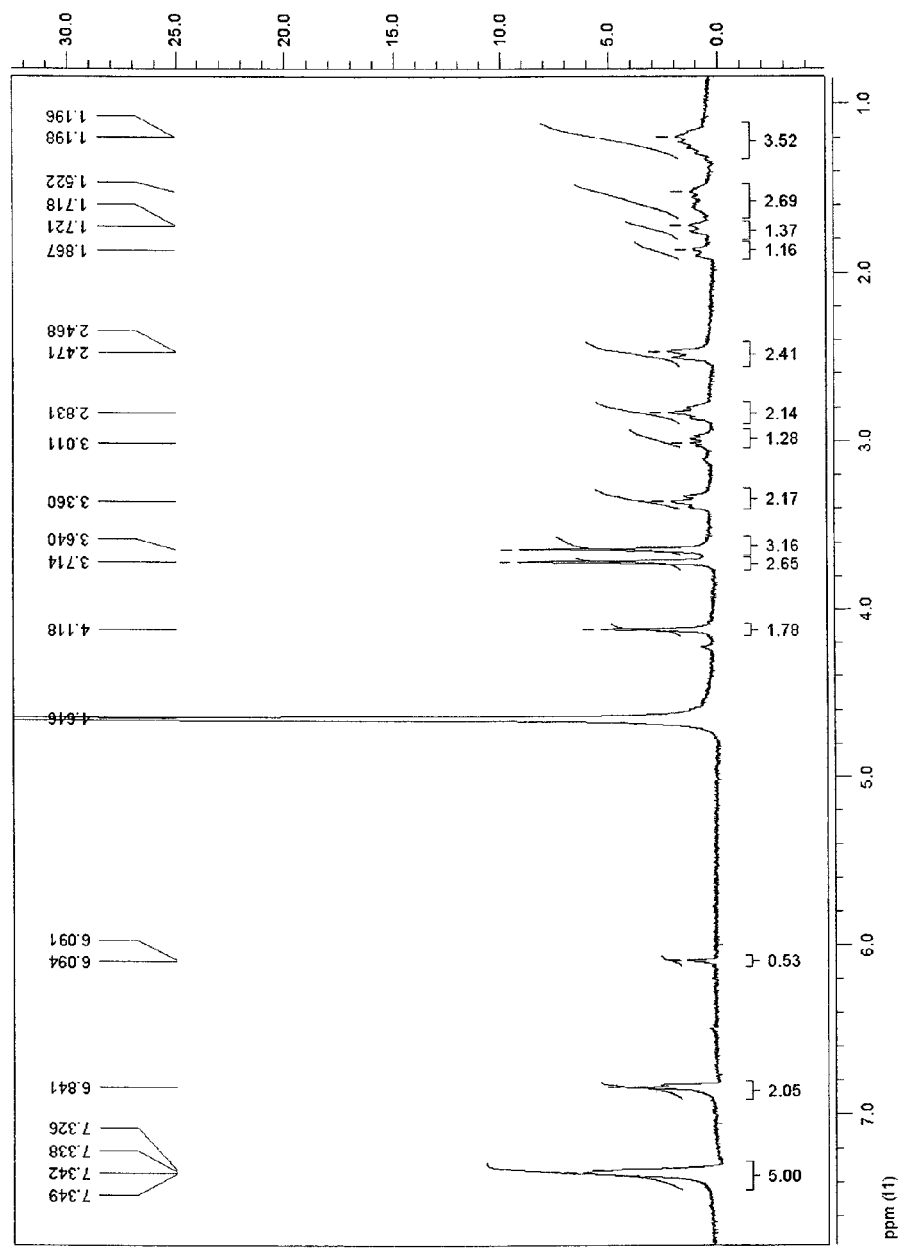
Figures 1, 15:
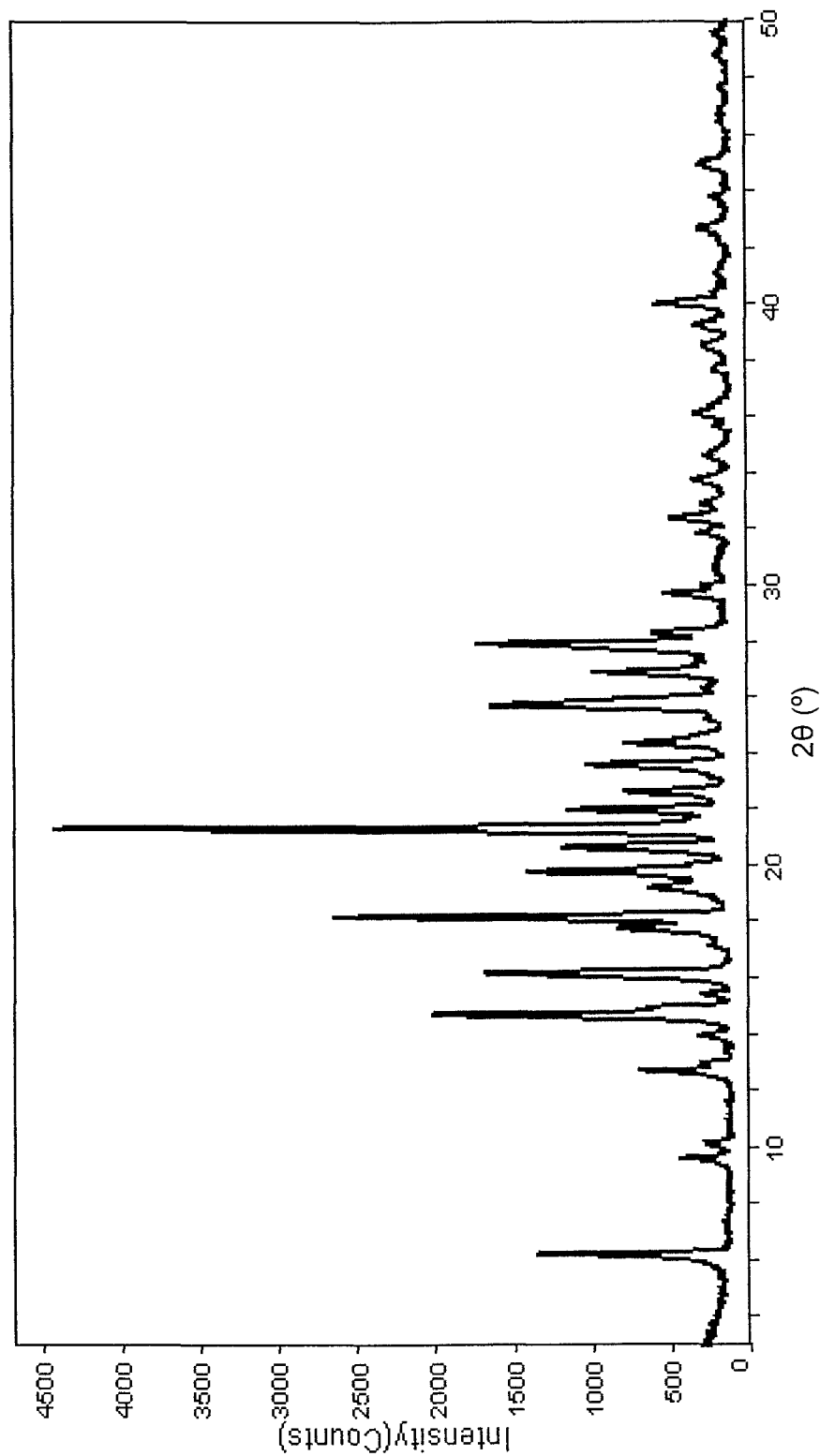
Figures 2, 15:
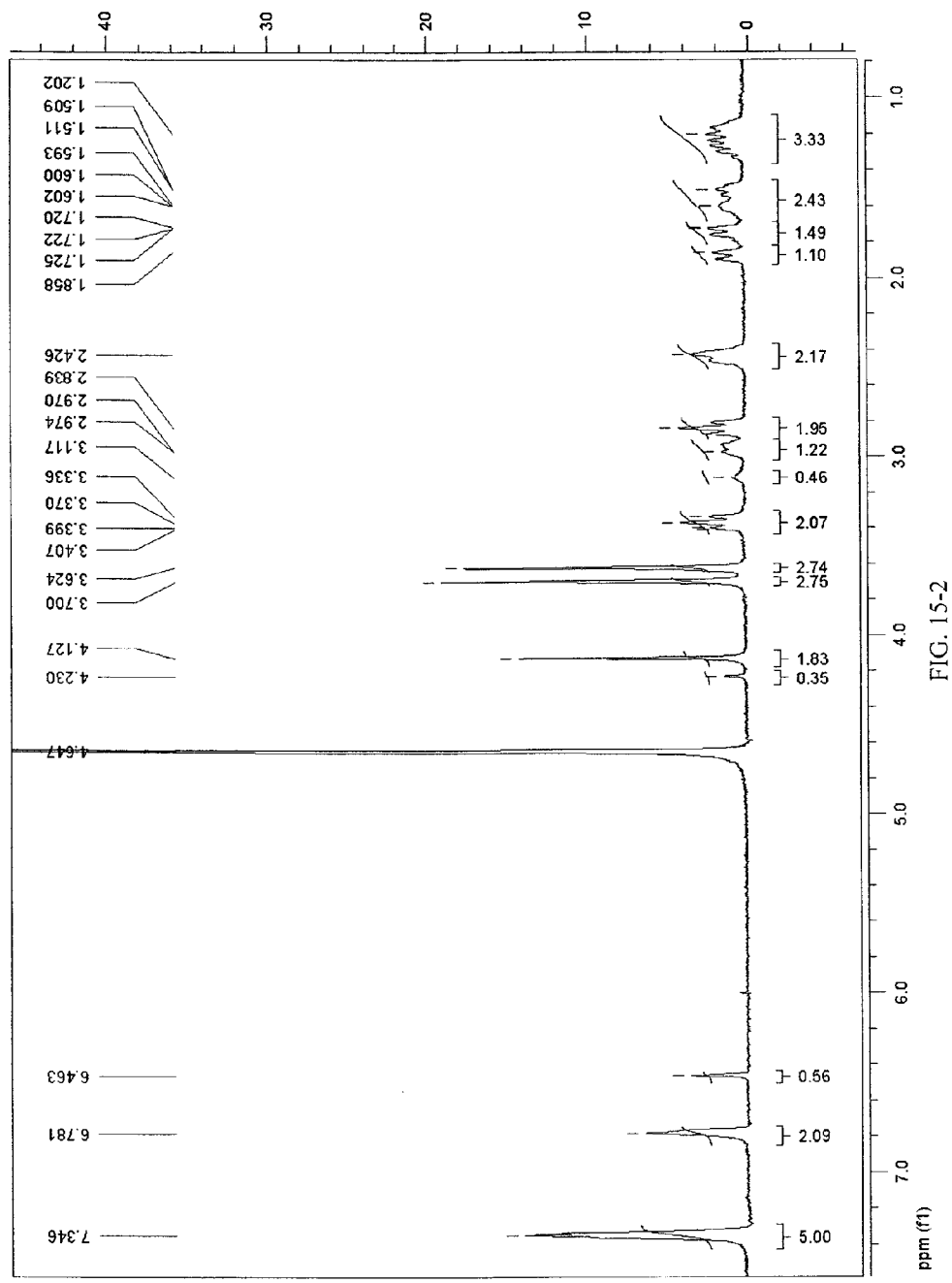
Figures 1, 16:
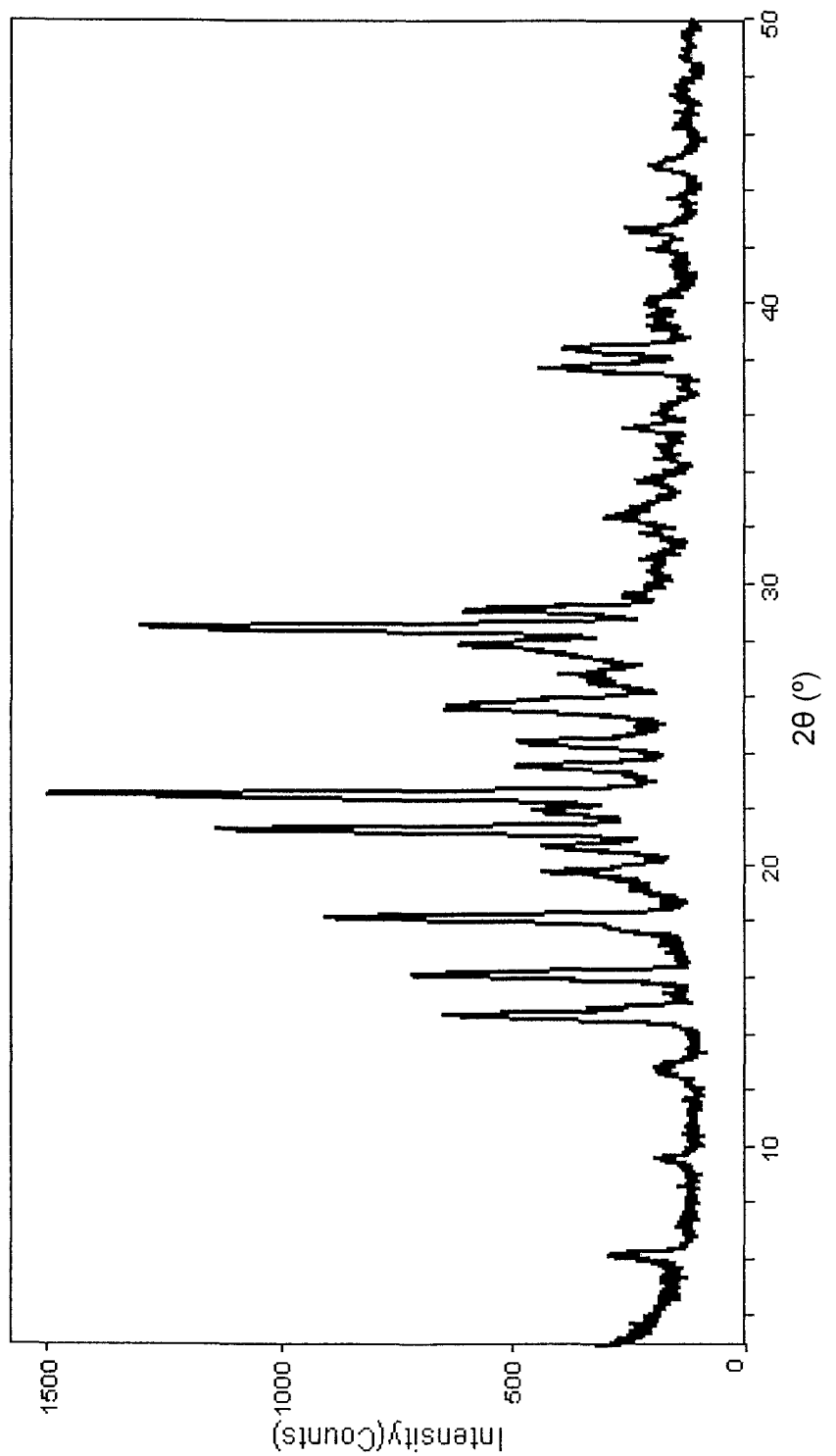
Figures 2, 16:
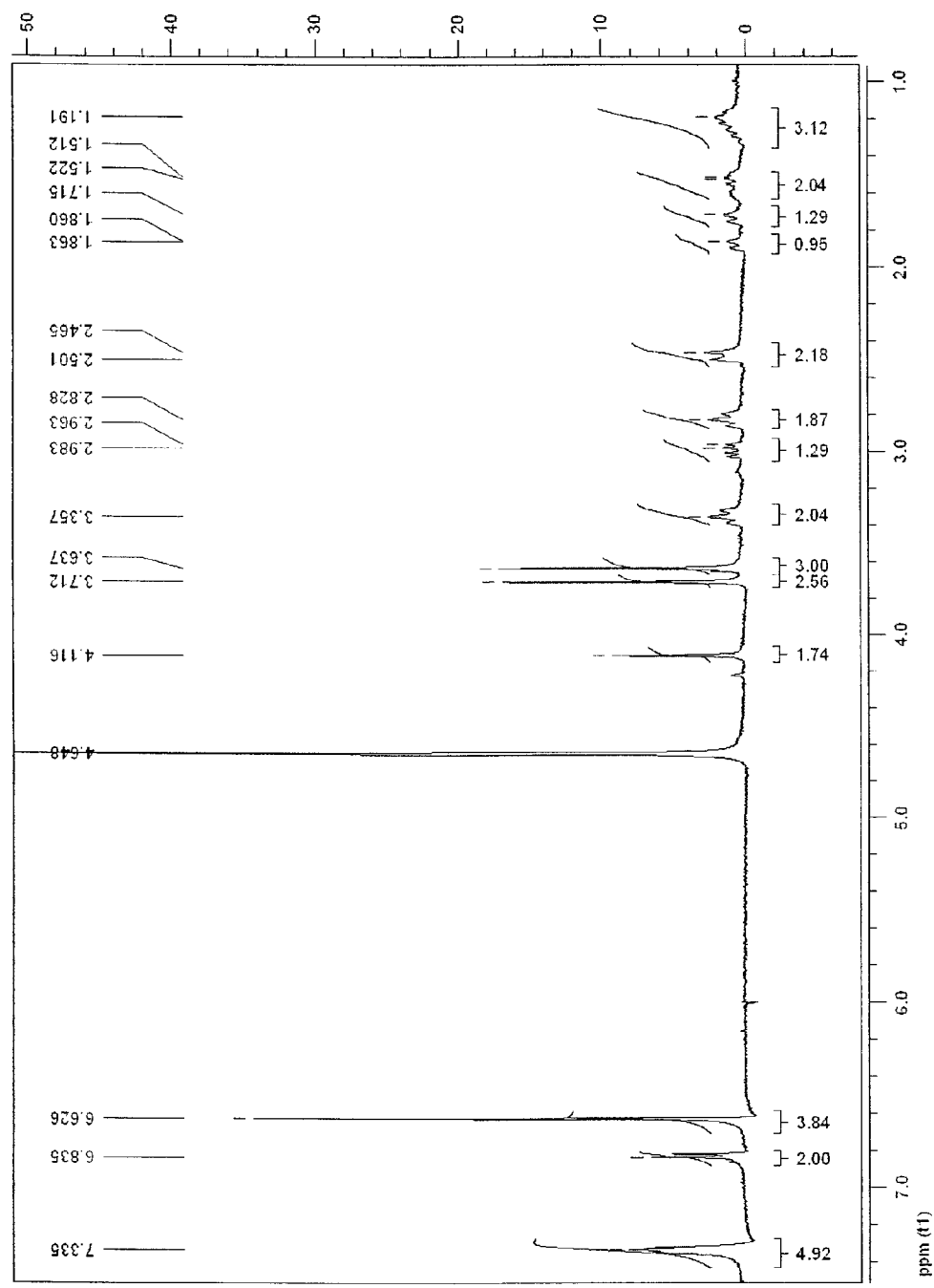
Figures 1, 17:
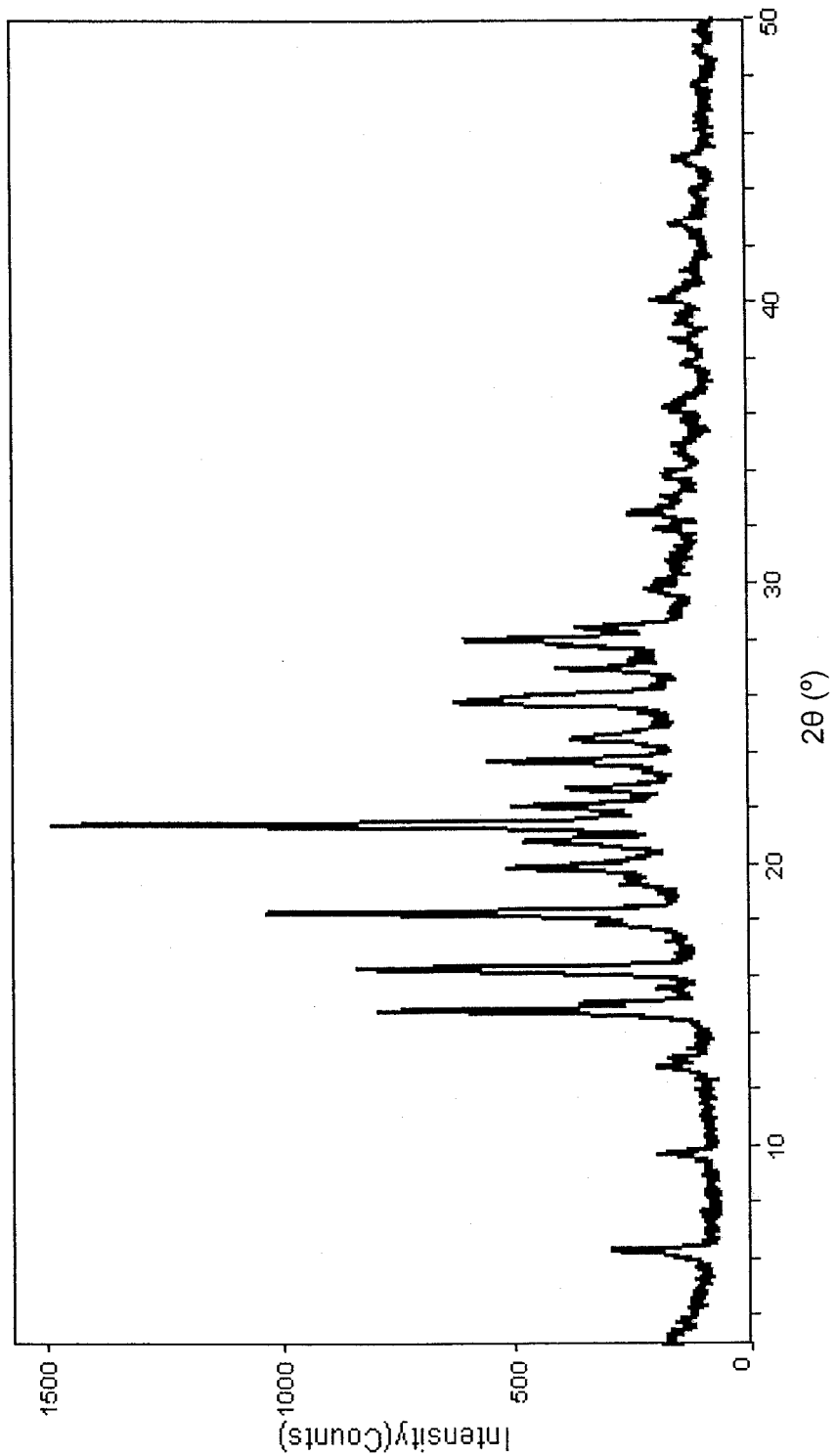
Figures 2, 17:
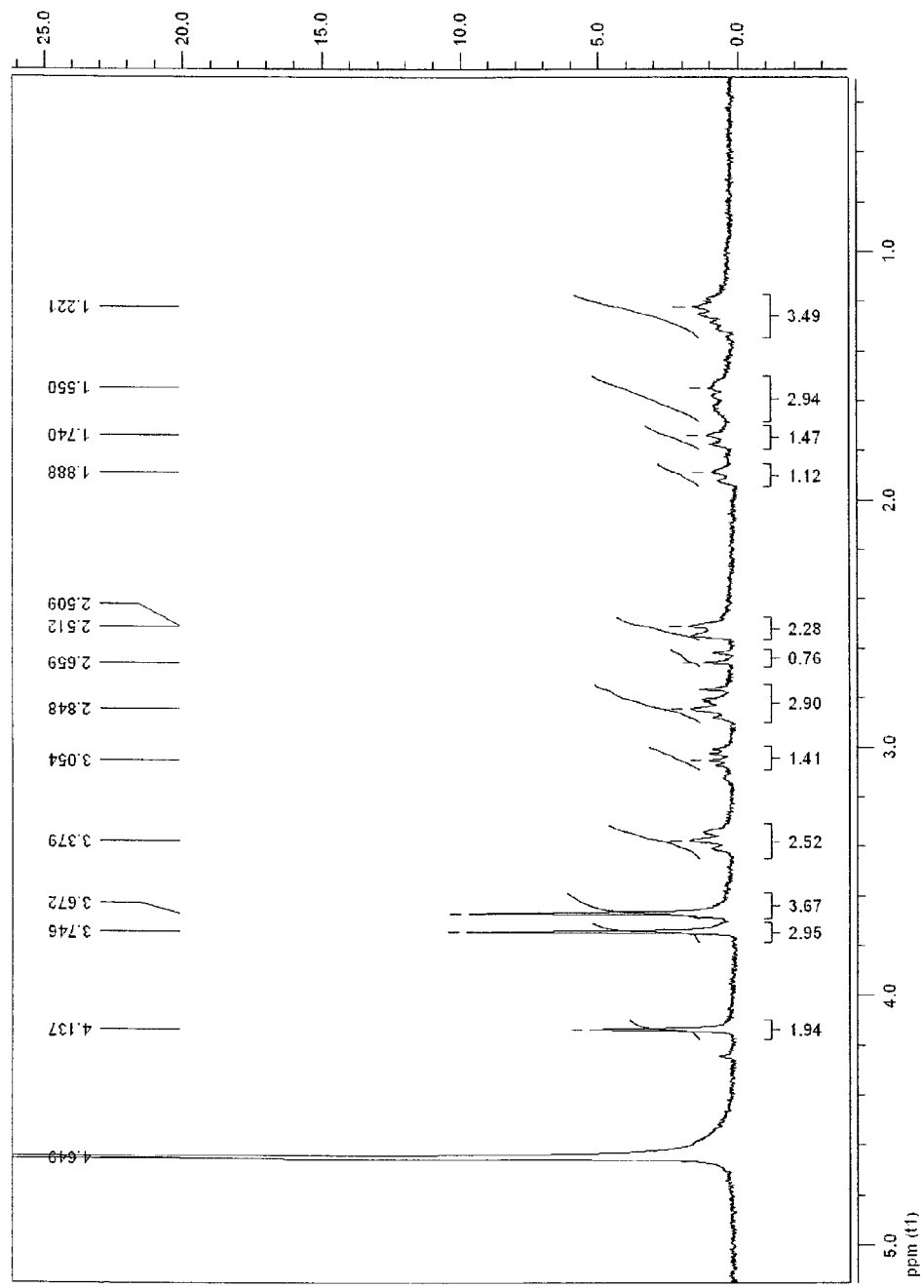
Figures 1, 18:
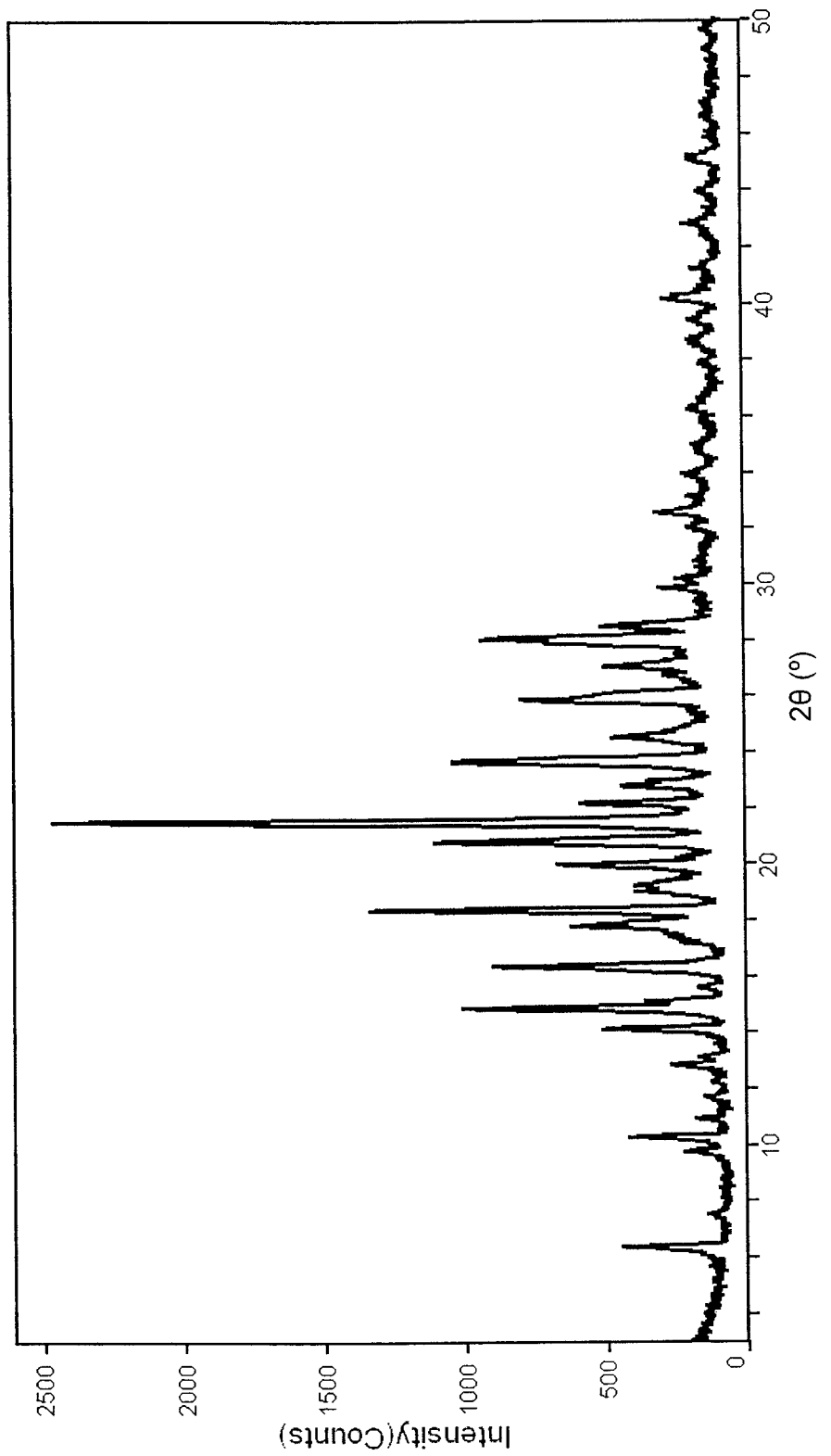
Figures 2, 18:
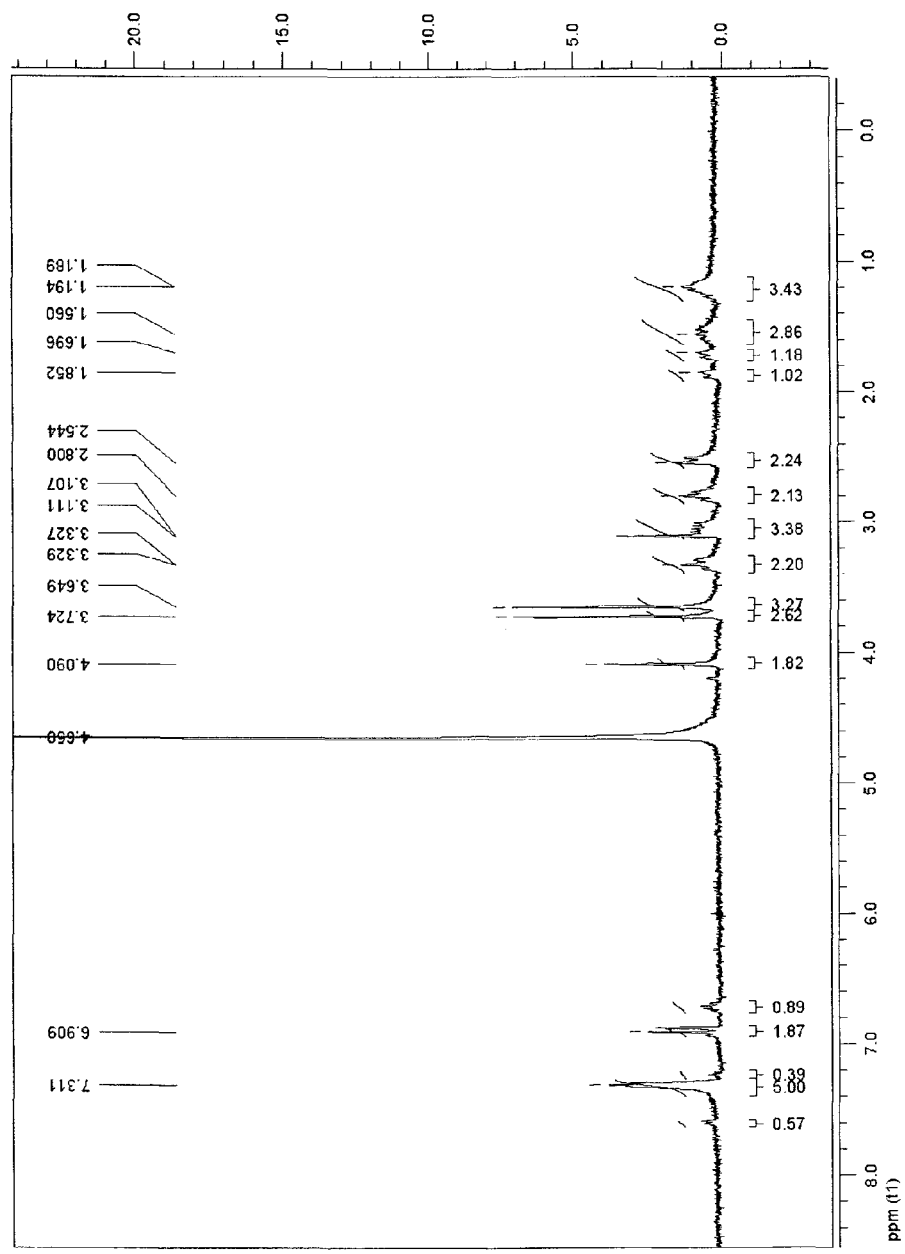
Figures 1, 19:
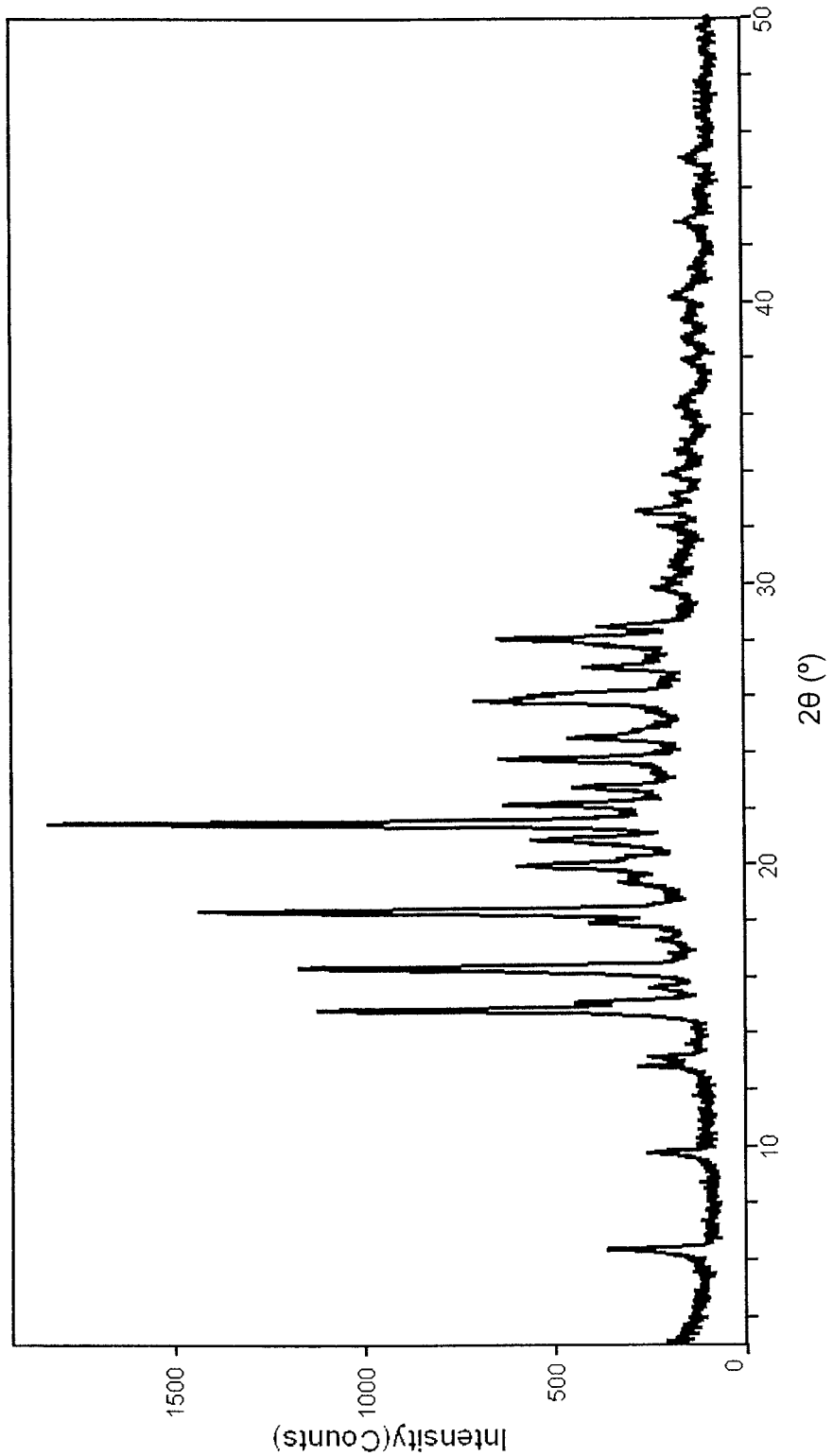
Figures 2, 19:
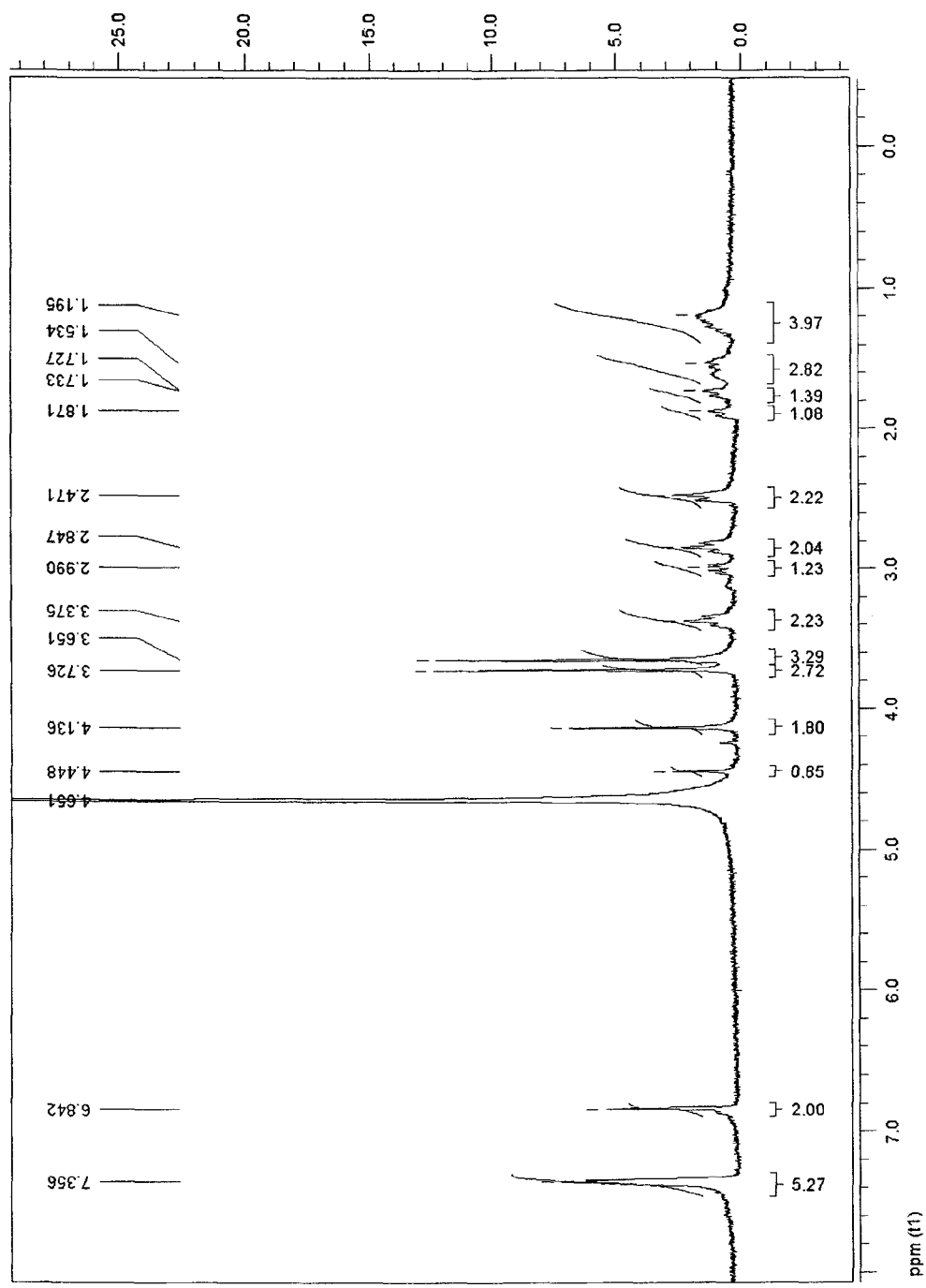
Figures 1, 20:
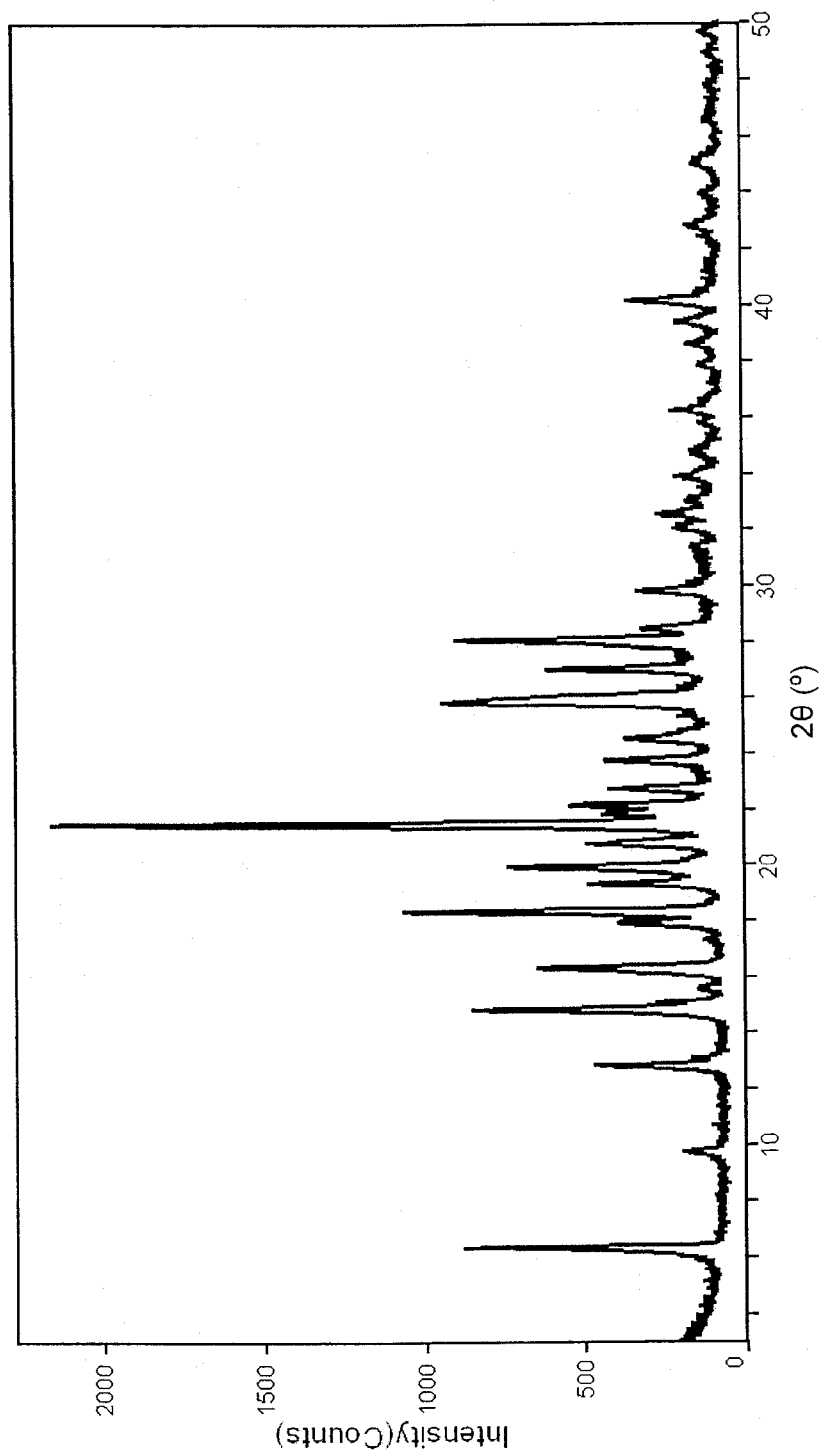
Figures 2, 20:
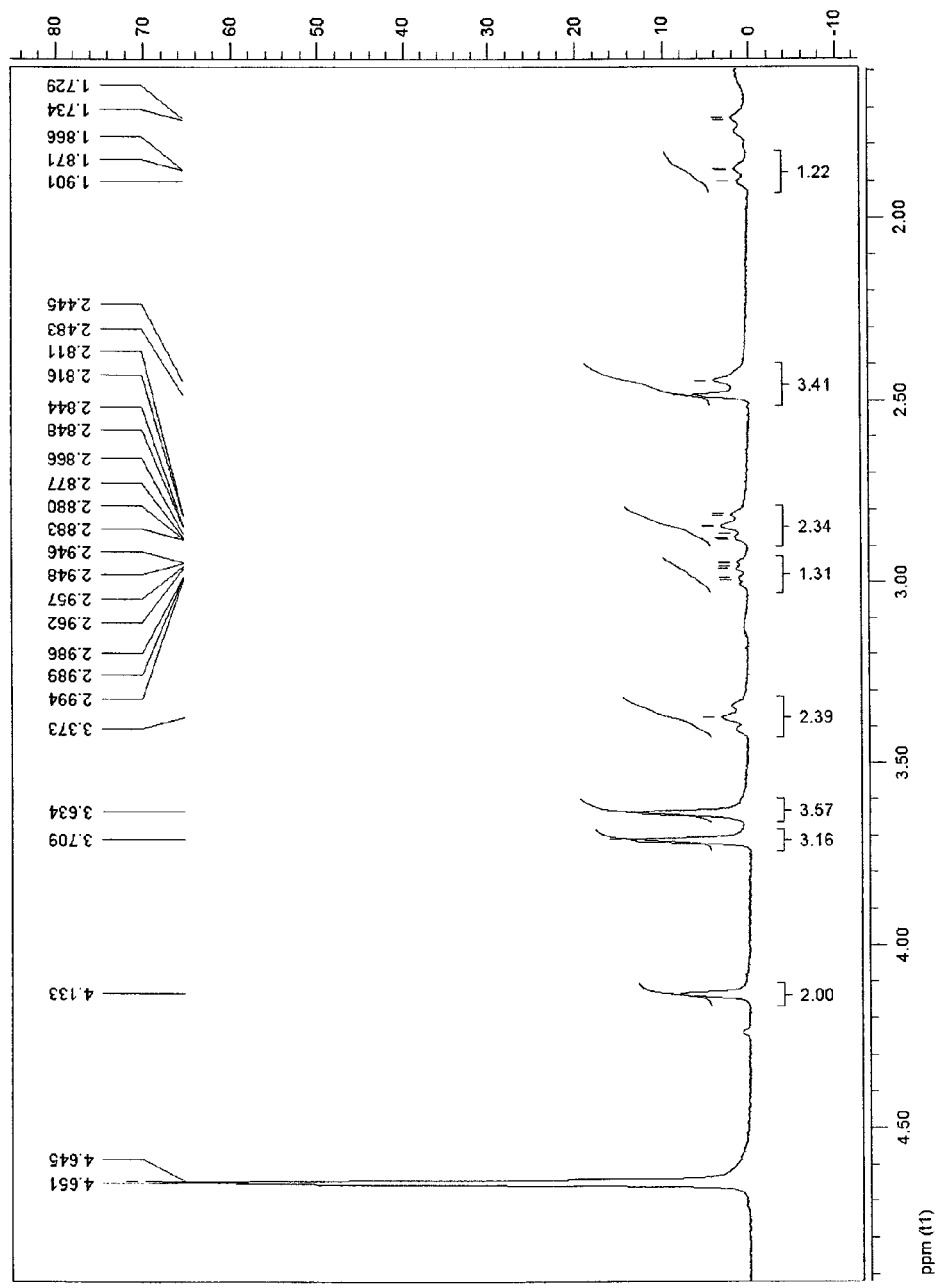

The invention claimed is:

1. A crystalline form of a compound of Formula (I):

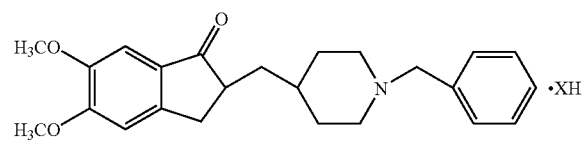

I wherein XH represents nitric acid and the crystalline form of the compound of Formula (I) has the following characteristic peaks in Powder X-ray Diffraction Pattern

| Diffraction Angle (2θ, °) | Intensity (I/I₀) |
|---|---|
| 6.34 | 14 |
| 10.00 | 63 |
| 12.08 | 35 |
| 12.78 | 45 |
| 13.64 | 16 |
| 16.12 | 15 |
| 17.14 | 100 |
| 18.74 | 10 |
| 19.28 | 16 |
| 19.98 | 24 |
| 20.24 | 33 |
| 21.32 | 12 |
| 21.88 | 16 |
| 22.46 | 63 |
| 22.98 | 42 |
| 23.76 | 26 |
| 24.26 | 36 |
| 27.62 | 36. |

2. The crystalline form of claim 1, wherein XH represents nitric acid, and the crystalline form has the following physical characteristics: X-ray powder diffraction pattern as shown in FIG. 6-A-1, infrared absorption spectrum as shown in FIG. 6-A-2, thermogravimetric and differential thermal analysis spectrum as shown in 6-A-3, and nuclear magnetic resonance spectrum as shown in FIG. 6-A-4.

3. A composition comprising a crystalline form of a compound of Formula (I) and a pharmaceutically acceptable excipient, wherein the composition is in a form of oral liquids, granules, buccal tablets, effervescent tablets, orally disintegrating tablets, lyophilized rapid dissolving tablets, ordinary tablets or chewable tablets:

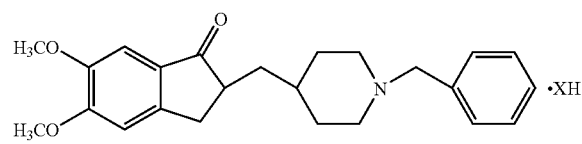

I wherein XH represents nitric acid, and the crystalline form of the compound of Formula (I) has the following characteristic peaks in Powder X-ray Diffraction Pattern

| Diffraction Angle (2θ, °) | Intensity (I/I₀) |
|---|---|
| 6.34 | 14 |
| 10.00 | 63 |
| 12.08 | 35 |
| 12.78 | 45 |
| 13.64 | 16 |
| 16.12 | 15 |
| 17.14 | 100 |
| 18.74 | 10 |
| 19.28 | 16 |
| 19.98 | 24 |
| 20.24 | 33 |
| 21.32 | 12 |
| 21.88 | 16 |
| 22.46 | 63 |
| 22.98 | 42 |
| 23.76 | 26 |
| 24.26 | 36 |
| 27.62 | 36. |

4. The composition of claim 3, wherein the composition is in the form of orally disintegrating tablets prepared from the following components expressed in weight percentage:

| | | | |
|---|---|---|---|
| the crystaline form of the compound of Formula (I) wherein XH represents salicylic acid, nitric acid, gallic acid, or acetylsalicylic acid: | 1-20% | filler: | 35-90% |
| disintegrant: | 1-30% | flavoring agent: | 0.00-5% |
| lubricant: | 0.1-10% | glidant: | 0.01-5% |
| colorant: | 0-1% | binder: | 0-5%. |

5. A method for increasing acetylcholine at central nervous system receptors in a subject in need thereof, comprising administration to said subject of a therapeutically effective amount of crystalline form of a compound of Formula (I):

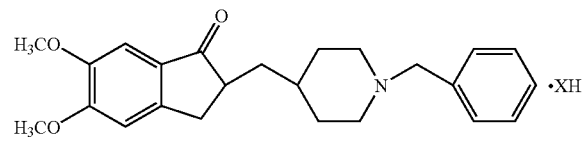

I wherein XH represents nitric acid, and the crystalline form of the compound of Formula (I) has the following characteristic peaks in Powder X-ray Diffraction Pattern

| Diffraction Angle (2θ, °) | Intensity ($I/I_0$) |
|---|---|
| 6.34 | 14 |
| 10.00 | 63 |
| 12.08 | 35 |
| 12.78 | 45 |
| 13.64 | 16 |
| 16.12 | 15 |
| 17.14 | 100 |
| 18.74 | 10 |
| 19.28 | 16 |
| 19.98 | 24 |
| 20.24 | 33 |
| 21.32 | 12 |
| 21.88 | 16 |
| 22.46 | 63 |
| 22.98 | 42 |
| 23.76 | 26 |
| 24.26 | 36 |
| 27.62 | 36. |

6. The method of claim 5; wherein the subject is diagnosed with senile dementia (AD), attention deficient disorder of childhood, memory deterioration, paralysis agitans (demeritia), brain injury, multiple sclerosis, Down's Syndrome, delirium, mood disorder, Huntington's disease, or sleep disorder.

7. The method of claim 5, wherein the therapeutically effective amount is in unit dosage crystalline form of the compound of Formula (I) ranging from 0.5 mg to 50 mg.

* * * * *

UNITED STATES PATENT AND TRADEMARK OFFICE
CERTIFICATE OF CORRECTION

PATENT NO. : 8,501,779 B2
APPLICATION NO. : 12/748248
DATED : August 6, 2013
INVENTOR(S) : Hesheng Zhang It is certified that error appears in the above-identified patent and that said Letters Patent is hereby corrected as shown below:

In the Claims

Column 67, Lines 5-8, Claim 4:
"wherein XH represents salicylic acid, nitric acid, gallic acid, or acetylsalicylic acid:" should read, --wherein XH represents nitric acid:--.

Column 68, Line 21, Claim 6:
"6. The method of claim 5; wherein the subject is diagnosed" should read, --6. The method of claim 5, wherein the subject is diagnosed--.

Column 68, Line 28, Claim 7:
"effective amount is in unit dosage crystalline form of the" should read, --effective amount is in unit dosage of the crystalline form of the--.

Signed and Sealed this
Twenty-sixth Day of August, 2014

Michelle K. Lee
*Deputy Director of the United States Patent and Trademark Office*